US005652358A

United States Patent [19]
Pfleiderer et al.

[11] Patent Number: 5,652,358
[45] Date of Patent: Jul. 29, 1997

[54] SOLID-PHASE SYNTHESIS OF OLIGORIBONUCLEOTIDES

[75] Inventors: Wolfgang Pfleiderer, Konstanz; Ralf Schnell, Krefeld; Stephan Matysiak, Radolfzell, all of Germany

[73] Assignee: Hoechst Aktiengesellschaft, Frankfurt am Main, Germany

[21] Appl. No.: 335,354

[22] Filed: Nov. 3, 1994

[30] Foreign Application Priority Data

Dec. 17, 1993 [DE] Germany .......................... 43 43 126.7

[51] Int. Cl.⁶ ........................ C07H 21/00; C07H 21/02; C07H 21/04
[52] U.S. Cl. .................. 536/25.3; 536/23.1; 536/24.1
[58] Field of Search ................ 536/23.1, 25.3, 536/24.1, 25.5

[56] References Cited

FOREIGN PATENT DOCUMENTS 03074398  8/1989  Japan .

OTHER PUBLICATIONS

Ogawa et al, "Solid phase synthesis of oligoribonucleotides using 5'–9–fluoroenylmethoxycarbonyl and 2'–1–isopropoxyl ethyl protection", Chem. Lett. 1169–1172 1991.
Takaku et al, "Use of 3,4–dimethoxybenzyl group as a protecting group for the 2'–hydroxyl group in the synthesis of oligoribonucleotides", Chem. Lett. 1005–1008 1986.
Sekine et al, "Oligoribonucleotide synthesis by use of the 2-methylthiophenylthiomethyl (MPTM) group as the 2'-hydroxyl protecting group", Chem. Lett. 121–124 1991.
Biegelman et al, "Synthesis of 2'–modified nucleotides and their incorporation into hammerhead ribozymes", Nucleic Acids Res. 23(21):4434-4442 1995.
Khorana, "Nucleic Acid Synthesis," Pure Appl. Chem., vol. 17,1968, pp. 349–381.
Reese, "The Chemical Synthesis of Oligo– and Poly–ribonucleotides," Nucleic Acids and Molecular Biology, vol. 3, 1989, pp. 164–181.
Beaucage et al., "Advances in the Synthesis of Oligonucleotides . . . ," Tetrahedron, vol. 48, No. 12, 1992, pp. 2223–2311.
Ohtsuka et al., "Chemical Synthesis of RNA," Synthesis and Application of DNA and RNA, 1987, pp. 115–132.
Sakatsume et al., "Solid Phase Synthesis of Oligoribonucleotides . . . ," Tetrahedron, vol. 47, No. 41, 1991, pp. 8717–8728.
Usman, "Automated Chemical Synthesis of Long Oligoribonucleotides . . . ," J. Am. Chem. Soc., vol. 109, 1987, pp. 7845–7854.
Ogilvie et al., "Total Chemical Synthesis of a 77–nucleotide–long RNA . . . ," Proc. Natl. Acad. Sci., USA, 1988, pp. 5764–5768.
Lyttle et al., "New Nucleoside Phosphoramidites and Coupling . . . ," J. Org. Chem., vol. 56, 1991, pp. 4608–4615.

Gasparutto et al., "Studies on the Formation of the Internucleotidic . . . ," Nucleosides & Nucleotides, vol. 9, No. 8, 1990, pp. 1087–1098.
Wu et al., "A Study on the Alkylsilyl Groups in Oligoribonucleotide . . . ," J. Org. Chem., vol. 55, No. 15, 1990, pp. 4717–4724.
Uhlmann et al., "Antisense Oligonucleotides: A New Therapeutic , . . . " Chemical Reviews, vol.90, No. 4, 1990, pp. 543–584.
S. Yamakage et al., "The 1–(2–chloroethoxy)ethyl Group for the Protection of the 2'-Hydroxyl Group in the Synthesis of Oligoribonucleotides." Tetrahedron Letters, vol. 30, No. 46, 1989, pp. 6361–6364.
O. Saktsume et al., "Solid Phase Synthesis of Oligoribonucleotides by the Phosphoramidite Approach using 2'–0–1–(2–chloroethoxy)ethyl Protection." Tetrahedron, vol. 47, No. 41, Oct. 1991, pp. 8717–8728.
H. Takaku et al., "Preparation of Ribonucleoside Phosphoramidites for Solid–Phase Synthesis of Oligonucleotides.", Chem. Abstracts, vol. 116, No. 5, 1992, p. 840.
E. Rozners et al. "Evaluation of 2'–Hydroxyl Protection in RNA Synthesis using the H–Phosphonate Approach.", Nucleic Acids Research, vol. 22, No. 1, Jan. 11, 1994, pp. 94–99.

*Primary Examiner*—Mindy Fleisher
*Assistant Examiner*—Nancy J. Degen
*Attorney, Agent, or Firm*—Finnegan, Henderson, Farabow, Garrett & Dunner, L.L.P.

[57] ABSTRACT

A process for the preparation of oligoribonucleotides of the formula

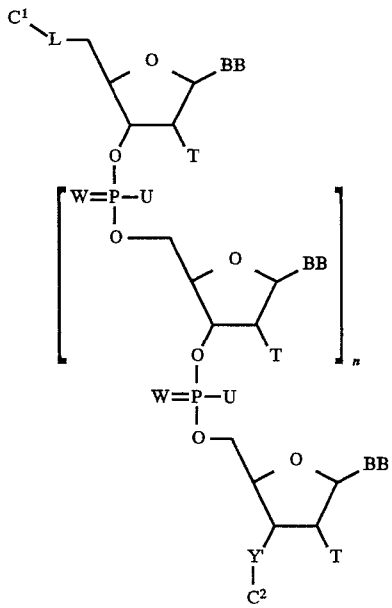

in which n, L, BB, W, T, Y', U, $C^1$ and $C^2$ are as defined in the description, by solid-phase synthesis is described, as are intermediates of the oligoribonucleotides.

31 Claims, No Drawings

SOLID-PHASE SYNTHESIS OF OLIGORIBONUCLEOTIDES

The chemical polycondensation of mononucleotides is an important method for preparing deoxyribonucleic acid (DNA) or ribonucleic acid (RNA).

A fundamental problem in the chemical synthesis of DNA or RNA is to find suitable protective groups for the amino and hydroxyl groups in the nucleoside bases and the sugar residues. These protective groups must, on the one hand, be stable under the conditions of the polycondensation reaction, i.e. during the reaction, and must, on the other hand, be sufficiently labile to be removable again at the end of the reaction without cleaving the phospho-diester linkage again [H. G. Khorana; Pure Appl. Chem. 17 (1968) 349].

There are particular problems with the chemical synthesis of RNA because the ribose sugar residue has two hydroxyl groups, both of which must be protected. The protective group for the 5'-hydroxyl group must moreover be eliminated again selectively, i.e. without eliminating the 2'-hydroxyl protective group, before each polycondensation step. By contrast the protective group for the 2'-hydroxyl group may be eliminated only at the end of the RNA synthesis, specifically under conditions which do not lead to cleavage or isomerization of the phospho-diester linkage [C. B. Reese, Nucleic Acids and Molecular Biology, Vol. 3, F. Eckstein & D. M. Lilley eds., Springer-Verlag Berlin-Heidelberg 1989, pages 164–181].

Efficient oligoribonucleotide synthesis on solid support materials therefore still differs greatly in its efficiency from the phosphoramidite method which functions well for assembling oligodeoxyribonucleotide chains. An overview is given by the papers by C. B. Reese [Nucleic Acids and Molecular Biology, Vol. 3, F. Eckstein & D. M. Lilley eds., Springer-Verlag Berlin-Heidelberg 1989, pages 164–181], S. L. Beaucage and R. P. Iyer [Tetrahedron 48 (1992) 2223–2311], E. Ohtsuka, S. Iwai [in Synthesis and Application of DNA and RNA, S. A. Narang, Ed., Academic Press, London 1987, pages 115–136] and O. Sakatsume et al. [Tetrahedron 47 (1991) 8717–8728].

Used in practice are, in particular, the 5'-O-dimethoxytrityl-2'-O-tert-butyldimethylsilyl-ribo-3'-O-(β-cyanoethyl, N-diisopropyl)phosphoramidites with acyl protection on the aglycones, which derive from studies by N. Usman et al. [J. Am. Chem. Soc. 109 (1987) 7845], K. K. Ogilvie et al. [Proc. Natl. Acad. Sci. USA 85 (1988) 5764]. These can also be bought. The oligoribonucleotide syntheses carried out therewith are, however, by no means satisfactory so that it is necessary to look for novel solutions [M. H. Lyttle et al.: J. Org. Chem. 56 (1991) 4608, D. Gasparutto et al.: Nucleosides & Nucleotides 9 (1990) 1087, T. Wu et al.: J. Org. Chem. 55 (1990) 4717].

A whole series of other protective group combinations for the 2'- and 5'-hydroxyl groups of the ribose sugar residue which are detailed in the abovementioned references have likewise not produced the desired success.

Besides the 2'-O-tert-butyldimethylsilyl protective group, certain acetal groups have been used as protective group for the 2' position. Systematic investigations by Reese, summarized, for example, in Beaucage, Tetrahedron 48 (1992) 223, have recently shown that acetal groups like the 1-(2-chlorophenyl)-4-methoxypiperidin-4-yl (Cpmp) or 1-(2-fluorophenyl)-4-methoxypiperidin-4-yl (Fpmp) radical on the 2'-OH group can be combined with the 5'-O-dimethoxytrityl radical and the 5'-pixyl radical (9-(9-phenyl) xanthenyl ether) because the latter groups are completely eliminated by weak acids before the acetal is attacked at all. These 5'-O-dimethoxytrityl-2'-O-Fpmp-ribo-3'-O-(β-cyanoethyl, N-diisopropyl)phosphoramidites with acyl protection on the aglycones can also be bought.

One of the great advantages of acetal protective groups compared with silyl protective groups is that they can be introduced selectively into the 2' position without side reaction. Another advantage is that coupling, which decreases as the space filled by the 2' protective group increases, is more efficient with acetals. Thus, for example, the coupling of ribonucleotide monomers protected by 2'-O-tetrahydropyranyl (2'-O-Thp) is more efficient than that with the 2'-OTBDMS protective group which is particularly sterically demanding.

The study by O. Sakatsume et al. [Tetrahedron 47 (1991) 8717–8728] on the introduction of the 2'-O-1-(2-chloroethoxy)ethyl protective group (Cee) shows that further accurate matching of acetal protective groups with the 5'-O-dimethoxytrityl radical and the 5'-pixyl radical is advisable.

Surprisingly, we have been able to find protective groups for the 2'-hydroxyl group which are superior to those hitherto described in respect of RNA synthesis. The criteria for this are, in particular, the simple and selective preparation of the monomer building blocks and the efficiency of coupling of the monomers. The protective group ought to be somewhat more stable than, for example, Ctmp towards 1.5% dichloroacetic acid, which is used for deprotection of the 5'-OH group during the coupling cycle, and, on the other hand, still sufficiently acid-labile to be amenable to rapid elimination at the end of the synthesis.

Oligonucleotide syntheses with these novel 2'-acetal-protected oligoribonucleotide phosphite amidites have taken place very successfully. The fact that on use of protective groups which can undergo β elimination they can even he eliminated on the solid support ensures simple purification and isolation of the 2'-acetal-protected oligoribonucleotide. These compounds can also be regarded as a stable form of the oligoribonucleotide which, in contrast to unprotected oligoribonucleotides, can be stored without problems for a lengthy period in order then, at a later time, to be converted as required by acid treatment into the free oligomer.

Oligonucleotides which contain one or more ribonucleotide units in their protected form, in particular those which contain these at the 3' and/or 5' end, showed a greatly improved resistance to nucleases, with only slight changes in the hybridization properties. Oligonucleotides of this type are therefore suitable for use as antisense oligonucleotides or ribozymes [A. Peyman, E. Uhlmann, Chem. Rev. 90 (1990) 543].

The invention therefore relates to a process for the preparation of a compound of the formula I

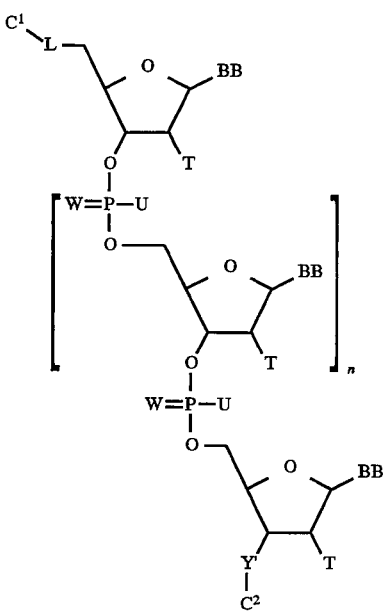

in which n is a number from 1–150, preferably 1–50, particularly preferably 8–30, very particularly preferably 8–20;

L is oxy, sulfanediyl or imino, preferably oxy;

BB is, independently of one another,

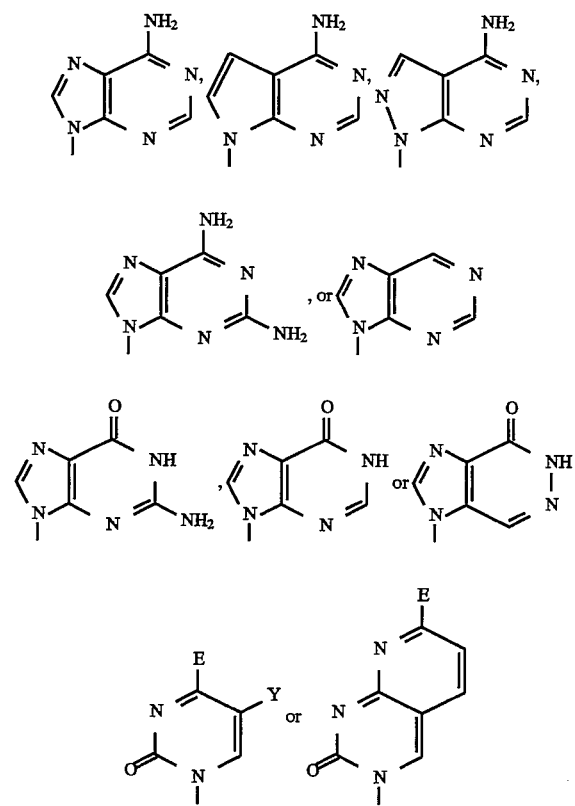

and

E is OH or $NH_2$ and

Y is hydrogen, $C_1$–$C_4$-alkyl, fluorine, chlorine, bromine or $C_2$–$C_6$-alkenyl, $C_2$–$C_6$-alkynyl, preferably hydrogen, $CH_3$ or 1-propynyl, particularly preferably hydrogen; or BB can, besides the natural nucleoside bases, also be other modified nucleoside bases such as 5-(hydroxymethyl) uridine, 5-aminouridine, pseudouridine, dihydrouridine, inosine, 8-aza-7-deazaadenosine, tubercidin, nebularins, xanthosine, 2-aminoadenosine, ethenoadenosine, 7-deazaguanosine, O4-methylthymidine, N6-methyladenosine, O6-methylguanosine or pyridopyrimidine nucleosides;

W is, independently of one another, oxygen or sulfur, preferably oxygen;

T is, independently of one another, hydrogen, —$OCH_3$, —O—$CH_2CH_3$, —O—$CH_2$—CH=$CH_2$ or OH, but OH in at least one case;

Y' is oxy, sulfanediyl, imino, $(CH_2)_k$ or $N(CH_2)_k$ where k is an integer from 1 to 18, preferably 1 to 6, and Y' is preferably oxy;

U is hydroxyl, mercapto, SeH, $C_1$–$C_{18}$-alkoxy, $C_1$–$C_{18}$-alkyl, $C_6$–$C_{20}$-aryl, $C_6$–$C_{14}$-aryl-$C_1$–$C_8$-alkyl, $NHR^{17}$, $NR^{17}R^{18}$ or a radical of the formula $(OCH_2CH_2)_cO(CH_2)_{c'}CH_2R^{20}$, and U is preferably hydroxyl, mercapto, $C_1$–$C_6$-alkoxy, $C_1$–$C_6$-alkyl, $NHR^{17}$, $NR^{17}R^{18}$, particularly preferably hydroxyl or $C_1$–$C_6$-alkyl; where $R^{17}$ is $C_1$–$C_{18}$-alkyl, $C_6$–$C_{20}$-aryl, $C_6$–$C_{14}$-aryl-$C_1$–$C_8$-alkyl, —$(CH_2)_d$—[NH($CH_2$)$_d$]$_{d'}$—$NR^{19}R^{19}$; preferably $C_1$–$C_8$-alkyl or methoxyethyl, particularly preferably $C_1$–$C_4$-alkyl or methoxyethyl, in which d is an integer from 2 to 6 and d' is an integer from 0 to 6, and $R^{18}$ is $C_1$–$C_{18}$-alkyl, $C_6$–$C_{20}$-aryl, $C_6$–$C_{14}$-aryl-$C_1$–$C_8$-alkyl or, in the case of $NR^{17}R^{18}$, together with $R^{17}$ and the nitrogen atom carrying them a 5–6-membered heterocyclic ring which can additionally contain another heteroatom from the series consisting of O, S and N, such as, for example, the morpholinyl and the imidazolidinyl ring;

$R^{19}$ is, independently of one another, hydrogen or $C_1$–$C_6$-alkyl or $C_1$–$C_4$-alkoxy-$C_1$–$C_6$-alkyl;

c is an integer from 1 to 100, preferably 3 to 20 and particularly preferably 3 to 8;

c' is an integer from 0 to 18, preferably 0 to 15;

$R^{20}$ is hydrogen or a functional group such as hydroxyl, amino, $NHR^{17}$, COOH, $CONH_2$, $COOR^{21}$ or fluorine, chlorine or bromine, with $R^{21}$ being $C_1$–$C_4$-alkyl, preferably methyl;

$C^1$ and $C^2$ are identical or different and are hydrogen, $C_1$–$C_{18}$-alkyl, $C_2$–$C_{18}$-alkenyl, $C_2$–$C_{18}$-alkynyl, $C_1$–$C_{18}$-alkylcarbonyl, $C_2$–$C_{18}$-alkenylcarbonyl, $C_2$–$C_{18}$-alkylnylcarbonyl, $C_6$–$C_{20}$-aryl, $C_6$–$C_{14}$-aryl-$C_1$–$C_8$-alkyl, or a radical of the formula II

where

W is as defined above;

Q and Q' are, independently of one another, hydroxyl, mercapto, SeH, $C_1$–$C_{22}$-alkoxy, —O—$(CH_2)_b$—$NR^{15}R^{16}$ with b being 1 to 6 and $R^{15}$ and $R^{16}$ being, independently of one another, hydrogen, $C_1$–$C_{18}$-alkyl, preferably $C_1$–$C_8$-alkyl, $C_6$–$C_{20}$-aryl, $C_6$–$C_{14}$-aryl-$C_1$–$C_8$-alkyl, $C_6$–$C_{14}$-aryl-$C_1$–$C_8$-alkoxy, where aryl is also heteroaryl, and aryl is optionally substituted by 1, 2 or 3 identical or different radicals from the series consisting of carboxyl, amino, nitro, $C_1$–$C_4$-alkylamino, $C_1$–$C_6$-alkoxy, hydroxyl, fluorine, chlorine, bromine and cyano, or is $C_1$–$C_{18}$-alkylmercapto, $NHR^{17}$, $NR^{17}R^{18}$ where $R^{17}$ and $R^{18}$ are as defined above, or together with the nitrogen atom carrying them a 3–6-membered ring or Q or Q' is preferably hydroxyl, mercapto, $OCH_2CH_3$, $O$-i-$C_3H_7$, $O$-n-$C_6H_{13}$, $O$-n-$C_{18}H_{37}$, $O$—$(CH_2)_3$-(3-pyridyl), $O$—$(CH_2)_2$-(4-nitrophenyl), farnesyl, phytyl, vitamin A, vitamin E, testosterone, cholesterol, $CH_3$, $O$—$(CH_2)_4$-(9-acridine); or Q and Q' are a radical of the formula III

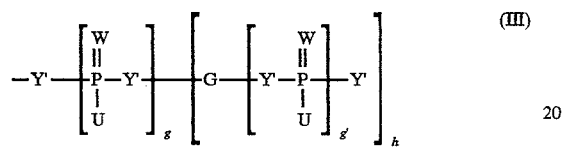

(III)

with g and g'=0 or 1,
h=0 to 10,

G is $C_2$–$C_{12}$-alkylene, in particular $C_2$–$C_4$-alkylene, $C_6$–$C_{14}$-aryl-di-$C_1$–$C_8$-alkylene, $C_6$–$C_{18}$-arylene, which can optionally be substituted once to three times by fluorine, chlorine, bromine, amino, hydroxyl, $C_1$–$C_{18}$-alkyl, $C_1$–$C_{18}$-alkoxy, $C_1$–$C_{18}$-alkoxycarbonyl, $C_6$–$C_{14}$-aryl, $C_6$–$C_{14}$-aryl-$C_1$–$C_{18}$-alkyl or $C_6$–$C_{14}$-aryl-$C_1$–$C_8$-alkoxy, or is a group of the formula $(CH_2CH_2N')_iCH_2CH_2$ or $(CH_2N')_iCH_2$ in which i is an integer from 1 to 11, preferably 1 to 5, and N' is oxy, sulfanediyl, imino or methylene, and W, U and Y' are as defined above; or Q and Q' are a group which favors intracellular uptake or acts as label of a DNA probe or attacks the target nucleic acid on hybridization of the oligonucleotide analog, with crosslinking or cleavage, where the nucleic acid sequence in formula I can also be interrupted one or more times by linkers of the formula III, and conjugates can be fondled by known processes also via the nucleic bases or via the phosphodiester or phosphothiodiester backbone;

$C^1$ and $C^2$ are particularly preferably hydrogen and a radical of the formula II with W=oxy and Q=Q'=hydroxyl;

which comprises a) protecting in the 3' and 5' position a compound of the formula IV

(IV)

which in

B is

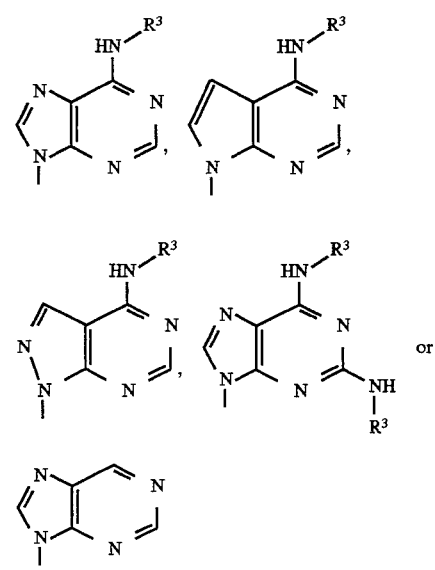

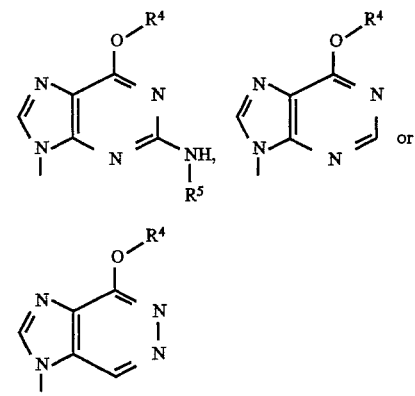

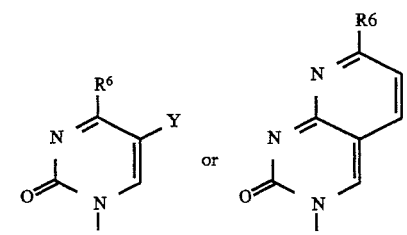

which in $R^3$ is, in each case, independently of one another, a group of the formula

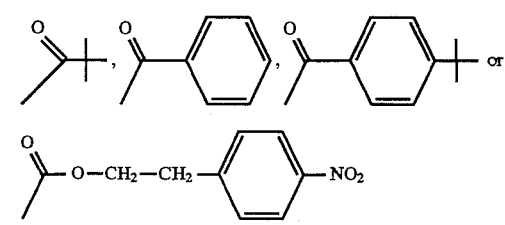

$R^4$ is hydrogen or 2-(p-nitrophenyl)ethyl;

$R^5$ is

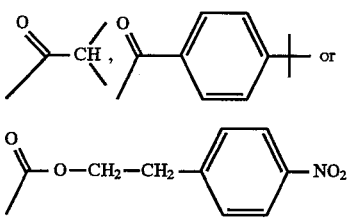

$R^6$ is OH, $NH_2$,

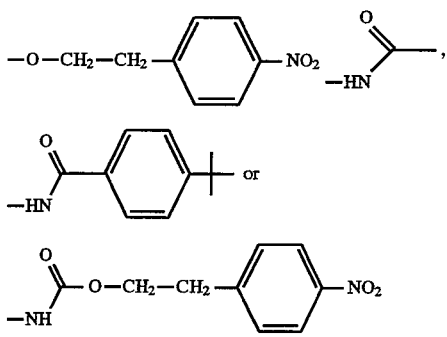

Y hydrogen, $C_1$-$C_4$-alkyl, fluorine, chlorine, bromine or $C_2$-$C_6$-alkenyl, $C_2$-$C_6$-alkynyl, preferably hydrogen, $CH_3$ or 1-propynyl, particularly preferably hydrogen; or B can, besides the natural nucleoside bases, also be other modified nucleoside bases whose amino or hydroxyl groups are protected by suitable known protective groups such as the para-nitrophenylethyloxycarbonyl group, the benzoyl group and the para-(t-butyl)benzoyl group for the hydroxyl group and the benzoyl, para-(t-butyl)benzoyl, para-nitrophenylethyloxycarbonyl, isobutyryl, para-(tert-butyl)phenylacetyl group for the amino group, where the nucleosides specified hereinafter with modified bases (BB) can be bought and the introduction of the individual protective groups can be carried out, for example by the method of C. Lehmann et al., Nucl. Acids Res. 17 (1989) 2379; C. B. Reese "The Chemical Synthesis of Oligo and Polyribonucleotides" in Nucleic Acids and Molecular Biology, Vol. 3, F. Eckstein & D. M. Lilley eds., Springer-Verlag Berlin-Heidelberg 1989, pages 164–181; E. Sonveaux, Bioorganic Chemistry 14 (1986) 274; A. Peyman, E. Uhlmann, Chem. Rev. 90 (1990) 543; S. L. Beaucage, R. P. Iyer, Tetrahedron 49 (1993) 1925, 2223, 6123: 5-(hydroxymethyl)uridine, 5-aminouridine, pseudouridine, dihydrouridine, inosine, 8-aza-7-deazaadenosine, tubercidin, nebularine, xanthosine, 2-aminoadenosine, ethenoadenosine, 7-deazaguanosine, O4-methylthymidine, N6-methyladenosine, O6-methylguanosine or pyridopyrimidine nucleosides, by any known processes, preferably by reaction with 1,3-dichloro-1,1,3,3-tetraisopropyldisiloxane by known processes, [for example in analogy to Markiewicz, J. Chem. Res., Synop. 1979, 24; Nucleic Acids Res. Symp. Ser. 7 (1980) 115], for example in pyridine at 0° C. to give the 3'-5'-O-(tetraisopropyldisiloxane-1,3-diyl)-protected compounds;

b) subsequently reacting the protected compound with the vinyl ether of the formula V

which in r is 1 or 2, and

X is $C_6$-$C_{12}$-aryl where aryl can be substituted one or more times, preferably once to three times, particularly preferably once or twice, by hydroxyl, mercapto, nitro, fluorine, chlorine, bromine, $C_1$-$C_6$-alkyl, $C_1$-$C_6$-alkoxy, $C_1$-$C_6$-alkylmercapto, $C_2$-$C_6$-alkenyl, $C_3$-$C_6$-alkynyl, C(O)OH, C(O)$NH_2$, C(O)O—$C_1$-$C_{18}$-alkyl, C(O)O—$C_6$-$C_{12}$-aryl, C(O)—$C_1$-$C_{18}$-alkyl, C(O)—$C_6$-$C_{12}$-aryl, O—C(O)$NH_2$, O—C(O)O—$C_1$-$C_{18}$-alkyl, O—C(O)O—$C_6$-$C_{12}$-aryl, O—C(O)—$C_1$-$C_{18}$-alkyl, O—C(O)—$C_6$-$C_{12}$-aryl, O—C(O)—[$CH_2$]$_r$—$X^1$ or O—C(O)O—[$CH_2$]$_r$—$X^1$, with $X^1$=$C_6$-$C_{12}$-aryl which can optionally be substituted once to three times by amino, hydroxyl, nitro, $C_1$-$C_6$-alkyl, $C_1$-$C_6$-alkoxy, $C_1$-$C_6$-alkoxycarbonyl, fluorine, chlorine or bromine;

for r=1, X is also phenyl or $C_1$-$C_4$-alkoxyphenyl;

for r=2, X is also CN, S-phenyl, $SO_2$-phenyl, N-phthalimide or $NO_2$;

for r=1, X is preferably $C_6$-$C_{12}$-aryl, where aryl can be substituted once or twice, preferably once, by fluorine, chlorine, bromine, $C_1$-$C_4$-alkyl or $C_1$-$C_4$-alkoxy and optionally once by O—C(O)—[$CH_2$]$_r$—$X^1$ or O—C(O)O—[$CH_2$]$_r$—$X^1$, with $X^1$ equal to $C_6$-$C_{12}$-aryl which can optionally be substituted once to three times by $C_1$-$C_4$-alkyl, $C_1$-$C_4$-alkoxy, fluorine, chlorine or bromine;

for r=2, X is preferably 4-nitrophenyl;

for r=1, X is particularly preferably 2,5-dichloro-4-pivaloyloxyphenyl, 3-chloro-4-[2-(4-nitrophenyl) ethoxycarbonyloxy]phenyl, 2-chloro-4-[2-(4-nitrophenyl)ethoxycarbonyloxy]phenyl, 3-fluoro-4-[2-(4-nitrophenyl)ethoxycarbonyloxy]phenyl, particularly preferably 3-fluoro-4-[2-(4-nitrophenyl) ethoxycarbonyloxy]phenyl;

in analogy to known processes [for example O. Sakatsume et al.; Tetrahedron 47 (1991) 8717–8728 and literature cited therein], i.e. for example the 3',5'-protected compound is reacted in a suitable organic solvent, for example toluene, with 1–20, preferably 1–10, particularly preferably 1–5, equivalents of the vinyl ether of the formula V, where appropriate after addition of a catalyst, preferably an acid, and the subsequent workup is carried out, where appropriate after neutralization, likewise by known processes such as, for example, extraction, crystallization, chromatography;

c) eliminating the 5' and 3' protected groups again, likewise in analogy to known processes, where in the case of the 3',5'-(O-tetraisopropyldisiloxane-1,3-diyl)-protected compound the protective group is eliminated, for example, with $HNEt_3^+F^-$;

d) introducing the 5' protective group with $R^2$=dimethoxytrityl, monomethoxytrityl, pixyl, trityl, preferably dimethoxytrityl, by known processes [for example M. J. Gait, Oligonucleotide Synthesis—a practical approach, IRL Press, 1984], for example the dimethoxytrityl group by reaction with dimethoxytrityl chloride in pyridine, resulting in a compound of the formula VI

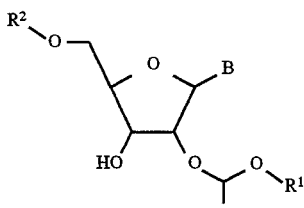
(VI)

in which
R$^1$ is —[CH$_2$]$_r$—X with
r=1 or 2 and

X is C$_6$–C$_{12}$-aryl where aryl can be substituted one or more times, preferably once to three times, particularly preferably once or twice, by hydroxyl, mercapto, nitro, fluorine, chlorine, bromine, C$_1$–C$_6$-alkyl, C$_1$–C$_6$-alkoxy, C$_1$–C$_6$-alkylmercapto, C$_2$–C$_6$-alkenyl, C$_3$–C$_6$-alkynyl, C(O)OH, C(O)NH$_2$, C(O)O—C$_1$–C$_{18}$-alkyl, C(O)O—C$_6$–C$_{12}$-aryl, C(O)—C$_1$–C$_{18}$-alkyl, C(O)—C$_6$–C$_{12}$-aryl, O—C(O)NH$_2$, O—C(O)O—C$_1$–C$_{18}$-alkyl, O—C(O)O—C$_6$–C$_{12}$-aryl, O—C(O)—C$_1$–C$_{18}$-alkyl, O—C(O)—C$_6$–C$_{12}$-aryl, O—C(O)—[CH$_2$]$_r$—X$^1$ or O—C(O)O—[CH$_2$]$_r$—X$^1$, with X$^1$=C$_6$–C$_{12}$-aryl which can optionally be substituted once to three times by amino, hydroxyl, nitro, C$_1$–C$_6$-alkyl, C$_1$–C$_6$-alkoxy, C$_1$–C$_6$-alkoxycarbonyl, fluorine, chlorine or bromine;

for r=1, X is also phenyl or C$_1$–C$_4$-alkoxyphenyl;

for r=2, X is also CN, S-phenyl, SO$_2$-phenyl, N-phthalimide or NO$_2$;

for r=1, X is preferably C$_6$–C$_{12}$-aryl, where aryl can be substituted once or twice, preferably once, by fluorine, chlorine, bromine, C$_1$–C$_4$-alkyl or C$_1$–C$_4$-alkoxy and optionally once by O—C(O)—[CH$_2$]$_r$—X$^1$ or O—C(O)O—[CH$_2$]$_r$—X$^1$, with X$^1$ equal to C$_6$–C$_{12}$-aryl which can optionally be substituted once to three times by C$_1$–C$_4$-alkyl, C$_1$–C$_4$-alkoxy, fluorine, chlorine or bromine;

for r=2, X is preferably 4-nitrophenyl;

for r=1, X is particularly preferably 2,5-dichloro-4-pivaloyloxyphenyl, 3-chloro-4-[2-(4-nitrophenyl)ethoxycarbonyloxy]phenyl, 2-chloro-4-[2-(4-nitrophenyl)ethoxycarbonyloxy]phenyl, 3-fluoro-4-[2-(4-nitrophenyl)ethoxycarbonyloxy]phenyl, particularly preferably 3-fluoro-4-[2-(4-nitrophenyl)ethoxycarbonyloxy]phenyl;

R$^2$ is dimethoxytrityl, monomethoxytrityl, pixyl, trityl, preferably dimethoxytrityl; and B is as defined above;

e) reacting the compound of the formula VI with a compound of the formula VII

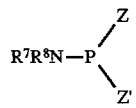
(VIII)

in which
Z' is OR$^9$ or C$_1$–C$_{18}$-alkyl, C$_1$–C$_{18}$-alkoxy, C$_6$–C$_{20}$-aryl, C$_6$–C$_{14}$-aryl-C$_1$–C$_8$-alkyl, preferably OR$^9$, C$_1$–C$_6$-alkyl, C$_1$–C$_6$-alkoxy, C$_6$–C$_{20}$-aryl, C$_6$–C$_{14}$-aryl-C$_1$–C$_8$-alkyl, particularly preferably OR$^9$;

R$^7$ and R$^8$ are identical or different and are C$_1$–C$_8$-alkyl, preferably isopropyl, or C$_5$–C$_{12}$-cycloalkyl, preferably up to C$_8$, benzyl or phenyl, or together with the nitrogen atom to which they are bonded are a saturated or unsaturated heterocyclic ring optionally with further heteroatoms, such as, for example, morpholine, and substituents such as OC(O)O—C$_1$–C$_4$-alkyl esters; and R$^9$ is a group of the formula

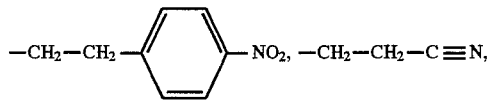

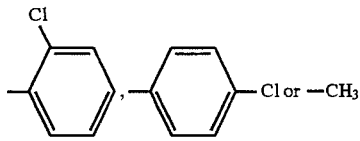

or a benzyl group, which is not substituted or is ring-substituted once to four times, preferably not substituted, where the substituent or substituents is or are, independently of one another, fluorine, chlorine, bromine, a C$_1$–C$_4$-alkyl, nitro, methoxy or carboxyl group;

Z is chlorine or bromine or a radical of the formula NR$^7$R$^8$ where R$^7$ and R$^8$ are as defined above;

in the presence of a base, preferably pyridine or a mixture of tetrahydrofuran (THF), dioxane, dichloromethane (DCM), chloroform and/or acetonitrile with a C$_1$–C$_4$-trialkylamine, preferably trimethyl-, triethyl- or diisopropylethylamine or, if Z is a radical of the formula NR$^7$R$^8$, then in the presence of a compound of the formula [HNR$^{12}$R$^{13}$R$^{14}$]$^{(+)}$A$^{(-)}$ where R$^{12}$, R$^{13}$, R$^{14}$ are identical or different and are a C$_1$–C$_4$-alkyl group and A=fluorine, chlorine, bromine, in particular chlorine, or tetrazole, preferably in the presence of tetrazole or, to give a compound of the formula VIII

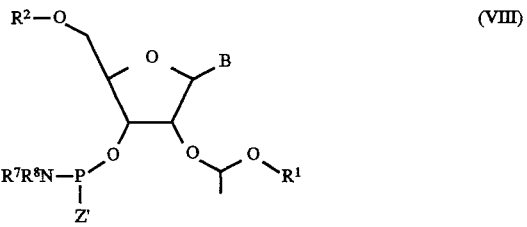
(VIII)

in which R$^1$, R$^2$, R$^7$, R$^8$, Z' and B are as defined above;

f) reacting the compound VI obtained according to d) by known processes with 1 to 10 equivalents, preferably with 1 to 2 equivalents, of a linker such as succinic anhydride in a suitable organic solvent, for example methylene chloride, where appropriate after addition of a catalyst, for example 4-dimethylaminopyridine, to give a compound of the formula IX

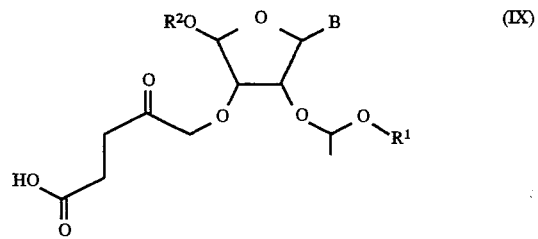
(IX)

where R$^1$, R$^2$ and B are as defined above, and subsequently working up by known processes, such as, for example, extraction, crystallization, chromatography, where the succinic acid residue in the 3' position acts as linker to the polymeric support used in the synthesis, and it is also possible, as alternative to the succinic acid linker, to use other linkers as described, for example, in Sonveaux [Bioorg. Chem. 14 (1986) 274];

g) coupling the compound of the formula X

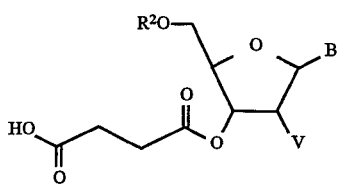

in which $R^2$ and B are as defined above;

V is hydrogen, O—$C_1$–$C_{18}$-alkyl, O—$C_1$–$C_{18}$-alkenyl, O—$C_1$–$C_{18}$-alkynyl or O—CH($CH_3$)—$OR^1$ in which $R^1$ is as defined above, preferably hydrogen, $OCH_3$, O—$CH_2CH_3$, O—$CH_2$—CH=$CH_2$ or O—CH($CH_3$)—$OR^1$ in which $R^1$ is as described above, by known processes to the solid support, such as aminopropyl-CPG (CPG=controlled pore glass), for example by reaction with DCC and p-nitrophenol in a suitable solvent [for example in M. J. Gait, Oligonucleotide Synthesis—a practical approach, IRL Press, 1984];

h) eliminating the 5' protective group by known processes, for example by treatment with 1–4% strength dichloroacetic acid in methylene chloride or chloroform;

i) reacting the resulting compound with a compound of the formula XI

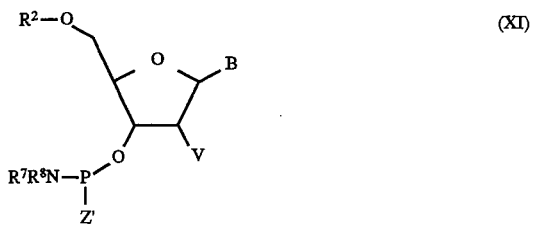

in which $R^2$, $R^7$, $R^8$, V, Z' and B are as defined above and j) oxidizing the resulting compound by known processes, for example by reaction with iodine in the presence of aqueous pyridine, lutidine or collidine, where appropriate also in the presence of other organic solvents such as, for example, tetrahydrofuran, or, for example, by reaction with N,N,N',N'-tetraethylthiuram disulfide in acetonitrile, or, for example, by reaction with iodine in the presence of alkylamine or arylamine, the various oxidation processes known to the skilled worker for preparing natural and modified oligonucleotides being summarized, for example, in Beaucage and Iyer [Tetrahedron 49 (1993) 6123] and Uhlmann and Peyman [Chem. Rev. 90 (1990) 543], and the oxidation preferably being carried out by reaction with iodine in the presence of aqueous pyridine, lutidine or collidine, where appropriate also in the presence of other organic solvents such as tetrahydrofuran;

k) repeating reaction steps h–j to the required chain length;

l) eliminating the oligonucleotide by known processes from the support, for example with $NH_3$ at 50°–60° C., and eliminating the protective groups on the phosphate and nucleic bases likewise by known processes, resulting in the compound of the formula XII

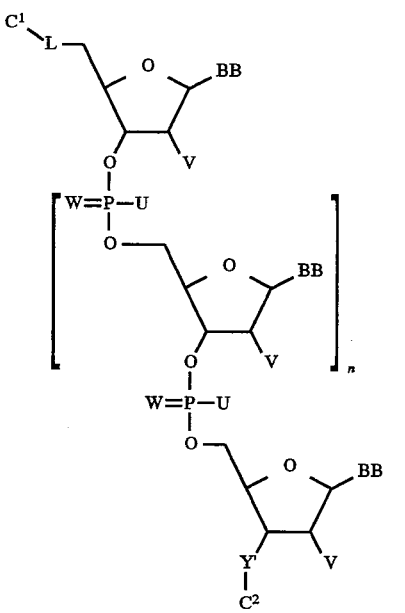

which n, LinBB, W, V, Y', U, $C^1$ and $C^2$ are as defined above;

m) incubating the compound of the formula XII in the acid range, preferably at pH 1–3, particularly preferably at pH 1.5–2.5, very particularly preferably at pH 1.8–2.2, with a 1–30%, preferably 2–6%, solution of p-toluenesulfonic acid in a suitable organic solvent, for example methylene chloride/methanol for 0.5–10 h, preferably 1–3 h, particularly preferably 3 h, subsequently neutralizing, for example with $NH_3$/methanol, and after evaporation of the solvent and after purification, for example by precipitation from ethanol, gel chromatography, gel electrophoresis and HPLC, obtaining the compound of the formula I [see also E. Sonveaux, Bioorg. Chem. 14 (1986) 274].

Examples of groups which favor intracellular uptake are various lipophilic radicals such as —O—$(CH_2)_x$—$CH_3$ in which x is an integer from 6–18, —O—$(CH_2)_n$—CH=CH—$(CH_2)_m$—$CH_3$ in which n and m are, independently of one another, an integer from 6 to 12, —O—$(CH_2CH_2O)_4$—$(CH_2)_9$—$CH_3$, —O—$(CH_2CH_2O)_8$—$(CH_2)_{13}$—$CH_3$ and —O—$(CH_2CH_2O)_7$—$(CH_2)_{15}$—$CH_3$, but also steroid residues such as cholesteryl and conjugates which utilize natural carrier systems such as bile acid, folic acid, 2-(N-alkyl-N-alkoxy)aminoanthraquinone and conjugates of mannose and peptides of the corresponding receptors which lead to receptor-mediated endocytosis of the oligonucleotides, such as EGF (epidermal growth factor), bradykinin and PDGF (platelet derived growth factor). Labeling groups mean fluorescent groups, for example of dansyl (=N-dimethyl-1-aminonaphthyl-5-sulfonyl), fluorescein or coumarin derivatives or chemiluminescent groups, for example of acridine derivatives, and the digoxigenin system which is detectable by ELISA, the biotin group which is detectable by the biotin/avidin system, or else linker arms with functional groups which permit subsequent derivatization with detectable reporter groups, for example an aminoalkyl linker which is reacted with an acridinium active ester to give the chemiluminescent sample. Typical labeling groups are

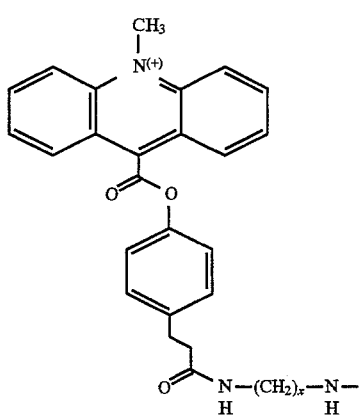

Acridinium esters

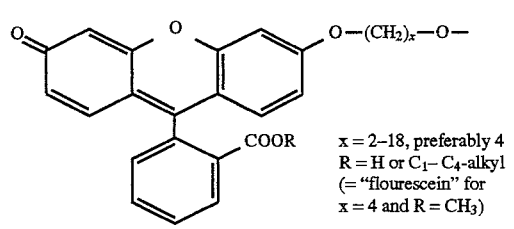

x = 2–18, preferably 4
R = H or $C_1$–$C_4$-alkyl
(= "flourescein" for x = 4 and R = $CH_3$)

Flourescein derivative

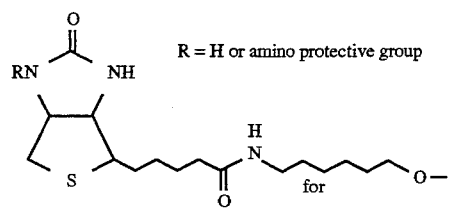

R = H or amino protective group

Biotin conjugate (= "Biotin" for R = Fmoc)

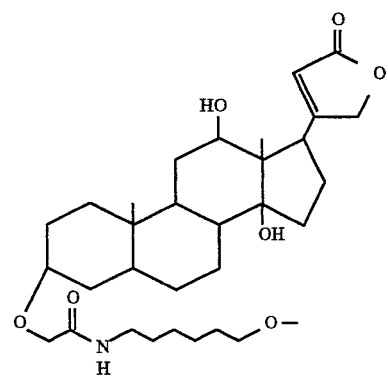

Digoxigen conjugate

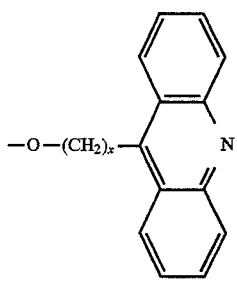

Acridine derivative x = 2–12, preferably 4

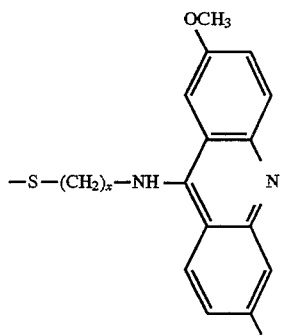

x = 2–12, preferably 4

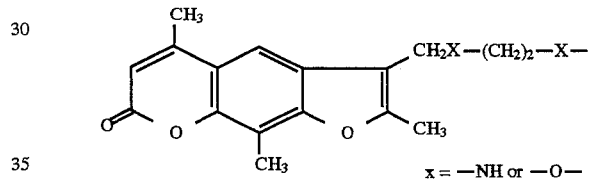

x = —NH or —O—

Trimethylpsoralen conjugate (="psoralen" for X=0)

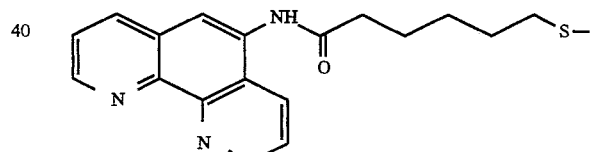

Phenanthroline conjugate

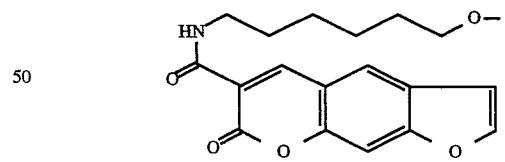

Psoralen conjugate

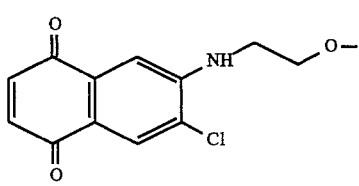

Naphthoquinone conjugate

Oligonucleotide analogs which bind to nucleic acids or intercalate and/or cleave or crosslink contain, for example, acridine, psoralen, phenanthroline, naphthoquinone, daunomycin or chloroethylaminoaryl conjugates. Typical intercalating and crosslinking radicals are:

-continued

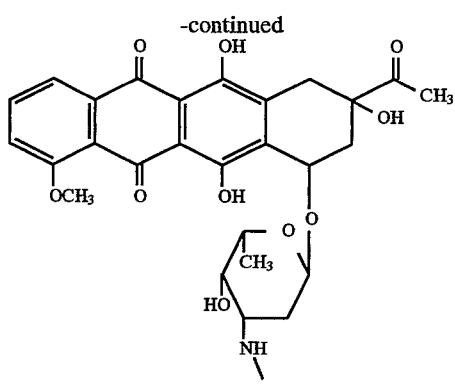

Daunomycin derivative

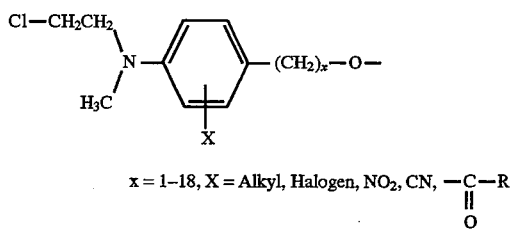

x = 1–18, X = Alkyl, Halogen, NO₂, CN, —C(=O)—R

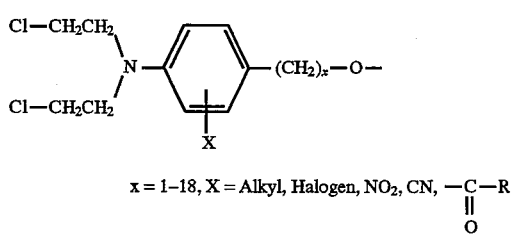

x = 1–18, X = Alkyl, Halogen, NO₂, CN, —C(=O)—R

The invention furthermore relates to the compounds of the formula VI

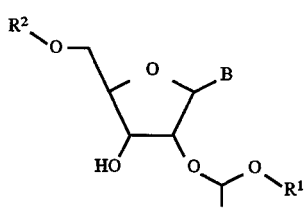

(VI)

in which
$R^1$ is —[CH$_2$]$_r$—X with
r=1 or 2 and
X is $C_6$–$C_{12}$-aryl where aryl can be substituted one or more times, preferably once to three times, particularly preferably once or twice, by hydroxyl, mercapto, nitro, fluorine, chlorine, bromine, $C_1$–$C_6$-alkyl, $C_1$–$C_6$-alkoxy, $C_1$–$C_6$-alkylmercapto, $C_2$–$C_6$-alkenyl, $C_3$–$C_6$-alkynyl, C(O)OH, C(O)NH$_2$, C(O)O—$C_1$–$C_{18}$-alkyl, C(O)O—$C_6$–$C_{12}$-aryl, C(O)—$C_1$–$C_{18}$-alkyl, C(O)—$C_6$–$C_{12}$-aryl, O—C(O)NH$_2$, O—C(O)O—$C_1$–$C_{18}$-alkyl, O—C(O)O—$C_6$–$C_{12}$-aryl, O—C(O)—$C_1$–$C_{18}$-alkyl, O—C(O)—$C_6$–$C_{12}$-aryl, O—C(O)—[CH$_2$]$_r$—X¹ or O—C(O)O—[CH$_2$]$_r$—X¹, with X¹=$C_6$–$C_{12}$-aryl which can be substituted once to three times by amino, hydroxyl, nitro, $C_1$–$C_6$-alkyl, $C_1$–$C_6$-alkoxy, $C_1$–$C_6$-alkoxycarbonyl, fluorine, chlorine or bromine;
for r=1, X is also phenyl or $C_1$–$C_4$-alkoxyphenyl;
for r=2, X is also CN, S-phenyl, SO$_2$-phenyl, N-phthalimide or NO$_2$;
for r=1, X is preferably $C_6$–$C_{12}$-aryl, where aryl can be substituted once to three times, preferably once or twice, by fluorine, chlorine, bromine, $C_1$–$C_4$-alkyl, $C_1$–$C_4$-alkoxy, O—C(O)—[CH$_2$]$_r$—X¹ or O—C(O)O—[CH$_2$]$_r$—X¹, with X¹ equal to $C_6$–$C_{12}$-aryl which can optionally be substituted once to three times by $C_1$–$C_4$-alkyl, $C_1$–$C_4$-alkoxy, fluorine, chlorine or bromine;
for r=2, X is preferably 4-nitrophenyl;
for r=1, X is particularly preferably 2,5-dichloro-4-pivaloyloxyphenyl, 3-chloro-4-[2-(4-nitrophenyl)ethoxycarbonyloxy]phenyl, 2-chloro-4-[2-(4-nitrophenyl)ethoxycarbonyloxy]phenyl, 3-fluoro-4-[2-(4-nitrophenyl)ethoxycarbonyloxy]phenyl, particularly preferably 3-fluoro-4-[2-(4-nitrophenyl)ethoxycarbonyloxy]phenyl;
$R^2$ is dimethoxytrityl, monomethoxytrityl, pixyl, trityl, preferably dimethoxytrityl;
B is

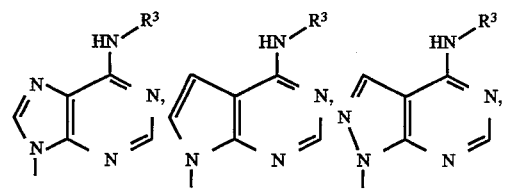

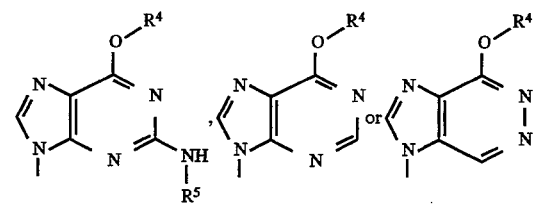

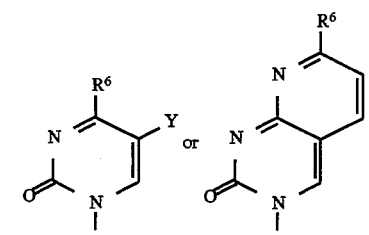

which in $R^3$ is, in each case independently of one another, a group of the formula

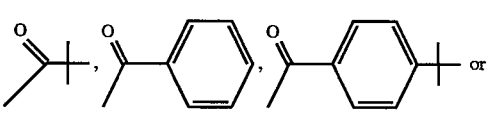

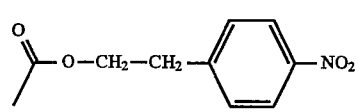

$R^4$ is hydrogen or 2-(p-nitrophenyl)ethyl;

$R^5$ is

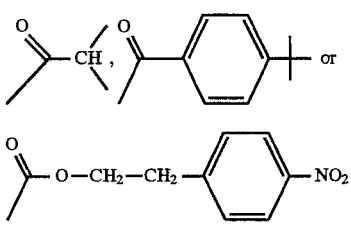

$R^6$ is OH, $NH_2$,

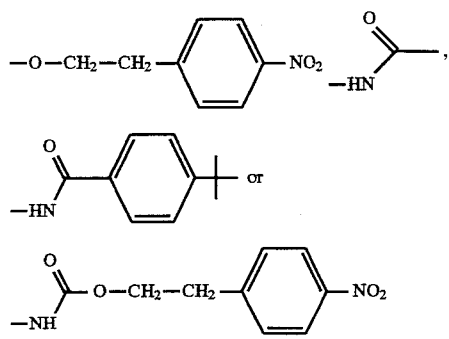

Y is hydrogen, $C_1$–$C_4$-alkyl, fluorine, chlorine, bromine or $C_2$–$C_6$-alkenyl, $C_2$–$C_6$-alkynyl, preferably hydrogen, $CH_3$ or 1-propynyl, particularly preferably hydrogen; or
B can, besides the natural nucleoside bases, also be other modified nucleoside bases whose amino or hydroxyl groups are protected by suitable known protective groups such as the para-nitrophenylethyloxycarbonyl group, the benzoyl group and the para-(t-butyl)benzoyl group for the hydroxyl group and the benzoyl, para-(t-butyl)benzoyl, para-nitrophenylethyloxycarbonyl, isobutyryl, para-(tert-butyl)phenylacetyl group for the amino group.

B in all compounds is preferably

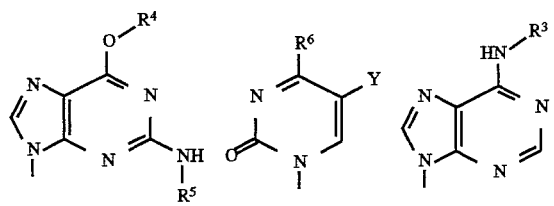

In the compounds of the formula VI, the sugar may assume the α configuration besides the natural β configuration, but compounds with the β sugar configuration are preferred.

The invention also relates to compounds of the formula VIII

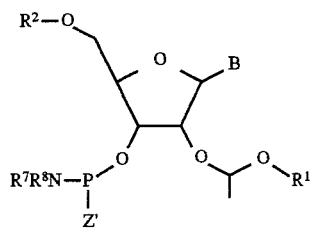

(VIII)

in which
$R^1$ is —$[CH_2]_r$—X, with
r=1 or 2 and

X is $C_6$–$C_{12}$-aryl where aryl can be substituted one or more times, preferably once to three times, particularly preferably once or twice, by hydroxyl, mercapto, nitro, fluorine, chlorine, bromine, $C_1$–$C_6$-alkyl, $C_1$–$C_6$-alkoxy, $C_1$–$C_6$-alkylmercapto, $C_2$–$C_6$-alkenyl, $C_3$–$C_6$-alkynyl, C(O)OH, C(O)$NH_2$, C(O)O—$C_1$–$C_{18}$-alkyl, C(O)O—$C_6$–$C_{12}$-aryl, C(O)—$C_1$–$C_{18}$-alkyl, C(O)—$C_6$–$C_{12}$-aryl, O—C(O)$NH_2$, O—C(O)O—$C_1$–$C_{18}$-alkyl, O—C(O)O—$C_6$–$C_{12}$-aryl, O—C(O)—$C_1$–$C_{18}$-alkyl, O—C(O)—$C_6$–$C_{12}$-aryl, O—C(O)—$[CH_2]_r$—$X^1$ or O—C(O)O—$[CH_2]_r$—$X^1$, with $X^1$=$C_6$–$C_{12}$-aryl which can optionally be substituted once to three times by amino, hydroxyl, nitro, $C_1$–$C_6$-alkyl, $C_1$–$C_6$-alkoxy, $C_1$–$C_6$-alkoxycarbonyl, fluorine, chlorine or bromine;

for r=1, X is also phenyl or $C_1$–$C_4$-alkoxyphenyl;
for r=2, X is also CN, S-phenyl, $SO_2$-phenyl, N-phthalimide or $NO_2$;
for r=1, X is preferably $C_6$–$C_{12}$-aryl, where aryl can be substituted once to three times, preferably once or twice, by fluorine, chlorine, bromine, $C_1$–$C_4$-alkyl, $C_1$–$C_4$-alkoxy, O—C(O)—$[CH_2]_r$—$X^1$ or O—C(O)O—$[CH_2]_r$—$X^1$, with $X^1$ equal to $C_6$–$C_{12}$-aryl which can optionally be substituted once to three times by $C_1$–$C_4$-alkyl, $C_1$–$C_4$-alkoxy, fluorine, chlorine or bromine;
for r=2, X is preferably 4-nitrophenyl;
for r=1, X is particularly preferably 2,5-dichloro-4-pivaloyloxyphenyl, 3-chloro-4-[2-(4-nitrophenyl)ethoxycarbonyloxy]phenyl, 2-chloro-4-[2-(4-nitrophenyl)ethoxycarbonyloxy]phenyl, 3-fluoro-4-[2-(4-nitrophenyl)ethoxycarbonyloxy]phenyl, particularly preferably 3-fluoro-4-[2-(4-nitrophenyl)ethoxycarbonyloxy]phenyl;

$R^2$ is dimethoxytrityl, monomethoxytrityl, pixyl, trityl, preferably dimethoxytrityl;

Z' is $OR^9$ or $C_1$–$C_{18}$-alkyl, $C_1$–$C_{18}$-alkoxy, $C_6$–$C_{20}$-aryl, $C_6$–$C_{14}$-aryl-$C_1$–$C_8$-alkyl, preferably $OR^9$, $C_1$–$C_6$-alkyl, $C_1$–$C_6$-alkoxy, $C_6$–$C_{20}$-aryl, $C_6$–$C_{14}$-aryl-$C_1$–$C_8$-alkyl, particularly preferably $OR^9$;

$R^7$ and $R^8$ are identical or different and are $C_1$–$C_8$-alkyl, preferably isopropyl, or $C_5$–$C_{12}$-cycloalkyl, preferably up to $C_8$, benzyl or phenyl, or together with the nitrogen atom to which they are bonded are a saturated or unsaturated heterocyclic ring optionally with further heteroatoms, such as, for example, morpholine, and substituents such as OC(O)O—$C_1$–$C_4$-alkyl esters; and $R^9$ is a group of the formula

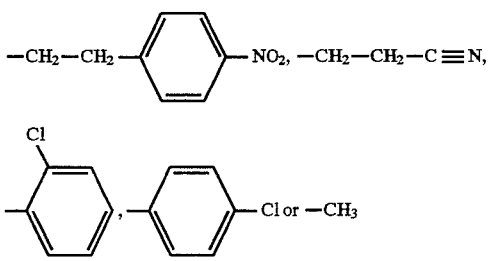

or a benzyl group, which is not substituted or is ring-substituted once to four times, preferably not substituted, where the substituent or substituents is or are, independently of one another, fluorine, chlorine, bromine, a $C_1$–$C_4$-alkyl, nitro, methoxy or carboxyl group;

B is

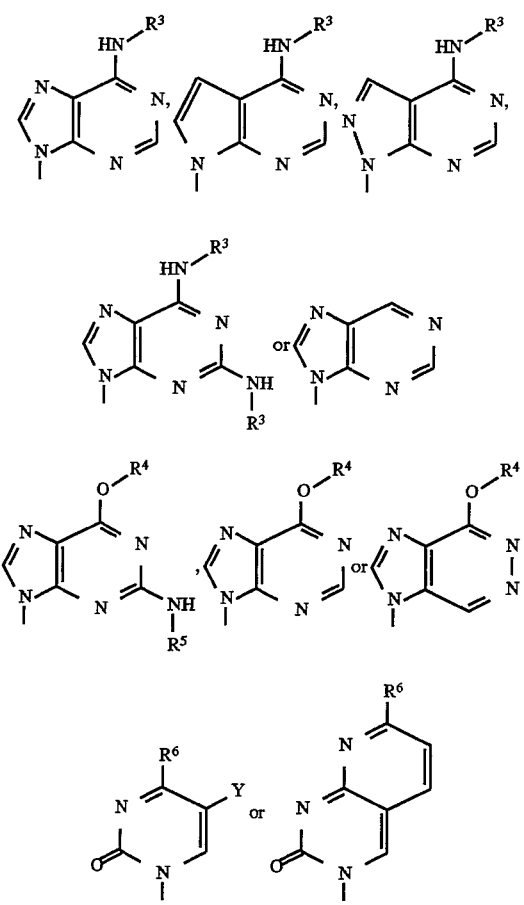

in which $R^3$ is, in each case independently of one another, a group of the formula

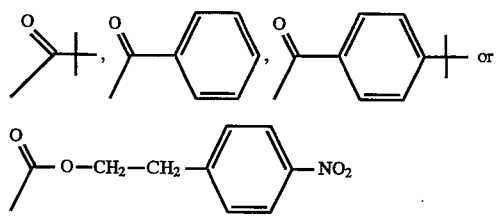

$R^4$ is hydrogen or 2-(p-nitrophenyl)ethyl;
$R^5$ is

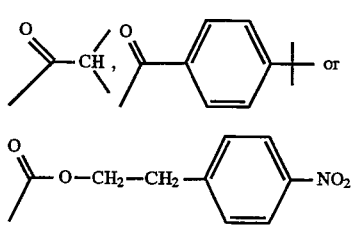

$R^6$ is OH, $NH_2$,

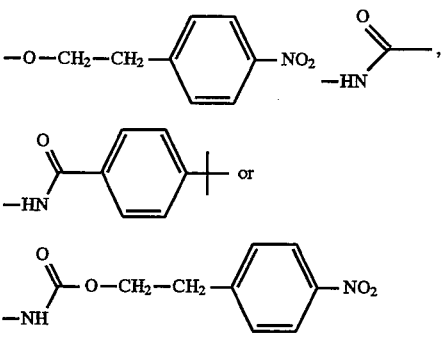

Y is hydrogen, $C_1$–$C_4$-alkyl, fluorine, chlorine, bromine or $C_2$–$C_6$-alkenyl, $C_2$–$C_6$-alkynyl, preferably hydrogen, $CH_3$ or 1-propynyl, particularly preferably hydrogen; or B can, besides the natural nucleoside bases, also be other modified nucleoside bases whose amino or hydroxyl groups are protected by suitable known protective groups such as the para-nitrophenylethyloxycarbonyl group, the benzoyl group and the para-(t-butyl)benzoyl group for the hydroxyl group and the benzoyl, para-(t-butyl)benzoyl, para-nitrophenylethyloxycarbonyl, isobutyryl, para-(tert-butyl)phenylacetyl group for the amino group.

The invention likewise relates to a compound of the formula XII

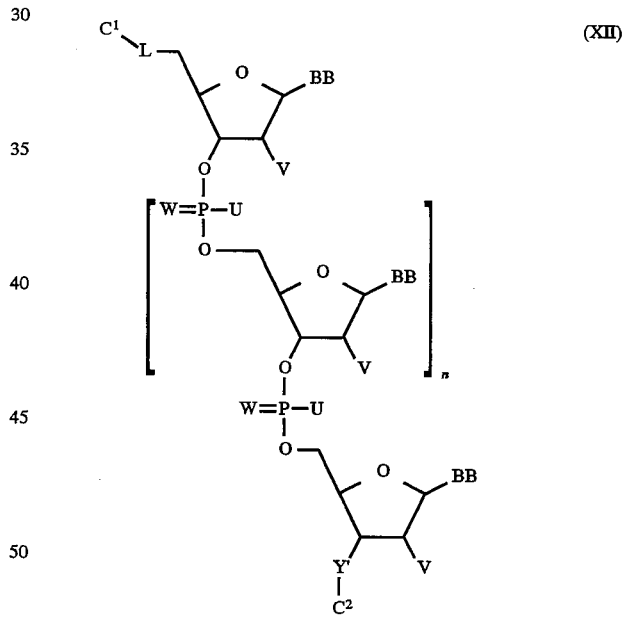

in which
n is a number from 1–150, preferably 4–50, particularly preferably 8–30, very particularly preferably 8–20;
L is oxy, sulfanediyl or imino, preferably oxy;
BB is, independently of one another,

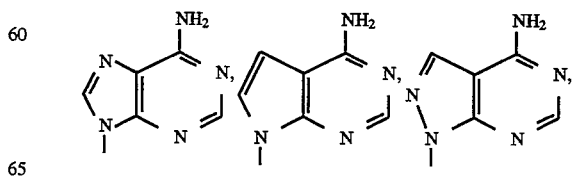

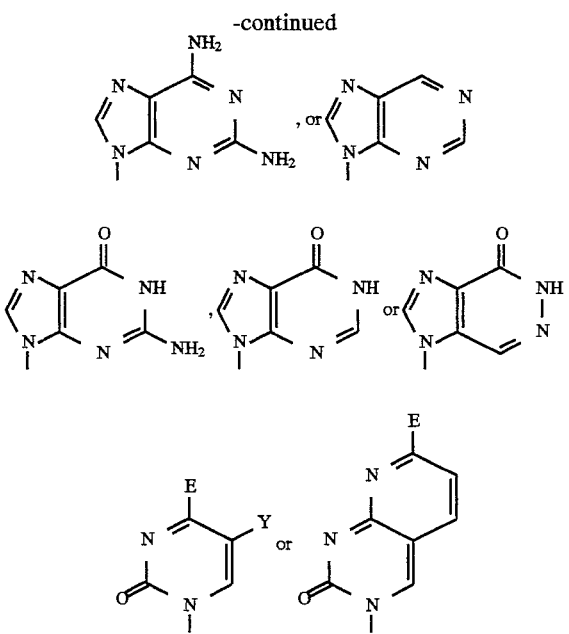

and

E is OH or NH₂ and

Y is hydrogen, $C_1$–$C_4$-alkyl, fluorine, chlorine, bromine or $C_2$–$C_6$-alkenyl, $C_2$–$C_6$-alkynyl, preferably hydrogen, $CH_3$ or 1-propynyl, particularly preferably hydrogen; or BB can, besides the natural nucleoside bases, also be other modified nucleoside bases such as 5-(hydroxymethyl) uridine, 5-aminouridine, pseudouridine, dihydrouridine, inosine, 8-aza-7-deazaadenosine, tubercidin, nebularine, xanthosine, 2-aminoadenosine, ethenoadenosine, 7-deazaguanosine, O4-methylthymidine, N6-methyladenosine, O6-methylguanosine or pyridopyrimidine nucleosides;

W is, independently of one another, oxygen or sulfur, preferably oxygen;

V is, independently of one another, hydrogen, —O—$C_1$-$C_{18}$-alkyl, —O—$C_1$-$C_{18}$-alkenyl, —O—$C_1$-$C_{18}$-alkynyl or —O—CH(CH₃)—OR¹ in which R¹ is as defined above, but is —O—CH(CH₃)—OR¹ in at least one case; preferably hydrogen, —OCH₃, —O—CH₂ CH₃, —O—CH₂—CH=CH₂ or —O—CH (CH₃)—OR¹, but —O—CH(CH₃)—OR¹ in at least one case;

Y' is oxy, sulfanediyl, imino, $(CH_2)_k$ or $N(CH_2)_k$ where k is an integer from 1 to 18, preferably 1 to 6, and Y' is preferably oxy;

U is hydroxyl, mercapto, SeH, $C_1$-$C_{18}$-alkoxy, $C_1$-$C_{18}$-alkyl, $C_6$-$C_{20}$-aryl, $C_6$-$C_{14}$-aryl-$C_1$-$C_8$-alkyl, $NHR^{17}$, $NR^{17}R^{18}$ or a radical of the formula $(OCH_2CH_2)_cO(CH_2)_c$-$CH_2R^{20}$, and U is preferably hydroxyl, mercapto, $C_1$-$C_6$-alkoxy, $C_1$-$C_6$-alkyl, $NHR^{17}$, $NR^{17}R^{18}$, particularly preferably hydroxyl or $C_1$-$C_6$-alkyl; where $R^{17}$ is $C_1$-$C_{18}$-alkyl, $C_6$-$C_{20}$-aryl, $C_6$-$C_{14}$-aryl-$C_1$-$C_8$-alkyl, —$(CH_2)_d$—[NH$(CH_2)_e$]$_{d'}$—$NR^{19}R^{19}$; preferably $C_1$-$C_8$-alkyl or methoxyethyl, particularly preferably $C_1$-$C_4$-alkyl or methoxyethyl, in which d is an integer from 2 to 6 and d' is an integer from 0 to 6, and $R^{18}$ is $C_1$-$C_{18}$-alkyl, $C_6$-$C_{20}$-aryl, $C_6$-$C_{14}$-aryl-$C_1$-$C_8$-alkyl or, in the case of $NR^{17}R^{18}$, together with $R^{17}$ and the nitrogen atom carrying them a 5–6-membered heterocyclic ring which can additionally contain another heteroatom from the series consisting of O, S and N, such as, for example, the morpholinyl and the imidazolinyl ring;

$R^{19}$ is, independently of one another, hydrogen or $C_1$-$C_6$-alkyl or $C_1$-$C_4$-alkoxy-$C_1$-$C_6$-alkyl;

c is an integer from 1 to 100, preferably 3 to 20 and particularly preferably 3 to 8;

c' is an integer from 0 to 18, preferably 0 to 15;

$R^{20}$ is hydrogen or a functional group such as hydroxyl, amino, $NHR^{17}$, COOH, $CONH_2$, $COOR^{21}$ or fluorine, chlorine or bromine, with $R^{21}$ being $C_1$-$C_4$-alkyl preferably methyl;

$C^1$ and $C^2$ are identical or different and are hydrogen, $C_1$-$C_{18}$-alkyl, $C_2$-$C_{18}$-alkenyl, $C_2$-$C_{18}$-alkynyl, $C_1$-$C_{18}$-alkylcarbonyl, $C_2$-$C_{18}$-alkenylcarbonyl, $C_2$-$C_{18}$-alkynylcarbonyl, $C_6$-$C_{20}$-aryl, $C_6$-$C_{14}$-aryl-$C_1$-$C_8$-alkyl, or a radical of the formula II

  (II)

where

W is as defined above;

Q and Q' are, independently of one another, hydroxyl, mercapto, SeH, $C_1$-$C_{22}$-alkoxy, —O—$(CH_2)_b$—$NR^{15}R^{16}$ with b being 1 to 6 and $R^{15}$ and $R^{16}$ being, independently of one another, hydrogen, $C_1$-$C_{18}$-alkyl, preferably $C_1$-$C_8$-alkyl, $C_6$-$C_{20}$-aryl, $C_6$-$C_{14}$-aryl-$C_1$-$C_8$-alkyl, $C_6$-$C_{14}$-aryl-$C_1$-$C_8$-alkoxy, where aryl is also heteroaryl, and aryl is optionally substituted by 1, 2 or 3 identical or different radicals from the series consisting of carboxyl, amino, nitro, $C_1$-$C_4$-alkylamino, $C_1$-$C_6$-alkoxy, hydroxyl, fluorine, chlorine, bromine and cyano, or is $C_1$-$C_{18}$-alkylmercapto, $NHR^{17}$, $NR^{17}R^{18}$ where $R^{17}$ and $R^{18}$ are as defined above, or together with the nitrogen atom carrying them a 3–6-membered ring or Q or Q' is preferably hydroxyl, mercapto, $OCH_2CH_3$, O-i-$C_3H_7$, O-n-$C_6H_{13}$, O-n-$C_{18}H_{37}$, O—$(CH_2)_3$-(3-pyridyl), O—$(CH_2)_2$-(4-nitrophenyl), farnesyl, phytyl, vitamin A, vitamin E, testosterone, cholesterol, $CH_3$, O—$(CH_2)_4$-(9-acridine); or Q and Q' are a radical of the formula III

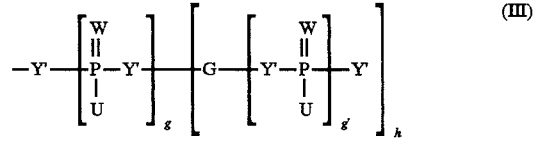  (III)

with g and g'=0 or 1, h=0 to 10,

G is $C_2$-$C_{12}$-alkylene, in particular $C_2$-$C_4$-alkylene, $C_6$-$C_{14}$-aryl-di-$C_1$-$C_8$-alkylene, $C_6$-$C_{18}$-arylene, which can optionally be substituted once to three times by fluorine, chlorine, bromine, amino, hydroxyl, $C_1$-$C_{18}$-alkyl, $C_1$-$C_{18}$-alkoxy, $C_1$-$C_{18}$-alkoxycarbonyl, $C_6$-$C_{14}$-aryl, $C_6$-$C_{14}$-aryl-$C_1$-$C_{18}$-alkyl or $C_6$-$C_{14}$-aryl-$C_1$-$C_8$-alkoxy, or is a group of the formula $(CH_2CH_2N')_iCH_2CH_2$ or $(CH_2N')_iCH_2$ in which i is an integer from 1 to 11, preferably 1 to 5, and N' is oxy, sulfanediyl, imino or methylene, and W, U and Y' are as defined above; or Q and Q' are a group which favors intracellular uptake or acts as label of a DNA probe or attacks the target nucleic acid on hybridization of the oligonucleotide analog, with crosslinking or cleavage, where the nucleic acid sequence in formula XII can also be interrupted one or more times by linkers of the formula III, and conjugates can be formed by known processes also via the nucleic bases or via the phosphodiester or phosphothiodiester backbone.

EXAMPLES

1.1 2'-O-(1-Benzyloxy)ethyl-$N^4$-NPEOC-3',5'-tetraisopropyldisiloxane-1,3-diylcytidine 678 mg (1.0 mmol) of 3',5'-protected $N^4$-NPEOC-cytidine are dissolved, and twice coevaporated in a rotary evaporator, in 10 ml of absolute toluene each time. The foam is then taken up in 30 ml of abs. toluene, 335 mg (2.5 mmol) of benzyl vinyl ether are added, and 2.0 ml (20 mg=0.11 mmol) of a stock solution of p-TsOH.$H_2O$ in abs. THF (1.0 g/100 ml) are added to the colorless solution. After it has been stirred at room temperature overnight (TLC check), the clear reaction solution is diluted to 200 ml with EA and extracted by shaking twice with 100 ml of saturated $NaHCO_3$ solution and 100 ml of saturated NaCl solution.

The aqueous phases are back-extracted with 100 ml of EA, and the combined organic phases are dried over $Na_2SO_4$, filtered and evaporated in a rotary evaporator. Further purification is by column chromatography on silica gel.

The product fractions are evaporated in a rotary evaporator and coevaporated several times with MeOH/$CH_2Cl_2$. This results in 690 mg (0.84 mmol) of colorless foam composed of the two diastereomers (P1+P2). This corresponds to a yield of 84% of theory;

1.2 2'-O-(1-Benzyloxyethyl)-$N^4$-NPEOC-cytidine 520 mg (0.64 mmol) of 2'-O-(1-benzyloxyethyl)-$N^4$-NPEOC-3',5'-tetraisopropyldisiloxane-1,3-diylcytidine (Example 1.1) are taken up in 32 ml of 0.2N $NH_4F$ solution (6.4 mmol) and stirred at room temperature overnight. The solution is concentrated almost to dryness in a rotary evaporator, and the resulting suspension is taken up in 5 ml of $CH_2Cl_2$ and briefly treated with ultrasound before the crude product is loaded onto the column. The column is charged with 20 g of silica gel and equilibrated with toluene.

Mobile phase gradients (toluene/EA/MeOH in ml): 100/0/0, 50/50/2.5, 50/50/5 (P1+P2); fractions each of 20 ml;

The product fractions are evaporated in a rotary evaporator and coevaporated several times with MeOH/$CH_2Cl_2$. This results in 320 mg (0.56 mmol) of colorless foam which is composed of the two diastereomers (P1+P2). This corresponds to a yield of 88% of theory.

1.3 2'-O-(1-Benzyloxyethyl)-5'-DMTR-$N^4$-NPEOC-cytidine 980 mg (1.72 mmol) of predried 2'-O-(1-benzyloxyethyl)-$N^4$-NPEOC-cytidine (Example 1.2) are coevaporated twice with 20 ml of abs. toluene each time in a rotary evaporator and then taken up in 10 ml of abs. pyridine, diluted with 50 ml of abs. toluene and subsequently 700 mg of DMTR-Cl (2.07 mmol) are added. The reaction solution is left to stir at room temperature overnight and the reaction is stopped by adding 1 ml of MeOH.

After 5 minutes, the solution is evaporated in a rotary evaporator in vacuo to an oil which is taken up in 200 ml of EA which is extracted by shaking twice with 100 ml of saturated $NaHCO_3$ solution and 100 ml of saturated NaCl solution. The aqueous phase is back-extracted with 150 ml of EA, and the combined org. phases are dried with $Na_2SO_4$, filtered and concentrated to an oil. Further purification is by column chromatography on silica gel.

The product fractions are evaporated in a rotary evaporator and coevaporated several times with MeOH/$CH_2Cl$. This results in 1.45 g (1.661 mmol) of chromatographically pure colorless foam which is composed of the two diastereomers (P1+P2). This corresponds to a yield of 97% of theory;

2. $N^4$-NPEOC-5'-O-DMTR-2'-O-(1-Benzyloxyethyl)cytidine-3'-O-phosphorous acid β-cyanoethyl ester N,N-diisopropylamide 450 mg (0.5 mmol) of 2'-O-(1-benzyloxyethyl)-5'-DMTR-$N^4$-NPEOC-cytidine (Example 1.3) are weighed into a 50 ml flask and coevaporated twice with 20 ml of abs. toluene each time. Subsequently 7.5 ml (1.25 mmol) of a stock solution of phosphitylation reagent (β-cyanoethyl N,N-diisopropylchlorophosphoramidite) (0.15 mol/l abs. $CH_2Cl_2$) are added, and the mixture is again concentrated to an oil. It is subsequently diluted with 10 ml of absolute acetonitrile and, after addition of 23 mg of tetrazole (0.33 mmol), the reaction solution is stirred at room temperature for 6 h. The reaction is stopped by pouring into 150 ml of $NaHCO_3$/EA (1/1) solution. The phases are separated in a separating funnel, extraction by shaking is repeated with 50 ml of EA, and the combined organic phases are washed with 50 ml of saturated NaCl solution. After drying over $Na_2SO_4$ and filtration, the filtrate is evaporated to an oil in a rotary evaporator.

Further purification is by chromatography. For this, a column with a diameter of 2 cm is charged with 20 g of silica gel and conditioned with toluene.

Mobile phase gradients (toluene/EA in ml): 100/0; 200/70; fractions each of 10 ml;

The product fractions are evaporated in a rotary evaporator and foamed with 10 ml portions of $CH_2Cl_2$/MeOH. The product is dried at room temperature under high vacuum. This results in 459 mg (0.426 mmol) of colorless foam which corresponds to a yield of 85% of theory.

3. 2'-O-(1-Benzyloxyethyl)-5'-DMTR-$N^4$-NPEOC-3'-O-succinylcytidine 330 mg (0.37 mmol) of 2'-O-(1-benzyloxyethyl)-5'-DMTR-$N^4$-NPEOC-cytidine (Example 1.3) are weighed into a 50 ml flask, 50 mg (0.490 mmol) of succinic anhydride and 60 mg of 4-DMAP are added, and the mixture is taken up in 10 ml of absolute methylene chloride. The resulting solution is stirred at room temperature for 14 h. The reaction is stopped by extraction by shaking with 50 ml of phosphate buffer (pH=6.0) after the reaction solution has been diluted with 100 ml of EA. The procedure is repeated once more, and the organic phase is extracted with buffer, dried over $Na_2SO_4$, filtered and concentrated to an oil in a rotary evaporator. Further purification is by chromatography on a column of diameter 2 cm charged with 15 g of silica gel and equilibrated with toluene.

Mobile phase gradients in ml (toluene/EA): 100/0, 200/50, 150/50 (P) and 100/100 (P); fractions each of 10 ml;

The product fractions are evaporated in a rotary evaporator, taken up in $CH_2Cl_2$ and filtered through a Pasteur pipette packed with cotton. The filtrate is again concentrated, foamed with MeOH and $CH_2Cl_2$ and dried under high vacuum. This results in 357 mg (0.361 mmol) of colorless foam. This corresponds to a yield of 98% of theory.

4.1 2'-O-(1-Benzyloxyethyl)-$N^6$-NPEOC-3',5'-tetraisopropyldisiloxane-1,3-diyladenosine 1.40 g (2.0 mmol) of 3',5'-tetraisopropyldisiloxane-protected $N^6$-NPEOC-adenosine are dissolved, and twice coevaporated in a rotary evaporator, in 10 ml of absolute toluene each time. The foam is then taken up in 30 ml of abs. toluene, 375 mg (2.8 mmol) of benzyl vinyl ether are added, and 2.0 ml (20 mg=0.11 mmol) of a stock solution of p-TsOH.$H_2O$ in abs. THF (1.0 g/100 ml) are added to the colorless solution. After it has been stirred at room temperature overnight (TLC check), the clear reaction solution is diluted to 200 ml with EA and extracted by shaking twice with 100 ml of saturated $NaHCO_3$ solution and 100 ml of saturated NaCl solution. The aqueous phases are back-extracted with 100 ml of EA, and the combined organic phases are filtered through $Na_2SO_4$ and evaporated in a rotary evaporator. Further purification is by chromatography on a column of diameter 3 cm charged with 40 g of silica gel and equilibrated with toluene.

Mobile phase gradients (toluene/EA in ml): 200/0, 160/40, 140/60, 100/100, 100/200 (P1+P2); fractions each of 20 ml;

The product fractions are evaporated in a rotary evaporator and coevaporated several times with MeOH/$CH_2Cl_2$. This results in 720 mg (0.74 mmol=37% of theory) of byproduct as a colorless foam composed of the two diastereomers (P1+P2) of the disubstituted product. The required product is isolated as colorless foam in 57% of theory (980 mg=1.13 mmol). The total yield is 94% of theory.

4.2 2'-O-(1-Benzyloxyethyl)-$N^6$-NPEOC-adenosine 2.08 g (2.40 mmol) of 2'-O-(1-benzyloxyethyl)-$N^6$-NPEOC-3',5'-tetraisopropyldisiloxane-1,3-diyladenosine (Example 4.1) are taken up in 120 ml of a 0.2N $NH_4F$ solution (24 mmol) and stirred at room temperature overnight. The solution is concentrated almost to dryness in a rotary evaporator, the resulting suspension is taken up in 20 ml of $CH_2Cl_2$ and briefly treated with ultrasound before loading the crude product onto a column.

The column is charged with 80 g of silica gel and conditioned with toluene.

Mobile phase gradients (toluene/EA/MeOH in ml): 200/0/0, 200/200,0, 200/200/20 (P1+P2); fractions each of 30 ml;

The product fractions are evaporated in a rotary evaporator and coevaporated several times with MeOH/$CH_2Cl_2$. This results in 1.38 g (2.321 mmol) of colorless foam composed of the two diastereomers (P1+P2). This corresponds to a yield of 97% of theory.

4.3 2'-O-(1-Benzyloxyethyl)-5'-DMTR-$N^6$-NPEOC-adenosine 1.120 g (1.84 mmol) of predried 2'-O-(1-benzyloxyethyl)-$N^6$-NPEOC-adenosine (Example 4.2) are coevaporated twice with 20 ml of abs. toluene each time in a rotary evaporator and then taken up in 20 ml of abs. pyridine, diluted with 50 ml of abs. toluene and subsequently 770 mg of DMTR-Cl (2.27 mmol) are added. The reaction solution is left to stir at room temperature overnight and the reaction is stopped by adding 1 ml of MeOH. After 5 minutes, the solution is evaporated in a rotary evaporator in vacuo to an oil which is taken up in 200 ml of EA which is extracted by shaking twice with 100 ml of saturated $NaHCO_3$ solution and 100 ml of saturated NaCl solution. The aqueous phase is back-extracted with 150 ml of EA, and the combined organic phases are dried with $Na_2SO_4$, filtered and concentrated to an oil. Further purification is by chromatography on a column of diameter 5 cm which is charged with 80 g of silica gel and equilibrated with toluene.

Mobile phase gradients (toluene/EA/MeOH in ml): 200/0, 200/200, 200/200/10, 200/200/20, 200/200/40; fractions each of 30 ml;

The product fractions are evaporated in a rotary evaporator and coevaporated several times with MeOH/$CH_2Cl_2$. This results in 1.52 g (1.69 mmol) of chromatographically pure colorless foam composed of the two diastereomers (P1+P2). This corresponds to a yield of 90% of theory.

5. 2'-O-(benzyloxyethyl)-5'-O-DMTR-$N^6$-NPEOC-adenosine-3'-O-phosphorous acid β-cyanoethyl ester N,N-diisopropylamide 450 mg (0.5 mmol) of 2'-O-(1-benzyloxyethyl)-5'-DMTR-$N^6$-NPEOC-adenosine (Example 4.3) are weighed into a 50 ml flask and coevaporated twice with 20 ml of abs. toluene each time. Subsequently 7.5 ml (1.1 mmol) of a stock solution of phosphitylation reagent (0.15 mol/l abs. $CH_2Cl_2$) are added and the mixture is again concentrated to an oil. The oil is then diluted with 10 ml of abs. acetonitrile and, after addition of 24 mg of tetrazole (0.38 mmol), the reaction solution is stirred. The reaction is stopped by pouring into 150 ml of $NaHCO_3$/EA (1/1) solution. The phases are separated in a separating funnel, extraction by shaking with 50 ml of EA is repeated, and the combined organic phases are washed with 50 ml of saturated NaCl solution. After drying over $Na_2SO_4$ and filtering, the filtrate is evaporated to an oil in a rotary evaporator. Further purification is by chromatography. For this, a column of diameter 2 cm is charged with 20 g of silica gel and conditioned with toluene.

Mobile phase gradients (toluene/EA in ml): 100/0; 200/70; fractions each of 10 ml;

The product fractions are evaporated in a rotary evaporator and foamed with 10 ml portions of $CH_2Cl_2$/MeOH. The product is dried at room temperature under high vacuum. This results in 390 mg (0.340 mmol) of colorless foam. The yield is thus 68% of theory.

6. $N^6$-NPEOC-5'-DMTR-3'-Succinoyl-2'-O-(1-benzyloxyethyl)adenosine 330 g of 2'-O-(2-benzyloxyethyl)-5'-DMTR-$N^6$-NPEOC-adenosine (Example 4.3) are weighed into a 50 ml flask, 50 mg (0.490 mmol) of succinic anhydride and 60 mg of 4-DMAP are added, and the mixture is taken up in 10 ml of absolute methylene chloride. The resulting solution is stirred at room temperature for 14 h. The reaction is stopped by extraction by shaking with 50 ml of phosphate buffer (pH= 6.0) after the reaction solution has been diluted with 100 ml of EA. The procedure is repeated once more, and the organic phases extracted with buffer, dried over $Na_2SO_4$, filtered and concentrated to an oil in a rotary evaporator. Further purification is by chromatography on a column of diameter 2 cm charged with 15 g of silica gel and equilibrated with toluene.

Mobile phase gradient in ml (toluene/EA): 100/0, 100/50 (P1+P2); Fractions each of 10 ml;

The product fractions are evaporated in a rotary evaporator, taken up in $CH_2Cl_2$ and filtered through a Pasteur pipette packed with cotton. The filtrate is again concentrated, foamed with MeOH and $CH_2Cl_2$ and dried under high vacuum. This results in 290 mg (0.29 mmol) of colorless foam. This corresponds to a yield of 79% of theory.

7.1 2'-O-(1-Benzyloxyethyl)-$N^2$-NPEOC-$O^6$-NPE-3,5'-tetraisopropyldisiloxane-1,3-diylguanosine 3.07 g (3.54 mmol) of 3',5'-tetraisopropyldisiloxane-protected $N^2$-NPEOC-$O^6$-NPE-guanosine are dissolved, and twice coevaporated in a rotary evaporator, in 20 ml of absolute toluene each time. The foam is then taken up in 80 ml of abs. toluene, 525 mg (3.91 mmol) of benzyl vinyl ether are added, and 5.0 ml (50 mg=0.27 mmol) of a stock solution of p-TsOH.$H_2O$ in abs. THF (1.0 g/100 ml) are added to the colorless solution. After it has been stirred at room temperature overnight (TLC check), the clear reaction solution is diluted to 300 ml with EA and extracted by shaking twice with 150 ml of saturated $NaHCO_3$ solution and 150 ml of saturated NaCl solution. The aqueous phases are back-extracted with 200 ml of EA, and the combined organic phases are dried over $Na_2SO_4$, filtered and evaporated in a rotary evaporator. Further purification is by chromatography on a column of diameter 3 cm charged with 90 g of silica gel and equilibrated with toluene.

Mobile phase gradients (toluene/EA in ml): 200/0, 250/50, 250/100 (P1+P2); fractions each of 30 ml;

The product fractions are evaporated in a rotary evaporator and coevaporated several times with MeOH/$CH_2Cl_2$. This results in 3.13 g (3.22 mmol) of colorless foam composed of the two diastereomers (P1+P2). This corresponds to a yield of 91% of theory.

7.2 2'-O-(1-Benzyloxyethyl)-$N^2$-NPEOC-$O^6$-NPE-guanosine 2.94 g (3.02 mmol) of $N^2$-NPEOC-$O^6$-NPE-2'-O-(1-benzyloxyethyl)-3',5'-tetraisopropyldisiloxane-1,3-diylguanosine (Example 7.1) are taken up in 150 ml of a 0.2N $NH_4F$ solution (30 mmol) and stirred at room temperature overnight. The solution is concentrated almost to dryness in a rotary evaporator, the resulting suspension is taken up in 20 ml of $CH_2Cl_2$ and briefly treated with ultrasound before the crude product is loaded onto a column. The column is charged with 80 g of silica gel and equilibrated with toluene.

Mobile phase gradients (toluene/EA/MeOH in ml): 200/0/0, 200/200/0, 200/200/20 (P1+P2); fractions each of 30 ml;

On concentration, the product crystallizes out and is filtered off through a Büchner funnel and washed with 50 ml of MeOH. A total of 2.10 g (2.764 mmol) of amorphous solid substance is obtained from two fractions and is composed of the two diastereomers (P1+P2). This corresponds to a yield of 92% of theory.

7.3 2'-O-(1-Benzyloxyethyl)-5'-DMTR-$N^2$-NPEOC-$O^6$-NPE-guanosine 1.590 g (2.093 mmol) of predried 2'-O-((1-benzyloxyethyl)-$N^2$-NPEOC-$O^6$-NPE-guanosine (Example 7.2) are coevaporated twice with 30 ml of abs. toluene each time in a rotary evaporator, then taken up in 30 ml of abs. pyridine, diluted with 80 ml of abs. toluene and then 850 mg of DMTR-Cl (2.51 mmol) are added. The reaction solution is left to stir at room temperature overnight, and the reaction is stopped by adding 1 ml of MeOH. After 5 minutes, the solution is evaporated in a rotary evaporator in vacuo to an oil which is taken up in 200 ml of EA and extracted by shaking twice with 100 ml of saturated $NaHCO_3$ solution and 100 ml of saturated NaCl solution. The aqueous phase is back-extracted with 150 ml of EA, and the combined organic phases are dried with $Na_2SO_4$, filtered and concentrated to an oil. Further purification is by column chromatography on silica gel.

The product fractions are evaporated in a rotary evaporator and coevaporated several times with MeOH/$CH_2Cl_2$. This results in 2.190 g (2.06 mmol) of chromatographically pure colorless foam composed of the two diastereomers (P1+P2). This corresponds to a yield of 99% of theory.

8. $N^2$-NPEOC-$O^6$-NPE-5'-O-DMTR-2'-(1-Benzyloxyethyl)guanosine-3'-O-phosphorous acid β-cyanoethyl ester N,N-diisopropylamide 530 mg (0.5 mmol) of 2'-O-(1-benzyloxyethyl)-5'-DMTR-$N^2$-NPEOC-$O^6$-NPE-guanosine (Example 7.3) are weighed into a 50 ml flask and coevaporated twice with 20 ml of abs. toluene each time. Subsequently 7.25 ml of a stock solution of phosphitylation reagent (0.15 mol/l abs. $CH_2Cl_2$) are added and the mixture is concentrated to an oil. The oil is then diluted with 10 ml of acetonitrile and, after addition of 28 mg of tetrazole (0.38 mmol), the reaction solution is stirred. The reaction is stopped by pouring into 150 ml of $NaHCO_3$/EA (1/1) solution. The phases are separated in a separating funnel, extraction by shaking with 50 ml of EA is repeated, and the combined organic phases are washed with 50 ml of saturated NaCl solution. After drying over $Na_2SO_4$ and filtering, the filtrate is evaporated to an oil in a rotary evaporator. Further purification is by chromatography. For this, a column of diameter 2 cm is charged with 20 g of silica gel and conditioned with toluene.

Mobile phase gradients (toluene/EA in ml): 100/0; 200/70; fractions each of 10 ml;

The product fractions are evaporated in a rotary evaporator and foamed with 10 ml portions of $CH_2Cl_2$/MeOH. The product is dried at room temperature under high vacuum. This results in 510 mg (0.404 mmol) of colorless foam, which corresponds to a yield of 81% of theory.

9. 2'-O-(1-Benzyloxyethyl)-5'-DMTR-$N^2$-NPEOC-$O^6$-NPE-3'-O-succinoylguanosine 390 mg (0.367 mmol) of 2'-O-(1-benzyloxyethyl)-5'-DMTR-$N^2$-NPEOC-$O^6$-NPE-guanosine (Example 7.3) are weighed into a 50 ml flask, 58 mg (0.490 mmol) of succinic anhydride and 72 mg of 4-DMAP (0.589 mmol) are added, and the mixture is taken up in 10 ml of absolute methylene chloride. The resulting solution is stirred at room temperature overnight. The reaction is stopped by extraction by shaking with 50 ml of phosphate buffer (pH=6.0) after the reaction solution has been diluted with 100 ml of EA.

The procedure is repeated once more, and the organic phase is extracted with buffer, dried over $Na_2SO_4$, filtered and concentrated to an oil in a rotary evaporator. Further purification is by chromatography on a column of diameter 2 cm charged with 15 g of silica gel and equilibrated with toluene.

Mobile phase gradients in ml (toluene/EA): 100/0, 200/50, 150/50/ (P) and 100/100 (P); fractions each of 10 ml;

The product fractions are evaporated in a rotary evaporator, taken up in $CH_2Cl_2$ and filtered through a Pasteur pipette packed with cotton. The filtrate is again concentrated, foamed with MeOH and $CH_2Cl_2$ and dried under high vacuum. This results in 250 mg (0.22 mmol) of colorless foam. This corresponds to a yield of 61% of theory.

10.1 2'-O-(1-Benzyloxyethyl)-3',5'-tetraisopropyldisiloxane-1,3-diyluridine 4.86 g (10.9 mmol) of 3',5'-protected uridine are dissolved, and twice coevaporated in a rotary evaporator, in 30 ml of absolute toluene each time. The foam is then taken up in 80 ml of abs. toluene, 3.36 g (25.0 mmol) of benzyl vinyl ether are added, and 19.2 ml (192 mg=1.0 mmol) of a stock solution of p-TsOH.$H_2O$ in abs. THF (1.0 g/100 ml) are added to the colorless solution. After it has been stirred at room temperature overnight (TLC check), the clear reaction solution is diluted to 300 ml with EA and extracted by shaking twice with 100 ml of saturated $NaHCO_3$ solution and 100 ml of saturated NaCl solution. The aqueous phases are back-extracted with 100 ml of EA, and the combined organic phases are dried over $Na_2SO_4$, filtered and evaporated in a rotary evaporator. Further purification is by chromatography on a column of diameter 4 cm which is charged with 75 g of silica gel and equilibrated with toluene.

Mobile phase gradients (toluene/EA/MeOH in ml): 200/0, 250/50, 150/100 (P1+P2); fractions each of 50 ml;

The product fractions are evaporated in a rotary evaporator and coevaporated several times with MeOH/$CH_2Cl_2$. This results in 5.64 g (9.10 mmol) of colorless foam composed of the two diastereomers (P1+P2). This corresponds to a yield of 91% of theory.

10.2 2'-O-(1-Benzyloxyethyl)uridine 3.10 g (5.00 mmol) of 2'-O-(1-benzyloxyethyl)-3',5'-tetraisopropyldisiloxane-1,3-diyluridine (Example 10.1) are taken up in 250 ml of 0.2N $NH_4F$ solution (50 mmol) and stirred at room temperature overnight. The solution is concentrated almost to dryness in a rotary evaporator, and the resulting suspension is taken up in 50 ml of $CH_2Cl_2$ and briefly treated with ultrasound before the crude product is loaded onto a column (d=5 cm). The column is charged with 100 g of silica gel and equilibrated with toluene.

Mobile phase gradients: (toluene/EA/MeOH in ml): 300/0/0, 250/150/0, 150/150/15, 150/150/30 (P1+P2); fractions each of 50 ml;

The product fractions are evaporated in a rotary evaporator and coevaporated several times with MeOH/$CH_2Cl_2$. This results in 1.86 g (4.80 mmol) of colorless foam composed of the two diastereomers (P1+P2). This corresponds to a yield of 96% of theory.

10.3 2'-O-(1-Benzyloxyethyl)-5'-DMTR-uridine 780 mg (2.06 mmol) of predried 2'-O-(1-benzyloxyethyl) uridine (Example 10.2) are coevaporated twice with 10 ml of abs. toluene each time in a rotary evaporator, then taken up in 10 ml of abs. pyridine and subsequently 780 mg (2.26 mmol) of DMTR-Cl are added. The reaction solution is left to stir at room temperature overnight, and the reaction is stopped by adding 1 ml of MeOH. After 5 minutes, the solution is evaporated in a rotary evaporator in vacuo to an oil, which is taken up in 150 ml of EA and extracted by shaking twice with 50 ml of saturated $NaHCO_3$ solution and 50 ml of saturated NaCl solution. The aqueous phase is back-extracted with 50 ml of EA, and the combined organic phases are dried with $Na_2SO_4$, filtered and concentrated to an oil. Further purification is by chromatography on a column of diameter 3 cm which is charged with 30 g of silica gel and equilibrated with toluene.

Mobile phase gradients (toluene/EA/MeOH in ml): 200/0, 100/100, 100/100/5, 100/100/100; fractions each of 30 ml;

The product fractions are evaporated in a rotary evaporator and coevaporated several times with MeOH/$CH_2Cl_2$. This results in 1.29 g (1.90 mmol) of chromatographically pure colorless foam composed of the two diastereomers (P1+P2). This corresponds to a yield of 92% of theory.

11. 2'-O-(1-Benzyloxyethyl)-5'-O-DMTR-$N^4$-NPEOC-uridine-3'-O-(N,N-diisopropyl-2-cyanoethyl)phosphitamide 1.00 g (1.47 mmol) of 2'-O-(1-benzyloxyethyl)-5'-DMTR-uridine (Example 10.3) is weighed into a 50 ml flask and coevaporated twice with 20 ml of abs. toluene each time. Subsequently 20.0 ml (3 mmol) of a stock solution of phosphitylation reagent (0.15 mol/l abs. $CH_2Cl_2$) are added and the mixture is again concentrated to an oil. The oil is then diluted with 20 ml of acetonitrile and, after addition of 100 mg of tetrazole (1.49 mmol), the reaction solution is stirred. The reaction is stopped by pouring into 250 ml of $NaHCO_3$/EA (1/1) solution. The phases are separated in a separating funnel, extraction by shaking with 70 ml of EA is repeated, and the combined organic phases are washed with 70 ml of saturated NaCl solution. After drying over $Na_2SO_4$ and filtering, the filtrate is evaporated to an oil in a rotary evaporator. Further purification is by chromatography. For this, a column of diameter 2 cm is charged with 15 g of silica gel and conditioned with toluene.

Mobile phase gradients (toluene/EA in ml): 100/0; 100/100; fractions each of 10 ml;

The product fractions are evaporated in a rotary evaporator and foamed with 10 ml portions of $CH_2Cl_2$/MeOH. The product is dried at room temperature under high vacuum. This results in 1.23 g (1.40 mmol) of colorless foam which corresponds to a yield of 95% of theory.

12. 2'-O-(1-Benzyloxyethyl)-5'-DMTR-3'-succinoyluridine 250 mg (0.368 mmol) of 2'-O-(1-benzyloxyethyl)-5'-DMTR-uridine (Example 10.3) are weighed into a 50 ml flask, 50 mg (0.490 mmol) of succinic anhydride and 60 mg of 4-DMAP are added and the mixture is taken up in 10 ml of absolute methylene chloride. The resulting solution is stirred at room temperature for 14 h. The reaction is stopped by extraction by shaking with 50 ml of phosphate buffer (pH=6.0) after the reaction solution has been diluted with 100 ml of EA. The procedure is repeated once more, and the organic phase is extracted with buffer, dried over $Na_2SO_4$, filtered and concentrated to an oil in a rotary evaporator. Further purification is by chromatography on a column of diameter 2 cm which is charged with 15 g of silica gel and equilibrated with toluene.

Mobile phase gradients in ml (toluene/EA): 100/0, 200/50, 150/50 (P) and 100/100 (P); fractions each of 10 ml;

The product fractions are evaporated in a rotary evaporator, taken up in $CH_2Cl_2$ and filtered through a Pasteur pipette packed with cotton. The filtrate is again concentrated, foamed with MeOH and $CH_2Cl_2$ and dried under high vacuum. This results in 265 mg (0.340 mmol) of colorless foam. This corresponds to a yield of 93% of theory.

13.1 2'-O-[1-(4-Nitrophenylethoxy)ethyl]-3',5'-O-(1,1,3,3-tetraisopropyldisiloxane-1,3-diyl)uridine 2.0 g (4.10 mmol) of 3',5'-O-(1,1,3,3-tetraisopropyldisiloxane-1,3-diyl)uridine are dissolved in 40 ml of absolute dichloromethane, 3.07 mg (1.63 µmol) of p-TsOH.H$_2$O and 1.18 g (6.15 mmol) of 2-(4-nitrophenyl) ethyl vinyl ether are added, and the mixture is stirred at room temperature for 30 minutes. After the reaction is complete, the mixture is diluted with dichloromethane and extracted by shaking 3× with 90 ml of saturated sodium bicarbonate solution each time. The aqueous phases are back-extracted with dichloromethane, and all the organic phases are combined, dried over sodium sulfate, filtered and evaporated in a rotary evaporator. For purification, the residue is loaded onto a silica gel column (3.5×21.5 cm) and chromatographed with toluene (>300 ml), toluene/ethyl acetate 12:1 (480 ml), 11:1 (210 ml), 10:1 (220 ml), 9:1 (200 ml), 8:1 (180 ml), 7:1 (160 ml), 6:1 (140 ml), 5:1 (240 ml) and 4:1 (200 ml). The first product fraction is obtained after 1500 ml of mobile phase has been used. All the fractions which contain product are combined and evaporated in a rotary evaporator. The remaining solid residue is crystallized from 2 ml of toluene/ethyl acetate 1:1, and the crystals are filtered off with suction, washed with a little toluene/ethyl acetate 1:1 and dried at 40° C. under high vacuum. 2.3 g (3.38 mmol, 82%) of compound are obtained as pale yellow-colored crystals.

Melting point: 145° C.

TLC (silica gel): R$_f$: 0.47+0.55

Analysis: C$_{31}$H$_{49}$N$_3$O$_{10}$Si$_2$ (679.92)

| | | | |
|---|---|---|---|
| calculated | C 54.76 | H 7.26 | N 6.18 |
| found | 54.60 | 7.26 | 6.09 |

UV (methanol): $\lambda_{max}$ [nm] (1 g ε): 265 (4.28)

$^1$H-NMR (250 MHz, CDCl$_3$, TMS, ppm): 9.24 (m, 1H, H—N(3)); 8.12+8.09 (2d, o-H to NO$_2$(NPEE)); 7.94–7.88 (m, 1H, H—C(6)); 7.43+7.36 (2d, 2H, m-H to NO$_2$/NPEE)); 5.73–5.64 (m, 2H, H—C(1'), H—C(5)); 5.02–4.91 (m, 1H, CH(NPEE)); 4.26–3.60 (m, 7H, H—C(2'), α-CH$_2$(NPEE), H—C(3'), H—C(3'), H—C(4'), CH$_2$(5')); 3.03–2.92 (m, 2H, β-CH$_2$(NPEE)); 1.39+1.33 (2d, 3H, CH$_3$(NPEE)); 1.07–0.90 (m, 28H, isopropyl)

13.2 2'-O-[1-(4-Nitrophenylethoxy)ethyl]uridine 2.0 mg (2.95 mmol) of 2'-O-[1-(4-nitrophenylethoxy)ethyl]-3',5'-O-(1,1,3,3-tetraisopropyldisiloxane-1,3-diyl) uridine are dissolved in 8.0 ml of absolute tetrahydrofuran, 2.22 g (7.06 mmol) of tetrabutylammonium fluoride·3 H$_2$O are added, the mixture is stirred at room temperature for 25 minutes and evaporated in a rotary evaporator. For purification, the residue is loaded onto a silica gel column (3.5×18.0 cm) and chromatographed with dichloromethane (250 ml), dichloromethane/methanol 100:1 (250 ml), 98:1 (300 ml), 96:1 (300 ml), 94:1 (300 ml), 90:1 (250 ml), 85:1 (500 ml), 80:1 (400 ml) and, after 1400 ml of mobile phase have been used, the first product fraction is obtained. All fractions containing the product are combined and evaporated in a rotary evaporator. The solid residue is crystallized from 15 ml of ethyl acetate, the resulting precipitate is filtered off with suction and dried at 40° C. under high vacuum, and 1.13 g (2.59 mmol, 88%) of pale yellow-colored crystals of compound are isolated.

Melting point: 162° C.

TLC (silica gel): R$_f$=0.42+0.46 dichloromethane/methanol 9:1

Analysis: C$_{19}$H$_{23}$N$_3$O$_9$ (437.40)

| | | | |
|---|---|---|---|
| calculated | C 52.17 | H 5.30 | N 9.60 |
| found | 51.71 | 5.47 | 9.20 |

UV (methanol): $\lambda_{max}$ [nm] (1 g ε): 265 (4.23)

$^1$H-NMR (250 MHz, d$_6$-DMSO, ppm): 11.36 (s, 1H, H—N(6)); 8.12 (d, 2H, o-H to NO$_2$(NPEE)); 7.92–7.88 (m, 1H, H—C(6)); 7.47 (d, 2H, m-H to NO$_2$(NPEE)); 5.89–5.84 (m, 1H, H—C(1')); 5.65–5.62 (m, 1H, H—C(5)); 5.19–5.17 (m, 2H, HO—C(5')), HO—C(3')); 4.83–4.79 (m, 1H, CH(NPEE)); 4.16–3.50 (m, 7H, H—C(2'), H—C(3'), H—C(4'), α-CH$_2$(NPEE), CH$_2$(5')); 2.90–2.80 (m, 2H, β-CH$_2$(NPEE)); 1.22–1,1,13 (m, 3H, CH$_3$(NPEE)

13.3 2'-O-[1-(4-Nitrophenylethoxy)ethyl)uridine 3.0 g (6.16 mmol) of 3',5'-O-(1,1,3,3-tetraisopropyldisiloxane-1,3-diyl)uridine are dissolved in 60 ml of absolute dichloromethane and cooled to 0° C. in an ice/salt bath, 4.6 mg (24.18 µmol) of p-TsOH.H$_2$O and 1.78 g (9.24 mmol) of 4-nitrophenylethyl vinyl ether are added, and the mixture is stirred in the ice bath for 2–3 hours and subsequently neutralized with 0.5N sodium methanolate/methanol solution and evaporated in a rotary evaporator. The residue is taken up in dichloromethane and washed 3× with 90 ml of saturated sodium bicarbonate solution each time, the aqueous phases are back-extracted with dichloromethane, and all the organic phases are combined, dried over sodium sulfate, filtered and evaporated in a rotary evaporator.

The residue is dissolved in 13.0 ml of absolute tetrahydrofuran, 4.08 g (0.013 mol) of tetrabutylammonium fluoride·3 H$_2$O are added, and the mixture is stirred at room temperature for 1.¼ hours and subsequently evaporated in a rotary evaporator. For purification, the remaining residue is loaded onto a flash silica gel column (3.0×19.0 cm) and eluted with dichloromethane (250 ml), dichloromethane/methanol 100:1 (250 ml), 95:1 (285 ml), 90:1 (450 ml), 80:1 (480 ml) and, after 1200 ml of mobile phase have been used, the first product fraction is obtained. All the product-containing fractions are combined and evaporated in a rotary evaporator, and the remaining solid residue is recrystallized from 15 ml of ethyl acetate. The crystals are filtered off with suction and dried at 40° C. under high vacuum. 2.47 g (5.66 mmol, 92%) of desired product are isolated as pale yellow-colored crystals.

Melting point: 162° C.

TLC (silica gel): R$_f$=0.42+0.46 (dichloromethane/methanol 9:1)

Analysis: C$_{19}$H$_{23}$N$_3$O$_9$ (437.40)

| | | | |
|---|---|---|---|
| calculated | C 52.17 | H 5.30 | N 9.60 |
| found | 51.71 | 5.47 | 9.20 |

UV (methanol): $\lambda_{max}$ [nm] (1 g ε): 265 (4.23)

$^1$H-NMR (250 MHz, d$_6$-DMSO, ppm): 11.36 (s, 1H, H—N(6)); 8.12 (d, 2H, o-H to NO$_2$(NPEE)); 7.92–7.88 (m, 1H, H—C(6)); 7.47 (d, 2H, m-H to NO$_2$(NPEE); 5.89–5.84 (m, 1H, H—C(1')); 5.65–5.62 (m, 1H, H—C(5)); 5.19–5.17 (m, 2H, HO—C(5')), HO—C(3')); 4.83–4.79 (m, 1H, CH(NPEE); 4.16–3.50 (m, 7H, H—C(2'), H—C(3'), H—C(4'), α-CH$_2$(NPEE), CH$_2$(5')); 2.90–2.80 (m, 2H, β-CH$_2$(NPEE)); 1.22–1,1,13 (m, 3H, CH$_3$(NPEE)

13.4 5'-O-(4,4'-Dimethoxytriphenylmethyl)-2'-O-[1-(4-nitrophenylethoxy)ethyl]-uridine 0.5 g (1.4 mmol) of 2'-O-[1-(4-nitrophenylethoxy)ethyl]-uridine are coevaporated 3× with 15 ml of absolute pyridine each time, the residue is subsequently dissolved in 60 ml of absolute pyridine, 0.46 g (0.37 mmol) of 4,4'-dimethoxytriphenylmethyl chloride is added, and the mixture is stirred at room temperature for 4 hours. The mixture is then diluted with 10 ml of methanol and stirred for a further 30 minutes at room temperature, the mixture is evaporated to half the volume in a rotary evaporator, taken up in dichloromethane and washed 2× with 80 ml of water each time. The aqueous phases are back-extracted with dichloromethane, all the organic phases are dried over sodium sulfate, filtered and evaporated in a rotary evaporator, and the residue is coevaporated several times with toluene. For purification, the crude product is loaded onto a silica gel column (4.0×25.0 cm) and chromatographed with toluene (100 ml), toluene/ethyl acetate 2:1 (450 ml), 1:1 (600 ml) and, after 550 ml of mobile phase have been used, the first product fraction is obtained, and all the fractions are subsequently collected, combined and evaporated in a rotary evaporator. The residue is dissolved in 4 ml of dichloromethane and added dropwise to 500 ml of petroleum ether, and the resulting precipitate is filtered off with suction and dried at 40° C. over paraffin shavings under high vacuum. 0.67 g (0.91 mmol, 80%) of compound is obtained as colorless amorphous solid.

Melting point: 136° C.

TLC (silica gel): $R_f$=0.44 (dichloromethane/methanol 15:1)

Analysis: $C_{40}H_{41}N_3O_{11}$ (739.78)

| | | | |
|---|---|---|---|
| calculated | C 64.94 | H 5.58 | N 5.68 |
| found | 65.31 | 6.09 | 5.10 |

UV (methanol) $\lambda_{max}$ [nm] (1 g ε): 204 (4.78); 233 (4.33); 266 (4.22)

$^1$H-NMR (250 MHz, $d_6$-DMSO, ppm): 11.4 (s, 1H, NH); 8.11 (d, 2H, o-H to $NO_2$(NPEE)); 7.74+7.71 (2d, 1H, H—C(6)); 7.48 (d, m-H to $NO_2$(NPEE); 7.38–7.22 (m, 9H, o-H to $OCH_3$, H(phenyl)); 6.88 (d, 4H, m-H to $OCH_3$); 5.85+5.81 (2d, 1H, H—C(1')); 5.32–5.21 (m, 2H, H—C(5), HO—C(3')); 4.91–4.87 (m, 1H), CH(NPEE); 4.24–4.12 (m, 2H, H—C(2'), H—C(3')); 3.96 (m, 1H, H—C(4')); 3.72–3.58 (m, 8H, $OCH_3$, α-$CH_2$(NPEE)); 3.32–3.19 (m, 2H, $CH_2$(5')); 2.89 (t, 2H, β-$CH_2$(NPEE)); 1.26–1.18 (m, 3H, $CH_3$(NPEE))

14. 5'-O-(4,4'-Dimethoxytriphenylmethyl)-2'-O-[1-(4-nitrophenylethoxy)ethyl]uridine-3'-O-(N,N-diisopropyl-2-cyanoethyl)phosphitamide Under a protective gas atmosphere, 0.5 g (0.67 mmol) of 5'-O-(4,4'-dimethoxytriphenylmethyl)-2'-O-[1-(4-nitrophenylethoxy)ethyl]uridine is dissolved in 10 ml of absolute, acid-free dichloromethane, 23.6 mg (0.33 mmol) of 1H-tetrazole and 0.407 g (1.35 mmol) of bis (diisopropylamino)(2-cyanoethoxy)phosphine are added, and the mixture is stirred under a nitrogen atmosphere at room temperature overnight. The reaction mixture is subsequently diluted with dichloromethane and extracted 2× by shaking with 30 ml of sodium chloride/sodium bicarbonate solution each time, the aqueous phases are back-extracted with dichloromethane, and all the organic phases are combined and then dried over sodium sulfate, filtered and evaporated in a rotary evaporator.

The crude product is loaded onto a silica gel column (3.3×14.0 cm) and eluted with toluene+0.5% $Et_3N$ (50 ml), toluene/ethyl acetate 2:1+0.5% $Et_3N$ (300 ml), 1:1+0.5% $Et_3N$ (100 ml) and, after 200 ml of mobile phase have been used, the first product fraction is obtained. All the product fractions are combined and evaporated in a rotary evaporator. The resulting oil is coevaporated several times with dichloromethane until a foam is formed. Drying under high vacuum results in 314.0 mg (0.33 mmol, 50%) as yellow-colored foam.

TLC (silica gel): $R_f$=0.46+0.55 (toluene/ethyl acetate 1:1)

Analysis: $C_{49}H_{58}N_5O_{12}P$ (940.0)

| | | | |
|---|---|---|---|
| calculated | C 62.61 | H 62.61 | N 7.45 |
| found | 62.42 | 6.29 | 7.49 |

UV (methanol): $\lambda_{max}$ [nm] (1 g ε): 202 (4.89); 234 (4.32); 265 (4.26)

$^1$H-NMR (250 MHz, $CDCl_3$, TMS, ppm): 9.39 (s, 1H, NH); 8.1 (d, 2H, o-H to $NO_2$(NPEE)); 8.09–7.93 (m, 1H, H—C(6)); 7.40–7.20 (m, 11H, m-H to $OCH_3$, H(phenyl), m-H to $NO_2$(NPEE)); 6.08–5.99 (m, 1H, H—C(1')); 5.29–5.25 (m, 1H, H—C(5)); 5.21–4.98 (m, 1H, CH(NPEE); 4.58–4.38 (m, 2H, H—C(2'), H—C(3')); 4.27–4.20 (m, 1H, H—C(4')); 4.09–3.44 (m, 14H, α-$CH_2$(NPEE), P—O—$CH_2$, $OCH_3$, $CH_2$(5'), N—CH); 2.98–2.90 (m, 2H, β-$CH_2$ (NPEE)); 2.64+2.43 (2t, 2H, $CH_2$—CN)); 1.40–1.14 (m, 15H, $CH_3$(NPEE), $C(CH_3)_2$)

$^{31}$P-NMR (161.70 MHz, $CDCl_3$, $H_3PO_4$, ppm): 151.24; 150.85; 150.75; 150.14

15. 5'-O-(4,4'-Dimethoxytriphenylmethyl)-2'-O-[1-(4-nitrophenylethoxy)ethyl]uridine-3'-O-(N,N-diisopropyl-2-(4-nitrophenyl)ethyl)phosphitamide 0.15 g (0.202 mmol) of 5'-O-(4,4'-dimethoxytriphenylmethyl)-2'-O-[1-(4-nitrophenylethoxy) ethyl]uridine, and 9.6 mg (0.137 mmol) of 1H-tetrazole are weighed into a flask flooded with nitrogen gas and dissolved in 4 ml of absolute acid-free dichloromethane, 0.21 g (0.547 mmol) of bis(diisopropylamino)-2-(4-nitrophenyl) ethoxyphosphine is added, and the mixture is stirred at room temperature under a nitrogen atmosphere overnight. It is subsequently evaporated in a rotary evaporator and, for purification, the crude product is loaded onto a silica gel column (3.0×10.0 cm). It is chromatographed with toluene (250 ml), toluene/ethyl acetate 3:1 (200 ml), 2:1 (600 ml) and, after 500 ml of mobile phase have been used, the first product fraction is obtained. All the fractions which contain product are combined and evaporated in a rotary evaporator. The residue is coevaporated several times with dichloromethane until a foam forms. Drying under high vacuum results in 0.125 g (0.12 mmol, 60%) of desired product in the form of a colorless foam.

TLC (silica gel): $R_f$=0.52 (toluene/ethyl acetate 1:1)

Analysis: $C_{54}H_{62}N_5O_{14}P$ (1036.09)

| | | | |
|---|---|---|---|
| calculated | C 62.60 | H 6.03 | N 6.75 |
| found | 62.55 | 6.15 | 6.48 |

UV (methanol): $\lambda_{max}$ [nm] (1 g ε): 202 (5.0); 235 (4.39); 267 (4.43)

$^1$H-NMR (250 MHz, $CDCl_3$, TMS, ppm): 8.72 (s, 1H, NH); 8.12–7.98 (m, 5H, H—C(6), o-H to $NO_2$(NPEE and NPE)); 7.41–7.21 (m, 13H, H(phenyl), m-H to $NO_2$(NPEE and NPE), m-H to $OCH_3$); 6.81 (d, 4H, o-H to $OCH_3$); 6.15–6.0 (m, 1H, H—C(1')); 5.27–5.18 (m, 1H, H—C(5));

5.01–4.89 (m, 1H, CH(NPEE); 4.37–4.03 (m, 3H, H—C(2'), H—C(3'), H—C(4')); 4.0–3.21 (m, 14H, α-CH$_2$(NPEE), OCH$_3$, P—O—CH$_2$, CH$_2$(5'), N—CH); 3.01–2.85 (m, 4H, CH$_2$—NO$_2$), β-CH$_2$(NPEE); 1.30–0.99 (m, 15H, CH$_3$ (NPEE), C(CH$_3$)$_2$)

$^{31}$P-NMR (161.70 MHz, CDCl$_3$, H$_3$PO$_4$, ppm): 150.04; 149.83; 149.39; 149.28

16.1 N$^4$-[2-(4-Nitrophenyl)ethoxycarbonyl]-2'-O-[1-(4-nitrophenylethoxy)ethyl]-3',5'-O-(1,1,3,3-tetraisopropyldisiloxane-1,3-diyl)cytidine 0.5 g (0.73 mmol) of N$^4$-[2-(4-nitrophenyl) ethoxycarbonyl]-3',5'-O-(1,1,3,3-tetraisopropyldisiloxane-1,3-diyl)cytidine are dissolved in 8 ml of absolute dichloromethane, 0.58 mg (3.05 μmol) of p-TsOH.H$_2$O is added, and the mixture is cooled in an ice bath to 0° C. Subsequently, 0.211 g (1.095 mmol) of 4-nitrophenyl vinyl ether is added, and the reaction solution is initially stirred in the cold bath and then allowed to warm slowly to room temperature. After 6 hours, the reaction solution is neutralized with 1.0N sodium methanolate/methanol solution and evaporated in a rotary evaporator.

For purification, the crude product is loaded onto a silica gel column (3.0×18.0 cm) and eluted with toluene (400 ml), toluene/ethyl acetate 5:1 (240 ml), 4:1 (500 ml), 3:1 (840 ml), 2:1 (500 ml) and, after 1300 ml of mobile phase have been used, the first product fraction is obtained. All fractions which contain the product are combined and evaporated in a rotary evaporator, and the resulting oil is coevaporated several times with dichloromethane. Drying of the colorless foam at 40° C. under high vacuum results in 0.53 g (0.607 mmol, 83%) of the desired product.

TLC (silica gel): R$_f$=0.27+0.44 (toluene/ethyl acetate 1:1)

Analysis: C$_{40}$H$_{57}$N$_5$O$_{13}$Si$_2$ (872.09)

| calculated | C 55.09 | N 6.58 | N 8.03 |
|---|---|---|---|
| found | 54.93 | 6.65 | 7.83 |

UV (methanol): λ$_{max}$ [nm] (1 g ε): 211 (4.53); 247 (4.33); 276 (4.36)

$^1$H-NMR (250 MHz, d$_6$-DMSO, ppm): 10.88 (s, 1H, NH); 8.16–8.02 (m, 5H, H—C(6), o-H to NO$_2$(NPEE and NPEOC), 7.61–7.48 (m, 4H, m-H to NO$_2$(NPEE and NPEOC)); 6.97 (d, 1H, H—C(5)); 5.67+5.69 (2s, 1H, H—C (1')); 5.05–4.92 (m, 1h, CH(NPEE)); 4.37–4.33 (m, 2H, α-CH$_2$(NPEOC)); 4.22–3.58 (m, 7H, H—C(2'), H—C(3'), H—C(4'); α-CH$_2$(NPEE), CH$_2$(5')); 3.09–2.90 (M, 4H, β-CH$_2$(NPEOC), β-CH$_2$(NPEE); 1.34+1.26 (2d, 3H, CH$_3$ (NPEE)); 1.03–0.77 (m, 28H, isopropyl).

16.2 N$^4$-[2-(4-Nitrophenyl)ethoxycarbonyl]-2'-O-[1-(4-nitrophenylethoxy)ethyl]-3',5'-O-(1,1,3,3-tetraisopropyldisiloxane-1,3-diyl)cytidine 1.0 g (1.47 mmol) of 2'-O-[1-(4-nitrophenylethoxy)ethyl]-3',5'-O-(1,1,3,3-tetraisopropyldisiloxane-1,3-diyl)cytidine (from Example 19) is dissolved in 20 ml of absolute dimethylformamide, 0.59 g (1.91 mmol) of 1-methyl-3-p-nitrophenylethoxycarbonylimidazolium chloride is added, and the mixture is stirred at room temperature for 3 hours. Subsequently the dimethylformamide is evaporated off in a rotary evaporator under high vacuum, the residue is taken up in dichloromethane, and the solution is extracted by shaking 2× with 50 ml of water each time and 1× with 50 ml of saturated sodium bicarbonate solution. All the aqueous phases are back-extracted with dichloromethane, and the combined organic phases are dried over sodium sulfate, filtered and evaporated in a rotary evaporator.

For purification, the residue is loaded onto a silica gel column (2.0×18.0 cm) and chromatographed with toluene (150 ml), toluene/ethyl acetate 4:1 (650 ml), 2:1 (150 ml), 1:1 (100 ml) and, after 500 ml of mobile phase have been used, the first product fraction is obtained. All product-containing fractions are combined and evaporated in a rotary evaporator, the remaining oil is coevaporated several times with dichloromethane, and the resulting colorless foam is subsequently dried at 40° C. under high vacuum. It is possible to isolate 1.23 g (1.41 mmol, 95%) of compound.

TLC (silica gel): R$_f$=0.27+0.44 (toluene/ethyl acetate 1:1)

C$_{40}$H$_{57}$N$_5$O$_{13}$Si$_2$ (872.09)

UV (methanol): λ$_{max}$ [nm] (1 g ε): 211 (4.53); 247 (4.33); 276 (4.36)

$^1$H-NMR (250 MHz, CDCl$_3$, TMS, ppm): 10.88 (s, 1H, NH); 8.16–8.02 (m, 5H, H—C(6), o-H to NO$_2$(NPEE and NPEOC), 7.61–7.48 (m, 4H, m-H to NO$_2$(NPEE and NPEOC)); 6.97 (d, 1H, H—C(5)); 5.67+5.69 (2s, 1H, H—C (1')); 5.05–4.92 (m, 1h, CH(NPEE)); 4.37–4.33 (m, 2H, α-CH$_2$(NPEOC)); 4.22–3.58 (m, 7E, H—C(2'), H—C(3'), H—C(4'); α-CH$_2$(NPEE), CH$_2$(5')); 3.09–2.90 (M, 4H, β-CH$_2$(NPEOC), β-CH$_2$(NPEE)); 1.34+1.26 (2d, 3H, CH$_3$ (NPEE)); 1.03–0.77 (m, 28H, isopropyl).

16.3 N$^4$-[2-(4-Nitrophenyl)ethoxycarbonyl]-2'-O-[1-(4-nitrophenylethoxy)ethyl]cytidine 2.0 g (2.95 mmol) of N$^4$-[2-(4-nitrophenyl) ethoxycarbonyl]-3',5'-O-(1,1,3,3-tetraisopropyldisiloxane-1,3-diyl)cytidine are dissolved in 30 ml of absolute dichloromethane, 2.36 mg (12.4 μmol) of 4-toluenesulfonic acid×H$_2$O are added, and the mixture is cooled in an ice bath to 0° C. To this mixture is added 0.85 g (4.42 mmol) of 4-nitrophenylethyl vinyl ether, and the reaction mixture is first stirred in the cold bath and subsequently allowed to warm slowly to room temperature. After 9 hours, the mixture is neutralized with 1.0N sodium methanolate/methanol solution and evaporated in a rotary evaporator. The remaining oil is dissolved in 7.0 ml of absolute tetrahydrofuran, 1.95 g (6.19 mmol) of tetrabutylammonium fluoride×3 H$_2$O and 0.5 ml of glacial acetic acid are added, and the mixture is stirred at room temperature for 4 hours and subsequently evaporated in a rotary evaporator.

For purification, the residue is loaded onto a silica gel column (3.5×15.0 cm) and chromatographed with dichloromethane (400 ml), dichloromethane/methanol 90:1 (270 ml), 50:1 (250 ml), 30:1 (500 ml), it being possible to obtain the first product fractions after 1100 ml of mobile phase have been used. All fractions which contain the product are combined and evaporated in a rotary evaporator. The residue is dissolved in 5 ml of dichloromethane and added dropwise to 150 ml of diethyl ether, and the resulting precipitate is filtered off with suction and dried at 40° C. under high vacuum. 1.25 g (1.98 mmol, 68%) of desired product are obtained in the form of a colorless amorphous solid.

TLC (silica gel): R$_f$=0.38+0.48 (dichloromethane/methanol 95:5)

Analysis: $C_{28}H_{31}N_5O_{12}$ (629.58)

|  | C | H | N |
|---|---|---|---|
| calculated | 53.41 | 4.96 | 11.12 |
| found | 53.46 | 5.13 | 10.89 |

UV (methanol): $\lambda_{max}$ [nm] (1 g ε): 212 (4.49); 2.47 (4.32); 275 (4.34)

$^1$H-NMR (250 MHz, d$_6$-DMSO, ppm): 10.79 (s, 1H, NH); 8.41–8.35 (m, 1H, H—C(6)); 8.15–8.05 (m, 4H, o-H to NO$_2$(NPEOC and NPE)); 7.60–7.42 (m, 4H, m-H to NO$_2$ (NPEOC and NPEE)); 6.95 (d, 1H, H—C(5)); 5.87–5.79 (2d, 1H, H—C(1')); 5.24–5.07 (m, 2H, HO—C(5'), HO—C (3')); 4.96+4.90 (2q, 1H, CH(NPEE)); 4.75 (t, 2H, α-CH$_2$ (NPEOC)); 4.10–3.67 (m,7H, H—C(2'), H—C(3'), H—C (4'), CH$_2$(5'), α-CH$_2$(NPEE)); 3.07 (t, 2H, β-CH$_2$(NPEOC)); 1.25+1.19 (2d, 3H, CH$_3$(NPEE))

16.4 N$^4$-[2-(4-Nitrophenyl)ethoxycarbonyl]-2'-O-[1-(4-nitrophenylethoxy)ethyl]cytidine 2.78 g (3.18 mmol) of N$^4$-[2-(4-nitrophenyl)ethoxycarbonyl]-2'-O-[1-(4-nitrophenylethoxy)ethyl]-3',5'-O-(1,1,3,3-tetraisopropyldisiloxane-1,3-diyl)cytidine are dissolved in 8.0 ml of absolute tetrahydrofuran, 2.51 g (7.97 mmol) of tetrabutylammonium fluoride×3 H$_2$O and 0.6 ml of glacial acetic acid are added, and the reaction solution is stirred at room temperature for 4 hours and subsequently evaporated in a rotary evaporator. For purification, the resulting oil is loaded onto a silica gel column (3.0×15.0 cm), eluting with dichloromethane (300 ml), dichloromethane/methanol 95:1 (380 ml), 90:1 (360 ml), 80:1 (240 ml), 70:1 (330 ml), 60:1 (900 ml), 55:1 (660 ml) and obtaining the first product-containing fraction after 1300 ml of mobile phase have been used. All fractions which contain product are combined and evaporated in a rotary evaporator, and the resulting residue is coevaporated several times with dichloromethane until a foam forms. Drying of the colorless foam at 40° C. under high vacuum results in 1.95 g (3.09 mmol, 97%) of desired product.

TLC (silica gel): R$_f$=0.38+0.48 (dichloromethane/methanol 95:5)

$C_{28}H_{31}N_5O_{12}$ (629.58)

Spectroscopic data are identical to Example 16.3

16.5 N$^4$-[2-(4-Nitrophenyl)ethoxycarbonyl]-2'-O-[1-(4-nitrophenylethoxy)ethyl]cytidine 0.5 g (1.14 mmol) of 2'-O-[1-(4-nitrophenylethoxy)ethyl]cytidine and 0.46 g (1.49 mmol) of 1-methyl-3-p-nitrophenylethoxycarbonylimidazolium chloride are dissolved in 10 ml of absolute dimethylformamide and stirred at room temperature for 3 hours. The dimethylformamide is subsequently evaporated off in a rotary evaporator under high vacuum, the residue is taken up in dichloromethane, and the solution is washed 2× with 30 ml of water each time and once with 30 ml of saturated sodium bicarbonate solution. All the aqueous phases are back-extracted with dichloromethane, and the combined organic phases are dried over sodium sulfate, filtered and evaporated in a rotary evaporator. For purification, the residue is loaded onto a silica gel column (3.0×17.0 cm) and eluted with dichloromethane (200 ml), dichloromethane/methanol 98:1 (100 ml), 96:1 (95 ml), 94:1 (190 ml), 92:1 (90 ml), 90:1 (360 ml), 85:1 (340 ml), 80:1 (160 ml), 76:1 (75 ml), 70:1 (70 ml), 60:1 (60 ml), 50:1 (100 ml), 40:1 (80 ml), 30:1 (180 ml), 25:1 (250 ml) and, after 1200 ml of mobile phase have been used, the first product fraction is obtained. All the fractions which contain product are combined and evaporated in a rotary evaporator, and the resulting residue is coevaporated several times with dichloromethane until a foam forms. Drying of the colorless foam at 40° C. under high vacuum results in 0.52 g (0.82 mmol, 73%) of compound.

TLC (silica gel): R$_f$=0.25+0.33 (dichloromethane/methanol 95:5)

$C_{28}H_{31}N_5O_{12}$ (629.58)

Spectroscopic data are identical to Example 16.3

16.6 5'-O-(4,4'-Dimethoxytriphenylmethyl)-N$^4$-[2-(4-nitrophenyl)ethoxycarbonyl]-2'-O-[1-(4-nitrophenylethoxy)ethyl]cytidine 1.95 g (3.09 mmol) of N$^4$-[2-(4-nitrophenyl)ethoxycarbonyl]-2'-O-[1-(4-nitrophenylethoxy)ethyl]cytidine are coevaporated 3× with 10 ml of absolute pyridine each time, the residue is dissolved in 60 ml of absolute pyridine, 1.36 g (4.02 mmol) of 4,4'-dimethoxytriphenylmethyl chloride are added, and the reaction solution is stirred at room temperature overnight. Subsequently 10 ml of methanol are added, the mixture is stirred at room temperature for a further 30 minutes and evaporated in a rotary evaporator, and the residue is coevaporated several times with toluene. For purification, the crude product is loaded onto a silica gel column (3.0×12.0 cm) and eluted with toluene (400 ml), toluene/ethyl acetate 3:1 (400 ml), 2:1 (1200 ml) and, after 850 ml of mobile phase have been used, the first product fraction is obtained. All fractions which contain product are combined and evaporated in a rotary evaporator. The residue is dissolved in 2 ml of dichloromethane and added dropwise to 250 ml of diethyl ether, and the precipitate is filtered off with suction and dried at 40° C. under high vacuum. 2.61 g (2.80 mmol, 91%) of compound are obtained in the form of a colorless amorphous solid.

TLC (silica gel): R$_f$=0.48 (toluene/ethyl acetate/methanol 5:4:1)

Analysis: $C_{49}H_{51}N_5O_{15}$x$H_2O$ (949.97)

|  | C | H | N |
|---|---|---|---|
| calculated | 61.95 | 5.19 | 7.37 |
| found | 61.42 | 5.35 | 7.09 |

UV (methanol): $\lambda_{max}$ [nm] (1 g ε): 211 (4.72); 236 (4.55); 274 (4.40)

$^1$H-NMR (250 MHz, d$_6$-DMSO, ppm): 10.71 (s, 1H, NH); 8.28–8.22 (m, 1H, H—C(6)); 8.16–8.06 (m, 4H, o-H to NO$_2$(NPEOC and NPEE)); 7.60–7.22 (m, 13H, m-H to NO$_2$(NPEOC and NPEE), H(phenyl), m-H to OCH$_3$)); 6.90–6.87 (m, 4H to OCH$_3$); 6.78–6.71 (m, 1H, H—C(5)); 5.75+5.74 (2s, 1H, H—C(1')); 5.41+5.19 (2d, 1H, HO—C (3')); 5.09+4.95 (2q, 1H, CH(NPEE)); 4.34 (t, 2H, α-CH$_2$ (NPEOC)); 4.28–3.63 (m, 13H, H—C(2'), H—C(3'), H—C (4'), α-CH$_2$(NPEE) OCH$_3$, CH$_2$(5')); 3.07 (t, 2H, β-CH$_2$ (NPEOC)); 2.92 (m, 2H, β-CH$_2$(NPEE)); 1.28+1.22 (2d, 3H, CH$_3$(NPEE))

17. 5'-O-(4,4'-Dimethoxytriphenylmethyl)-N$^4$-[2-(4-nitrophenyl)ethoxycarbonyl]-2'-O-[1-(4-nitrophenylethoxy)ethyl]cytidine-3'-O-(N,N-diisopropyl-2-cyanoethyl)phosphitamide 0.4 g (0.43 mmol) of 5'-O-(4,4'-dimethoxytriphenylmethyl)-N$^4$-[2-(4-nitrophenyl)ethoxycarbonyl]-2'-O-[1-(4-nitrophenylethoxy)ethyl]

cytidine and 18.0 mg (0.25 mmol) of 1H-tetrazole are weighed into a flask flooded with nitrogen gas, and the reactants are dissolved in 8 ml of absolute acetonitrile (residue analysis). Subsequently 0.31 g (1.03 mmol) of bis(diisopropylamino)(2-cyanoethoxy)phosphine is added, and the mixture is stirred at room temperature under a nitrogen atmosphere overnight. The reaction solution is then diluted with ethyl acetate and extracted by shaking 3× with 40 ml of sodium chloride/sodium bicarbonate solution each time, the aqueous phases are back-extracted with ethyl acetate, and all the organic phases are combined and subsequently dried over sodium sulfate, filtered and evaporated in a rotary evaporator. For purification, the oily residue is loaded onto a silica gel column (2.5×20.0 cm) and eluted with toluene (100 ml), toluene/ethyl acetate 3:1 (200 ml), 2:1 (750 ml), 1:1 (200 ml) and, after 450 ml of mobile phase have been used, the first product fraction is obtained. All product-containing fractions are combined and evaporated in a rotary evaporator, and the residue is coevaporated several times with ethyl acetate until a foam forms, and subsequently dried under high vacuum. 0.42 g (0.37 mmol, 86%) of compound is obtained in the form of a colorless foam.

TLC (silica gel): $R_f$=0.73+0.76 (toluene/ethyl acetate/methanol 5:4:1)

Analysis: $C_{58}H_{66}N_7O_{15}P$ (1132.18)

| | | | |
|---|---|---|---|
| calculated | C 61.53 | H 5.87 | N 8.65 |
| found | 60.88 | 6.24 | 8.50 |

UV (methanol): $\lambda_{max}$ [nm] (1 g ε): 203 (4.91); [214 (4.66)]; 235 (4.48); 275 (4.33)

$^1$H-NMR (250 MHz, CDCl$_3$, TMS, ppm): 8.58–8.49 (m, 1H, H—C(6)); 8.20–8.06 (m, 5H-o-H to NO$_2$(NPEE and NPEOC), NH); 7.42–7.21 (m, 13H, m-H to NO$_2$(NPEE and NPEOC), H(phenyl), m-H to OCH$_3$); 6.87–6.58 (m, 5H, o-H to OCH$_3$, H—C(5)); 6.10–5.91 (m, 1H—H—C(1')); 5.29–5.12 (m, 1H, CH(NPEE)); 4.49–4.39 (m, 2H, α-CH$_2$(NPEOC)); 4.32–4.10 (m, 3H, H—C(2'), H—C(3'), H—C(4')); 4.0–3.78 (m, 8H, α-CH$_2$(NPEE), OCH$_3$); 3.70–3.40 (m, 8H, P—O—CH$_2$, CH$_2$(5'), N—CH, β-CH$_2$(NPEOC)); 3.18–2.90 (m, 4H, CH$_2$—CN, β-CH$_2$(NPEE)); 1.33–0.92 (m, 15H, CH$_3$(NPEE), C(CH$_3$)$_2$)

$^{31}$P-NMR (161.70 MHz, CDCl$_3$, H$_3$PO$_4$, ppm): 151.63; 150.34; 150.22; 149.54

18. 5'-O-(4,4'-Dimethoxytriphenylmethyl)-N$^4$-[2-(4-nitrophenyl)ethoxycarbonyl]-2'-O-[1-(4-nitrophenylethoxy)ethyl]cytidine-3'-O-(N,N-diisopropyl-2-(4-nitrophenyl)ethyl)phosphitamide 0.4 g (0.43 mmol) of 5'-O-(4,4'-dimethoxytriphenylmethyl)-N$^4$-[2-(4-nitrophenyl) ethoxycarbonyl]-2'-O-[1-(4-nitrophenylethoxy)ethyl] cytidine and 20.31 mg (0.29 mmol) of 1H-tetrazole are weighed into a flask flooded with nitrogen gas and dissolved in 9 ml of absolute acetonitrile (residue analysis), 0.46 g (1.5 mmol) of bis(diisopropylamino)-2-(4-nitrophenyl) ethoxyphosphine is added, and the reaction solution is stirred under a protective gas atmosphere at room temperature overnight. It is then diluted with ethyl acetate and washed 3× with 40 ml of sodium chloride/ sodiumbicarbonate solution each time, the aqueous phases are back-extracted with ethyl acetate, and all the organic phases are combined and subsequently dried over sodium sulfate, filtered and evaporated in a rotary evaporator. For purification, the resulting oil is loaded onto a silica gel column (2.5×19.0 cm) and eluted with toluene (100 ml), toluene/ethyl acetate 4:1 (250 ml), 3:1 (1200 ml), it being possible to collect the first product fraction after 400 ml of mobile phase have been used. All fractions which contain product are combined and evaporated in a rotary evaporator, and the residue is coevaporated with ethyl acetate until a foam forms. Drying under high vacuum results in 0.48 g (0.39 mmol, 91%) in the form of a colorless foam.

TLC (silica gel): $R_f$=0.19+0.32+0.38 (toluene/ethyl acetate/methanol 5:4:1)

Analysis $C_{63}H_{70}N_7O_{12}P$ (1228.27)

| | | | |
|---|---|---|---|
| calculated | C 61.60 | H 5.74 | N 7.98 |
| found | 61.31 | 5.93 | 7.75 |

UV (methanol): $\lambda_{max}$ [nm] (1 g ε): 204 (5.0); [211 (4.85)]; 236 (4.57); 274 (4.57)

$^1$H-NMR (250 MHz, CDCl$_3$, TMS, ppm): 8.52–8.41 (m, 1H, H—C(6)); 8.20–7.97 (m, 7H, o-H to NO$_2$(NPEOC, NPEE and NPE), NH); 7.43–7.19 (m, 15H, m-H to NO$_2$ (NPEOC, NPEE and NPE), H(phenyl), m-H to OCH$_3$); 6.84–6.55 (m, 5H, o-H to OCH$_3$, H—C(5)); 6.02–5.90 (m, 1H, H—C(1')); 5.21–5.12 (m, 1H, CH(NPEE)); 4.44–4.42 (m, 2H, α-CH$_2$(NPEOC)); 4.25–4.13 (m, 3H, H—C(2'), H—C(3'), H—C(4')); 3.92–3.61 (m, 10H, P—O—CH$_2$, α-CH$_2$(NPEE), OCH$_3$); 3.51–3.39 (m, 4H, CH$_2$(5'), N—CH); 3.15–2.81 (m, 6H, β-CH$_2$(NPEE)); 1.34–1.02 (m, 15H, CH$_3$(NPEE), C(CH$_3$)$_2$)

$^{31}$P-NMR (161.70 MHz, CDCl$_3$, H$_3$PO$_4$, ppm): 150.28; 149.21; 148.97; 148.35

19.1 2'-O-[1-(4-Nitrophenylethoxy)ethyl]-3',5'-O-(1,1,3,3-tetraisopropyldisiloxane-1,3-diyl)cytidine 2.0 g (3.79 mmol) of N$^4$-acetyl-3',5'-O-(1,1,3,3-tetraisopropyldisiloxane-1,3-diyl)cytidine are dissolved in 40 ml of absolute dichloromethane, 0.31 g (1.64 mmol) of p-TsOH.H$_2$O and 1.09 g (5.68 mmol) of 4-nitrophenyl vinyl ether are added, and the mixture is stirred at room temperature for 2.½ hours and subsequently neutralized with 9.5N sodium methanolate/methanol solution and evaporated in a rotary evaporator. The residue is taken up in dichloromethane and extracted by shaking 3× with 70 ml of saturated sodium bicarbonate solution each time, all the aqueous phases are back-extracted with dichloromethane, and subsequently all the organic phases are combined and then dried over sodium sulfate, filtered and evaporated in a rotary evaporator. For purification, the crude product is loaded onto a silica gel column (3.5×21.0 cm). It is eluted with toluene (200 ml), toluene/ethyl acetate 1:1 (200 ml), 1:2 (600 ml), 1:3 (600 ml), 1:4 (250 ml), 1:5 (480 ml), 1:8 (180 ml), and the first fraction which contains product is obtained after 1500 ml of mobile phase have been used. All the product fractions are combined and evaporated in a rotary evaporator. The remaining oil is coevaporated several times with dichloromethane, and the resulting colorless foam is subsequently dried at 40° C. under high vacuum. 1.64 g (2.41 mmol, 64%) of the compound can be obtained.

TLC (silica gel): $R_f$=0.51 (toluene/ethyl acetate/methanol 5:4:1)

Analysis: $C_{31}H_{50}N_4O_9Si_2$ (678.93)

|  | C | H | N |
|---|---|---|---|
| calculated | 54.84 | 7.42 | 8.25 |
| found | 54.76 | 7.35 | 8.05 |

UV (methanol): $\lambda_{max}$[nm] (1 g $\epsilon$): 271 (4.27)

$^1$H-NMR (250 MHz, $d_6$-DMSO, ppm): 8.19–8.08 (m, 2H, o-H to NO$_2$(NPEE)); 7.71–7.57 (m, 1H, H—C(6)); 7.54–7.48 (m, 2H, m-H to NO$_2$(NPEE); 7.22 (s, 2H, NH$_2$); 5.06+5.04 (2q, 1H, CH(NPEE)); 4.19–3.60 (m, 7H, H—C (2'), H—C(3'), α-CH$_2$(NPEE), H—C(4'), CH$_2$(5')); 2.93–2.9 (m, 2H, β-CH$_2$(NPEE)); 1.32+1.25 (2d, 3H, CH$_3$(NPEE)); 1.02–0.78 (m, 28H, isopropyl)

19.2 2'-O-[1-(4-Nitrophenylethoxy)ethyl]cytidine 2.0 g (3.79 mmol) of N$^4$-acetyl-3',5'-O-(1,1,3,3-tetraisopropyldisiloxane-1,3-diyl)cytidine are dissolved in 40 ml of absolute dichloromethane, and 0.31 g (1.64 mmol) of p-TsOH.H$_2$O and 1.09 g (5.68 mmol) of 4-nitrophenylethyl vinyl ether are added to the reaction solution, and the mixture is stirred at room temperature for 2.½ hours, neutralized with 0.5N sodium methanolate/methanol solution and subsequently evaporated in a rotary evaporator. The residue is taken up in dichloromethane and extracted by shaking 3× with 70 ml of saturated sodium bicarbonate solution each time. All the aqueous phases are back-extracted with dichloromethane, and all the organic phases are combined, dried over sodium sulfate, filtered and evaporated in a rotary evaporator. The remaining residue is taken up in 3.0 ml of absolute tetrahydrofuran, and 2.87 g (9.09 mmol) of tetrabutylammonium fluoride×3 H$_2$O are added, and the mixture is stirred at room temperature for 20 minutes and subsequently evaporated in a rotary evaporator.

For purification, the resulting oil is loaded onto a silica gel column (3.7×17.0 cm) and eluted with dichloromethane (200 ml), dichloromethane/methanol 90:1 (270 ml), 80:1 (160 ml), 70:1 (140 ml), 50:1 (100 ml), 40:1 (80 ml), 20:1 (150 ml), 10:1 (440 ml), 9:1 (100 ml) and, after 1000 ml of mobile phase have been used, the first product-containing fraction is obtained. All the product fractions are combined and evaporated in a rotary evaporator, and the residue is recrystallized from 100 ml of dichloromethane. The precipitated solid is filtered off with suction and subsequently dried at 40° C. under high vacuum. 1.03 g (2.36 mmol, 62%) of colorless crystalline product which, despite recrystallization, is still contaminated with tetrabutylammonium fluoride are obtained.

Melting point: 145° C.

TLC (silica gel): $R_f$=0.34+0.4 (chloroform/methanol 1:1)

UV (methanol): $\lambda_{max}$ [nm] (1 g $\epsilon$): 271 (4.16)

$^1$H-NMR (250 MHz, $d_6$-DMSO, ppm): 8.10 (2d, 2H, o-H to NO$_2$(NPEE)), 7.88+7.85 (2d, 1H, H—C(6)); 7.49 (2d, 2H, m-H to NO$_2$(NPEE)); 7.28+7.20 (2s, 2H, NH$_2$); 5.89+5.82 (2d, 1H, H—C(1')); 5.72+5.70 (2d, 1H, H—C(5')); 5.20–4.99 (m, 2H, HO—C(5'), HO—C(3')); 4.35 (m, 1H, CH(NPEE)); 4.08–3.48 (m, 7H, H—C(2'), H—C(3'), H—C (4'), CH$_2$(5'), α-CH$_2$(NPEE)); 2.95–2.78 (m, 2H, β-CH$_2$ (NPEE); 1.18+1.14 (2d, 3H, CH$_3$(NPEE));

19.3 N$^4$-Acetyl-2'-O-[1-(4-nitrophenylethoxy)ethyl] cytidine 3.3 g (6.25 mmol) of N$^4$-acetyl-3',5'-O-(1,1,3,3-tetradiisopropyldisiloxane-1,3-diyl)cytidine are dissolved in 60 ml of absolute dichloromethane and cooled to 0° C. in an ice/salt bath, 0.51 g (2.70 mmol) of p-TsOH.H$_2$O and 1.80 g (9.37 mmol) of 4-nitrophenylethyl vinyl ether are added, and the mixture is stirred in the cold bath for 2 hours and subsequently extracted by shaking in a separating funnel 3× with 70 ml of saturated sodium bicarbonate solution each time. The aqueous phases are back-extracted with dichloromethane, and all the organic phases are combined, dried over sodium sulfate, filtered and evaporated in a rotary evaporator. The residue is dissolved in 14.0 ml of absolute tetrahydrofuran, 4.3 g (13.63 mmol) of tetrabutylammonium fluoride×3 H$_2$O are added, and the mixture is stirred at room temperature for 30 minutes and subsequently evaporated in a rotary evaporator.

For purification, the remaining oil is loaded onto a silica gel column (4.0×13.0 cm) and chromatographed with dichloromethane (600 ml), dichloromethane/methanol 95:1 (570 ml), 90:1 (810 ml), 85:1 (570 ml), 80:1 (480 ml), 70:1 (560 ml), 60:1 (480 ml), 55:1 (280 ml), 50:1 (500 ml), 45:1 (640 ml), 40:1 (980 ml) and, after 4000 ml of mobile phase have been used, the first product fraction is obtained. All the product-containing fractions are combined and evaporated in a rotary evaporator. The residue is dissolved in 3 ml of dichloromethane and added dropwise to 300 ml of diethyl ether, and the resulting precipitate is filtered off with suction and dried at 40° C. under high vacuum. 2.62 g (5.47 mmol, 88%) of the product are obtained in the form of a colorless amorphous solid.

Melting point: 157° C.

TLC (silica gel): $R_f$=0.56+0.63 (dichloromethane/methanol 9:1)

Analysis: $C_{21}H_{26}N_4O_9$ (478.46)

|  | C | H | N |
|---|---|---|---|
| calculated | 52.71 | 5.47 | 11.70 |
| found | 52.70 | 5.59 | 11.09 |

UV (methanol): $\lambda_{max}$ [nm] (1 g $\epsilon$): 212 (4.35); 250 (4.26); 279 (4.08)

$^1$H-NMR (250 MHz, $d_6$-DMSO, ppm): 10.89 (s, 1H, NH); 8.41 (t, 1H, H—C(6)); 8.12–8.02 (m, 2H, o-H to NO$_2$ (NPEE)); 7.47 (t, 2H, m-H to NO$_2$(NPEE)); 7.16 (d, 1H, H—C(5)); 5.88+5.79 (2d, 1H, H—C(1')); 5.18 (m, HO—C (5')); 5.08 (m, 1H, HO—C(3')); 4.99+4.91 (2q, 1H, CH(NPEE)); 4.10–3.57 (m, 7H, H—C(2'), H—C(3'), H—C (4'), CH$_2$(5'), α-CH$_2$(NPEE)); 2.92–2.83 (m, 2H, β-CH$_2$ (NPEE)); 2.08 (s, 3H, CH$_3$(acetyl)); 1.25+1.20 (2d, 3H, CH$_3$(NPEE));

19.4 N$^4$-Acetyl-5'-O-(4,4'-dimethoxytriphenylmethyl)-2'-O-[1-(4-nitrophenylethoxy)ethyl]cytidine 1.0 g (2.09 mmol) of N$^4$-acetyl-2'-O-[1-(4-nitrophenylethoxy)ethyl]cytidine are coevaporated 3× with 10 ml of absolute pyridine each time, the residue is taken up in 40 ml of absolute pyridine, 0.77 g (2.3 mmol) of 4,4'-dimethoxytriphenylmethyl chloride is added, and the mixture is stirred at room temperature overnight. The reaction mixture is then diluted with 10 ml of methanol, stirred at room temperature for a further 30 minutes, concentrated to half the volume, taken up in dichloromethane and extracted by shaking 2× with 50 ml of water each time. The aqueous phases are back-extracted with dichloromethane, all the organic phases are combined, dried over sodium sulfate, filtered and evaporated in a rotary evaporator, and the residue is coevaporated several times with toluene.

For purification, the remaining oil is loaded onto a silica gel column (3.2×23.0 cm) and chromatographed with dichloromethane (100 ml), dichloromethane/methanol 100:1 (200 ml), 98:1 (200 ml), 95:1 (480 ml), 90:1 (270 ml), 85:1 (250 ml), 80:1 (240 ml), 70:1 (140 ml), and the first product fraction is obtained after 1200 ml of mobile phase have been used. All the product-containing fractions are combined and evaporated in a rotary evaporator. The product is dissolved in 2 ml of dichloromethane and added dropwise to 250 ml of diethyl ether, and the resulting precipitate is filtered off with suction and dried at 40° C. under high vacuum. 1.29 g (1.65 mmol, 80%) of compound are obtained as a colorless amorphous solid.

Melting point: 160° C.

TLC (silica gel): $R_f$=0.48 (dichloromethane/methanol 15:1)

Analysis: $C_{42}H_{44}N_4O_{11}$ (780.83)

| calculated | C 64.60 | H 5.67 | N 7.17 |
|---|---|---|---|
| found | 64.85 | 6.00 | 6.87 |

UV (methanol) $\lambda_{max}$ [nm] (1 g ε): 204 (4.84); 236 (4.48); 274 (4.17), [296 (4.06)]

$^1$H-NMR (250 MHz, $d_6$-DMSO, ppm): 10.90 (s, 1H, NH); 8.34–8.24 (m, 1H, H—C(6)); 8.09' (d, 2H-o-H to $NO_2$ (NPEE)); 7.52–7.23 (m, 11H, m-H to $NO_2$(NPEE), H(phenyl), m-H to $OCH_3$); 6.98–6.95 (m, 1H, H—C(5)); 6.90–6.87 (m-4H, o-H to $OCH_3$); 5.88+5.76 (2s, 1H, H—C(1')); 5.25–5.15 (m, 1H, HO—C(3')); 5.08+4.95 (2q, 1E, CH(NPEE)); 4.27–3.97 (m, 3H, H—C(2'), H—C(3'), H—C(4')); 3.89–3.68 (m, 10H, $CH_2$(5'), α-$CH_2$(NPEE), $OCH_3$); 2.92 (m, 2H, β-$CH_2$(NPEE)); 2.08 (s, 3H, $CH_3$(acetyl)); 1.29–1.22 (m, 3H, $CH_3$(NPEE))

20.1 $N^6$-[2-(4-Nitrophenyl)ethoxycarbonyl]-2'-O-[1-(4-nitrophenylethoxy)ethyl]-3',5'-O-(1,1,3,3-tetraisopropyldisiloxane-1,3-diyl)adenosine 0.5 g (0.711 mmol) of $N^6$-[2-(4-nitrophenyl) ethoxycarbonyl]-3',5'-O-(1,1,3,3-tetraisopropyldisiloxane-1,3-diyl)adenosine is dissolved in 9 ml of absolute dichloromethane, 9.56 mg (2.94 μmol) of p-TsOH.$H_2O$ are added, and the mixture is cooled in an ice bath to 0° C. Subsequently 0.20 g (1.06 mmol) of 4-nitrophenylethyl vinyl ether is added, and the reaction solution is stirred initially in an ice bath and is subsequently allowed to warm to room temperature and is stirred overnight. It is extracted by shaking 3× with 50 ml of saturated sodium bicarbonate solution each time. The aqueous phases are back-extracted with dichloromethane, and all the organic phases are combined, dried over sodium sulfate, filtered and evaporated in a rotary evaporator.

For purification, the crude product is loaded onto a silica gel column (3.5×14.0 cm) and chromatographed with toluene (500 ml), toluene/ethyl acetate 5:1 (300 ml), 4:1 (500 ml), 3:1 (800 ml), 2:1 (500 ml) and, after 1400 ml of mobile phase have been used, the first product fraction is obtained, and all the fractions are collected in sequence and evaporated in a rotary evaporator. The residue is coevaporated several times with dichloromethane until a foam forms. Drying of the colorless foam at 40° C. under high vacuum results in 0.412 g (0.46 mmol, 65%) of the desired product.

TLC (silica gel): $R_f$=0.39 (toluene/ethyl acetate 1:1)
Analysis: $C_{41}H_{57}N_7O_{12}Si_2$ (896.12)

| calculated: | C 54.95 | H 6.41 | N 10.94 |
|---|---|---|---|
| found: | 54.71 | 6.48 | 10.62 |

UV (methanol): $\lambda_{max}$ [nm] (1 g ε): 203 (4.93); 267 (4.58); [276 (4.51)]

$^1$H-NMR (250 MHz, $CDCl_3$, TMS, ppm): 8.69+8.61 (2s, 1H, H—C(8)); 8.30+8.22 (2s, 1H, H—C(2)); 8.21 (s, 1H, NH); 8.15 (d, 2H, o-H to $NO_2$(NPEOC)); 8.05+7.99 (2d, 2H, o-H to $NO_2$(NPEE); 7.43–7.29 (m, 4H, m-H to $NO_2$ (NPEOC and NPEE)); 6.02+6.0 (2s, 1H, H—C(1')); 5.06+ 5.01 (2q, 1H, CH(NPEE)); 4.57–3.68 (m, 9H, H—C(2'), α-$CH_2$(NPEOC), H—C(3'), α-$CH_2$(NPEE), H—C(4'), $CH_2$ (5')); 3.13 (t, 2H, β-$CH_2$(NPEOC); 2.98–2.90 (m, 2H, β-$CH_2$(NPEE)); 1.45+1.38 (2d, 3H, $CH_3$(NPEE)); 1.07–0.84 (m, 28H, isopropyl)

20.2 $N^6$-[2-(4-Nitrophenyl)ethoxycarbonyl]-2'-O-[1-(4-nitrophenylethoxy)ethyl]adenosine 0.3 g (0.334 mmol) of $N^6$-[2-(4-nitrophenyl) ethoxycarbonyl]-3',5'-O-(1,1,3,3-tetraisopropyldisiloxane-1,3-diyl)-2'-O-1-(p-nitrophenylethoxy)ethyladenosine is dissolved in 1.0 ml of absolute tetrahydrofuran, 0.26 g (0.836 mmol) of tetrabutylammonium fluoride×3 $H_2O$ and 0.09 ml (1.67 mmol) of glacial acetic acid are added, and the mixture is stirred at room temperature for 4 hours and subsequently evaporated in a rotary evaporator.

For purification, the residue is loaded onto a silica gel column (3.0×12.0 cm) and eluted with dichloromethane (400 ml), dichloromethane/methanol 95:1 (670 ml), 90:1 (360 ml), 85:1 (340 ml), 80:1 (240 ml), 75:1 (750 ml), 70:1 (700 ml), 65:1 (650 ml), 60:1 (610 ml) and, after 2200 ml of mobile phase have been used, the first product fraction is obtained. All the product-containing fractions are combined and evaporated in a rotary evaporator, and the residue is coevaporated several times with dichloromethane until a foam forms. Drying of the colorless foam at 40° C. under high vacuum allows 0.201 g (0.307 mmol, 92%) of compound to be isolated.

TLC (silica gel): $R_f$=0.5+0.57 (dichloromethane/methanol 95:5)

Analysis: $C_{29}H_{31}N_7O_{11}×½ H_2O$ (662.61)

| calculated | C 52.56 | H 4.86 | N 14.79 |
|---|---|---|---|
| found | 52.41 | 4.98 | 14.52 |

UV (methanol): $\lambda_{max}$ [nm] (1 g ε): 212 (4.55); 267 (4.54); [273 (4.40)]

$^1$H-NMR (250 MHz, $d_6$-DMSO, ppm): 10.65+10.63 (2s, 1H, NH); 8.72+8.69 (2s, 1H, H—C(8)); 8.61+8.59 (2s, 1H, H—C(2)); 8.13 (d, 2H, o-H to $NO_2$(NPEOC)); 8.03 (d, 2H, o-H to $NO_2$(NPEE)); 7.61 (d, 2H, m-H to $NO_2$(NPEOC)); 7.24+7.23 (2d, 2H, m-H to $NO_2$(NPEE)); 6.11+6.08 (2s, 1H, H—C(1')); 5.24 (m, 2H, HO—C(5'), HO—C(3')); 4.81–4.74 (m, 2H, CH(NPEE), H—C(2')); 4.38 (t, 2H, α-$CH_2$ (NPEOC)); 4.38–4.26 (m, 1H, H—C(3')); 3.99 (m, 1H, H—C(4')); 3.72–3.42 (m, 4H, $CH_2$(5'), α-$CH_2$(NPEE)); 3.10 (t, 2H, β-$CH_2$(NPEOC)); 2.63–2.49 (m, 2H, β-$CH_2$ (NPE)); 1.18+1.10 (2d, 3H, $CH_3$(NPEE))

20.3 $N^6$-[2-(4-Nitrophenyl)ethoxycarbonyl]-2'-O-[1-(4-nitrophenyl)ethyl]adenosine 0.5 g (0.711 mmol) of $N^6$-[2-(4-nitrophenyl) ethoxycarbonyl)-3',5'-O-(1,1,3,3-tetraisopropyldisiloxane- 1,3-diyl)adenosine is dissolved in 9 ml of absolute dichloromethane, 0.56 mg (2.94 μmol) of p-TsOH.H₂O is added, and the mixture is cooled in an ice bath to 0° C. To this solution is added 0.20 g (1.06 mmol) of 4-nitrophenylethyl vinyl ether, and the reaction mixture is first stirred in the ice bath and allowed to warm slowly to room temperature and then stirred overnight. It is extracted by shaking 3× with 50 ml of saturated sodium bicarbonate solution each time, all the aqueous phases are back-extracted with dichloromethane, and the combined organic phases are dried over sodium sulfate and evaporated in a rotary evaporator. The residue is dissolved in 1.8 ml of absolute tetrahydrofuran, 0.56 g (1.778 mmol) of tetrabutylammonium fluoride·3 H₂O and 0.2 ml (3.55 mmol) of glacial acetic acid are added, and the mixture is stirred at room temperature for 4 hours and subsequently evaporated in a rotary evaporator.

For purification, the resulting oil is loaded onto a silica gel column (3.0×10.9 cm) and eluted with dichloromethane (500 ml), dichloromethane/methanol 95:1 (485 ml), 80:1 (410 ml), 70:1 (710 ml), 65:1 (650 ml) and, after 1450 ml of mobile phase have been used, the first fraction which contains product is obtained, and all the following product fractions are combined and evaporated in a rotary evaporator. The residue is coevaporated several times with dichloromethane until a foam forms and subsequently dried at 40° C. under high vacuum. 0.31 g (0.474 mmol, 67%) of desired product is obtained in the form of a colorless foam.

TLC (silica gel): $R_f$=0.5+0.57 (dichloromethane/methanol 95:5)

$C_{29}H_{31}N_7O_{11} \times \frac{1}{2} H_2O$ (662.61)

Spectroscopic data are identical to Example 20.2

20.4 5'-O-(4,4'-Dimethoxytriphenylmethyl)-N⁶-[2-(4-nitrophenyl)ethoxycarbonyl]-2'-O-[1-(4-nitrophenylethoxy)ethyl]adenosine 0.5 g (0.76 mmol) of N⁶-[2-(4-nitrophenyl)ethoxycarbonyl]-2'-O-[1-(4-nitrophenylethoxy)ethyl]adenosine is coevaporated 3× with 10 ml of absolute pyridine each time, the residue is dissolved in 30 ml of absolute pyridine, 0.36 g (1.07 mmol) of 4,4'-dimethoxytriphenylmethyl chloride is added, and the mixture is stirred at room temperature overnight. It is subsequently diluted with ethyl acetate and extracted by shaking 3× with saturated sodium bicarbonate solution each time. The aqueous phases are back-extracted with ethyl acetate, all the organic phases are combined, dried over sodium sulfate, filtered and evaporated in a rotary evaporator, and the residue is coevaporated several times with toluene.

For purification, the crude product is loaded onto a silica gel column (3.0×16.0 cm) and eluted with toluene (200 ml), toluene/ethyl acetate 3:1 (400 ml), 2:1 (300 ml), 1:1 (400 ml), 1:2 (600 ml) and, after 1100 ml of mobile phase have been used, the first product fraction is obtained. All the product-containing fractions are combined and evaporated in a rotary evaporator. The resulting residue is dissolved in 3 ml of ethyl acetate and added dropwise to 75 ml of n-hexane, and the resulting precipitate is filtered off with suction and dried at 40° C. under high vacuum over paraffin shavings. 0.7 g (0.73 mmol, 96%) of compound is obtained in the form of a colorless amorphous solid.

TLC (silica gel): $R_f$=0.44 (toluene/ethyl acetate/methanol 5:4:1)

Analysis: $C_{50}H_{49}N_7O_{13}$ (955.98)

| | | | |
|---|---|---|---|
| calculated | C 62.82 | H 5.16 | N 10.25 |
| found | 62.28 | 5.26 | 10.23 |

UV (methanol): $\lambda_{max}$ [nm] (1 g ε): 202 (5.01); 236 (4.42); 267 (4.59); [275 (4.52)]

¹H-NMR (250 MHz, d₆-DMSO, ppm): 10.55 (s, 1H, NH); 8.55–8.49 (m, 2H, H—C(8), H—C(2)); 8.13 (d, 2H, o-H to NO₂(NPEOC)); 8.03–7.97 (m, 2H, o-H to NO₂(NPEE); 7.60 (d, 2H, m-H to NO₂(NPEOC)); 7.37–7.20 (m, 11H, m-H to NO₂(NPEE), H(phenyl), m-H to OCH₃); 6.48–6.78 (m, 4H, o-H to OCH₃); 6.13–6.11 (m, 1H, H—C(1')); 5.28–5.26 (m, 1H, HO—C(3')); 4.94–4.87 (m, 1H, CH(NPEE)); 4.85–4.78 (m, 1H, H—C(2')); 4.41–4.36 (m, 3H, α-CH₂(NPEOC), H—C(3')); 4.12–4.10 (m, 1H, H—C(4')); 3.70 (s, 6H, OCH₃); 3.62–3.39 (m, 2H, CH₂(5')); 3.10 (t, 2H, β-CH₂(NPEOC)); 2.64–2.52 (m, 2H, β-CH₂(NPEE)); 1.20+1.13 (2d, 3H, CH₃(NPEE))

21. 5'-O-(4,4'-Dimethoxytriphenylmethyl)-N⁶-[2-(4-nitrophenyl)ethoxycarbonyl]-2'-O-[1-(4-nitrophenylethoxy)ethyl]adenosine-3'-O-(N,N-diisopropyl-2-cyanoethyl)phosphitamide 0.4 g (0.46 mmol) of 5'-O-(4,4'-dimethoxytriphenylmethyl)-N⁶-[2-(4-nitrophenyl)ethoxycarbonyl]-2'-O-[1-(4-nitrophenylethoxy)ethyl]adenosine is weighed together with 21.8 mg (0.31 mmol) of 1H-tetrazole into a flask which is flooded with nitrogen gas, and dissolved in 8 ml of absolute acetonitrile (residue analysis) and subsequently 0.37 g (1.24 mmol) of bis(diisopropylamino)-(2-cyanoethoxy)phosphine is added. The reaction solution is stirred under a protective gas atmosphere at room temperature overnight, diluted with ethyl acetate and washed 3× with 40 ml of sodium chloride/sodium bicarbonate solution each time. All the aqueous phases are back-extracted with ethyl acetate, and the combined organic phases are dried over sodium sulfate, filtered and evaporated in a rotary evaporator.

For purification, the residue is loaded onto a silica gel column (2.5×18.0 cm) and chromatographed with toluene/ethyl acetate 3:1 (400 ml), 2:1 (600 ml) and, after 550 ml of mobile phase have been used, the first product fraction is obtained, and all subsequent fractions are combined and evaporated in a rotary evaporator. Coevaporation of the residue with ethyl acetate and subsequent drying of the colorless foam under high vacuum results in 0.45 g (0.39 mmol, 85%) of compound.

TLC (silica gel): $R_f$=0.14+0.23 (toluene/ethyl acetate 1:1)

Analysis: $C_{59}H_{66}N_9O_{14}P$ (1156.20)

| | | | |
|---|---|---|---|
| calculated | C 61.29 | H 5.75 | N 10.90 |
| found | 60.61 | 6.01 | 10.76 |

UV (methanol): $\lambda_{max}$ [nm] (1 g ε): 204 (4.98); 236 (4.47); 226 (4.56); [276 (4.48)]

¹H-NMR (250 MHz, CDCl₃, TMS, ppm): 8.66–8.63 (m, 1H, H—C(8)); 8.21–7.98 (m, 6H, H—C(2), o-H to NO₂ (NPEOC and NPEE), NH); 7.46–7.11 (m, 13H, m-H to NO₂(NPEE and NPEOC), H-phenyl, m-H to OCH₃); 6.83–6.76 (m, 4H, o-H to OCH₃); 6.21–6.11 (m, 1H, H—C(1')); 5.23–5.08 (m, 1H, H—C(2')); 4.98–4.73 (m, 1H, CH(NPEE)); 4.61–4.50 (m, 3H, α-CH$_2$(NPEOC), H—C(3'));
4.41–4.28 (m, 1H, H—C(4')); 3.93–3.16 (m, 8H, OCH$_3$,
α-CH$_2$(NPEE)); 3.76–3.42 (m, 4H, P—O—CH$_2$, CH$_2$(5'));
3.45–3.27 (m, 2H, n—CH); 3.16 (t, 2H, β-CH$_2$(NPEOC));
2.72–2.57 (m, 4H, β-CH$_2$—CN), CH$_2$—CN); 1.35–1.15 (m, 15H, CH$_3$(NPEE), C(CH$_3$)$_2$)

$^{31}$P-NMR (161.70 MHz, CDCl$_3$, H$_3$PO$_4$, ppm): 151.56; 150.98; 150.79; 150.53

22. 5'-O-(4,4'-Dimethoxytriphenylmethyl)-N$^6$-[2-(4-nitrophenyl)ethoxycarbonyl]-2'-O-[1-(4-nitrophenylethoxy)ethyl]adenosine-3'-O-(N,N-diisopropyl-2-(4-nitrophenyl)ethyl)phosphitamide 0.4 g (0.41 mmol) of 5'-O-(4,4'-dimethoxytriphenylmethyl)-N$^6$-[2-(4-nitrophenyl) ethoxycarbonyl]-2'-O-[1-(4-nitrophenylethoxy)ethyl] adenosine is weighed together with 19.78 mg (0.282 mmol) of 1H-tetrazole into a flask which is flooded with nitrogen gas, and dissolved in 9 ml of absolute acetonitrile (residue analysis) and subsequently 0.45 g (1.13 mmol) of bis (diisopropylamino)-2-(4-nitrophenyl)ethoxyphosphine is added. The reaction solution is stirred under a protective gas atmosphere at room temperature overnight, diluted with ethyl acetate and washed 3× with 40 ml of sodium chloride/sodium bicarbonate solution each time. All the aqueous phases are back-extracted with ethyl acetate, and the combined organic phases are dried over sodium sulfate, filtered and evaporated in a rotary evaporator.

For purification, the crude product is loaded onto a silica gel column (2.5×18.0 cm) and eluted with toluene (100 ml), toluene/ethyl acetate 5:1 (300 ml), 4:1 (300 ml), 3:1 (400 ml), 2:1 (300 ml), it being possible to collect the first product fraction after 700 ml of mobile phase have been used. All the product-containing fractions are combined and evaporated in a rotary evaporator, and the resulting residue is coevaporated several times with ethyl acetate, and the resulting colorless foam is dried under high vacuum. It is possible to isolate 0.431 g (0.33 mmol, 80%) of the desired compound.

TLC (silica gel): R$_f$=0.26+0.30 (toluene/ethyl acetate 1:1)
Analysis: C$_{64}$H$_{70}$N$_9$O$_{16}$P (1252.29)

|  | C | H | N |
|---|---|---|---|
| calculated | 61.38 | 5.68 | 10.06 |
| found | 60.81 | 5.82 | 9.54 |

UV (methanol): λ$_{max}$ [nm] (1 g ε): 207 (5.23); [214 (5.09)]; 269 (4.70)

$^1$H-NMR (250 MHz, CDCl$_3$, TMS, ppm): 8.66–8.60 (m, 1H, H—C(8)); 8.19–7.96 (m, (H, H—C(2), o-H to NO$_2$ (NPEOC, NPE and NPEE), NH); 7.44–7.07 (m, 15H, m-H to NO$_2$(NPEE and NPEOC), H(phenyl), m-H to OCH$_3$); 6.76+6.75 (2d, 4H, o-H to OCH$_3$); 6.25–6.08 (m, 1H, H—C(1')); 5.21–4.68 (m, 2H, H—C(2') CH(NPEE)); 4.54–4.42 (m, 3H, H—C(3'), α-CH$_2$(NPEOC)); 4.38–4.28 (m, 1H, H—C(4')); 4.0–3.70 (m, 8H, α-CH$_2$(NPEE), OCH$_3$); 3.60–3.40 (m, 4H, P—O—CH$_2$(5')); 3.35–3.22 (m, 2H, N—CH); 3.14 (t, 2H, CH$_2$(NPEOC)); 3.05–2.52 (m, 4H, β-CH$_2$(NPEE), β-CH$_2$(NPE); 1.29–0.97 (m, 15H, CH$_3$ (NPEE), C(CH$_3$)$_2$)

$^{31}$P-NMR (161.70 MHz, CDCl$_3$, H$_3$PO$_4$, ppm): 150.58; 149.89; 149.32; 149.25

23.1 N$^6$-Benzoyl-2'-O-[1-(4-nitrophenyl)ethoxy]-3', 5'-O-(1,1,3,3-tetraisopropyldisiloxane-1,3-diyl) adenosine 1.0 g (1.63 mmol) of N$^6$-benzoyl-3',5'-O-(1,1,3,3-tetraisopropyldisiloxane-1,3-diyl)adenosine is dissolved in 16 ml of absolute dichloromethane, 32.6 mg (0.17 mmol) of p-TsOH.H$_2$O and 0.46 g (2.4 mmol) of 4-nitrophenylethyl vinyl ether are added, and the mixture is stirred at room temperature for 1½ hours, neutralized with 0.5N sodium methanolate/methanol solution and evaporated in a rotary evaporator. The residue is taken up in dichloromethane and extracted 3× with 50 ml of saturated sodium bicarbonate solution each time. All the aqueous phases are back-extracted with dichloromethane, and the combined organic phases are dried over sodium sulfate, filtered and evaporated in a rotary evaporator. For purification, the crude product is loaded onto a silica gel column (83.5×16.0 cm), chromatographing with toluene (200 ml), toluene/ethyl acetate 4:1 (400 ml), 3:1 (600 ml), 2:1 (500 ml), it being possible to collect the first product fraction after 500 ml of mobile phase have been used. All the fractions which contain product are combined and evaporated in a rotary evaporator, and the residue is coevaporated several times with dichloromethane until a foam forms. Drying of the pale yellow-colored foam at 40° C. under high vacuum results in 1.0 g (1.24 mmol, 76%) of compound.

TLC (silica gel): R$_f$=0.40 (toluene/ethyl acetate 1:1)
Analysis: C$_{39}$H$_{54}$N$_6$O$_9$Si$_2$ (807.07)

|  | C | H | N |
|---|---|---|---|
| calculated | 58.04 | 6.74 | 10.41 |
| found | 58.05 | 6.78 | 10.26 |

UV (methanol): λ [nm] (1 g ε): 276 (4.41)

$^1$H-NMR (250 MHz, CDCl$_3$, TMS, ppm): 9.01 (s, 1H, NH); 8.71+8.63 (2s, 1H, H—C(8)); 8.27+8.20 (2s, 1H, H—C(2)); 8.10–7.94 (m, 4H, o-H to NO$_2$(NPEE), o-H (benzoyl); 7.57–7.07 (m, 5H, m-H to NO$_2$(NPEE), m- and p-H(benzoyl)); 6.01–5.99 (2s, 1H, H—C(1')); 5.06–4.97 (m, 1H, CH(NPEE)); 4.60–4.49 (m, 1H, H—C(2')); 4.40–4.32 (m, 1H, H—C(3')); 4.23–3.64 (m, 5H, H—C(4'), CH$_2$(5'), α-CH$_2$(NPEE)); 2.97–2.86 (m, 2H, β-CH$_2$(NPEE)), 1.41+1.34 (2d, 3H, CH$_3$(NPEE)); 1.02–0.88 (m, 28H, isopropyl)

23.2 N$^6$-Benzoyl-2'-O-[1-(4-nitrophenylethoxy) ethyl]adenosine 2.0 g (3.25 mmol) of N$^6$-benzoyl-3',5'-O-(1,1,3,3-tetraisopropyldisiloxane-1,3-diyl)adenosine are dissolved in 40 ml of absolute dichloromethane, 5.6 mg (29.4 µmol) of p-TsOH.H$_2$O are added, and the mixture is cooled to 0° C. in an ice bath. To this solution are added 2.0 g (10.6 mmol) of 4-nitrophenylethyl vinyl ether, and the reaction mixture is first stirred in the ice bath and allowed to warm slowly to room temperature, and after 1½ hours the reaction mixture is neutralized with 0.5N sodium methanolate/methanol solution and evaporated in a rotary evaporator. The residue is taken up in dichloromethane and extracted by shaking 3× with 60 ml of saturated sodium bicarbonate solution each time. All the aqueous phases are back-extracted with dichloromethane, and the combined organic phases are dried over sodium sulfate and evaporated in a rotary evaporator. The residue is dissolved in 8.0 ml of absolute tetrahydrofuran, 2.46 g (7.82 mmol) of tetrabutylammonium fluoride·3H$_2$O are added, and the mixture is stirred at room temperature for 30 minutes and then evaporated in a rotary evaporator. For purification, the resulting oil is loaded onto a silica gel column (3.0×17.0 cm) and eluted with dichloromethane (200 ml), dichloromethane/methanol 50:1 (200 ml), 45:1 (370 ml), 40:1 (140 ml), 35:1 (180 ml) and, after 550 ml of mobile phase have been used, the first fraction which contains product is obtained, and all the following product fractions are combined and evaporated in a rotary evaporator. The residue is dissolved in 2 ml of dichloromethane and added dropwise to 250 ml of diethyl ether, and the resulting colorless precipitate is filtered off with suction and subsequently dried at 40° C. under high vacuum. 1.26 g (2.23 mmol, 68%) of desired product are obtained in the form of a colorless amorphous solid.

Melting point: 170° C.

TLC (silica gel): $R_f$=0.54+0.60 (dichloromethane/methanol 9:1)

Analysis: $C_{27}H_{28}N_6O_8$ (653.61)

| | | | |
|---|---|---|---|
| calculated | C 57.44 | H 4.99 | N 14.88 |
| found | 57.06 | 5.26 | 14.62 |

UV (methanol): $\lambda_{max}$ [nm] (1 g ε): 277 (4.44)

$^1$H-NMR (250 MHz, d$_6$-DMSO, ppm): 11.23 (s, 1H, NH); 8.75+8.74 (2s, 1H, H—C(8)); 8.72+8.71 (2s, 1H, H—C(2)); 8.08–8.01 (m, 4H, o-H to NO$_2$(NPEE), o-H(benzoyl)); 7.64–7.51 (m, 3H, m- and p-H(benzoyl)); 7.31–7.28 (2d, 2H, m-H to NO$_2$ (NPEE)); 6.15 (d, 1H, H—C(1')); 6.15 (d, 1H, H—C(1')); 5.37–5.13 (m, 2H, HO—C (5'), HO—C(3')); 4.93–4.72 (m, 2H, CH(NPEE), H—C(2')); 4.35–4.17 (m, 1H, H-(3')); 4.0 (m, 1H, H—C(4')); 3.79–3.40 (m, 4H, CH$_2$(5'), α-CH$_2$(NPEE)); 2.68–2.60 (m, 2H, β-CH$_2$(NPEE)); 1.18+1.134 (2d, 3H, CH$_3$ (NPEE))

23.3 N$^6$-Benzoyl-5'-O-(4,4'-dimethoxytriphenylmethyl)-2'-O-[1-(4-nitrophenylethoxy)ethyl]adenosine 0.9 g (1.59 mmol) of N6-benzoyl-2'-O-[1-(4-nitrophenylethoxy)ethyl]adenosine is coevaporated 3 x with 10 ml of absolute pyridine each time, the residue is dissolved in 40 ml of absolute pyridine, 0.59 g (1.75 mmol) of 4,4'-dimethoxytriphenylmethyl chloride is added, and the reaction solution is stirred at room temperature overnight. Subsequently 10 ml of methanol are added, the mixture is stirred at room temperature for a further 30 minutes, concentrated to half the volume, taken up in dichloromethane and extracted by shaking 2 x with 50 ml of water each time. The aqueous phase is back-extracted with dichloromethane, all the organic phases are combined, dried over sodium sulfate, filtered and evaporated in a rotary evaporator, and the residue is coevaporated several times with toluene.

For purification, the crude product is loaded onto a silica gel column (3.2×17.0 cm) and eluted with toluene (100 ml), toluene/ethyl acetate 2:1 (600 ml), 1:1 (300 ml), 1:2 (900 ml), 1:3 (400 ml) and, after 1100 ml of mobile phase have been used, the first product-containing fraction is obtained, and all subsequent fractions are combined and evaporated in a rotary evaporator. The residue is dissolved in 2 ml of dichloromethane and added dropwise to 200 ml of diethyl ether, and the resulting precipitate is filtered off with suction and subsequently dried at 40° C. under high vacuum. 1.1 g (1.27 mmol, 80%) of desired product are obtained as a colorless amorphous solid.

Melting point: 120° C.

TLC (silica gel): $R_f$=0.63 (dichloromethane/methanol 15:1)

Analysis: $C_{48}H_{40}N_6O_{10}$ (866.93)

| | | | |
|---|---|---|---|
| calculated | C 66.50 | H 5.34 | N 9.69 |
| found | 65.82 | 5.21 | 9.77 |

UV (methanol): $\lambda_{max}$ [nm] (lg ε): 203 (4.91); 233 (4.49); 276 (4.45)

$^1$H-NMR (250 MHz, d$_6$-DMSO, ppm): 11.25 (s, 1H, NH); 8.65–8.61 (m, 2H, H—C(2)); 8.07–8.02 (m, 4H, o-H to NO$_2$ (NPEE), o-H (benzoyl)); 7.64–7.51 (m, 3H, m- and p-H (benzoyl)); 7.36–7.15 (m, 11H, m-H to OCH$_3$, H(phenyl), m-H to NO$_2$(NPEE)); 6.84–6.81 (m, 4H, o-H to OCH$_3$)); 6.17–6.16 (m, 1H, H—C(1')); 5.35–5.33 (m, 1H, HO—C (3')); 5.05–4.91 (m, 1H, CH (NPEE)); 4.87–4.83 (m, 1H, H—C(2')); 4.48–4.31 (m, 1H, H-(3')); 4.13 (m, 1H, H—C (4')); 3.70–3.48 (m, 10H, OCH$_3$, CH$_2$(5'), α-CH$_2$(NPEE)); 2.70–2.61 (m, 2H, β-CH$_2$ (NPEE)); 1.25+1.13 (2d, 3H, CH$_3$ (NPEE)).

24. N$^6$-Benzoyl-5'-O-(4,4'-dimethoxytriphenylmethyl)-2'-O-[1-(4-nitrophenylethoxy)ethyl]adenosine-3'-O-(N,N-diisopropyl-2-cyanoethyl)phosphitamide 1.0 g (1.5 mmol) of N$^6$-benzoyl-5'-O-(4,4'-dimethoxytriphenylmethyl)-2'-O-[1-(4-nitrophenylethoxy)ethyl]adenosine and 54.64 mg (0.78 mmol) of 1H-tetrazole are weighed into a flask flooded with nitrogen gas, the reactants are dissolved in 20 ml of absolute, acid-free dichloromethane, 0.83 g (3.11mmol) of bis(diisopropylamino)(2-cyanoethoxy)phosphine is added, and the reaction solution is stirred under a protective gas atmosphere overnight. It is subsequently diluted with dichloromethane and extracted by shaking 3 x with 50 ml of sodium chloride/sodium bicarbonate solution each time, the aqueous phases are back-extracted with dichloromethane and all the organic phases are combined, dried over sodium sulfate, filtered and evaporated in a rotary evaporator.

For purification, the crude product is loaded onto a silica gel column (3.0×15.0 cm) and eluted with toluene (200 ml), toluene/ethyl acetate 3:1 (400 ml), 2:1 (600 ml) and, after 550 ml of mobile phase have been used, the first product fraction is obtained, end the subsequent fractions are combined and evaporated in a rotary evaporator. The resulting residue is coevaporated several times with dichloromethane until a foam forms. Drying of the colorless foam under high vacuum results in isolation of 1.07 g (1.0 mmol, 87%) of the desired product.

TLC (silica gel): $R_f$=0.54+0.66 (toluene/ethyl acetate 1:3)

Analysis: $C_{57}H_{63}N_8O_{11}P$ (1067.15)

| | | | |
|---|---|---|---|
| calculated | C 64.15 | H 5.95 | N 10.50 |
| found | 64.52 | 6.27 | 9.96 |

UV (methanol): $\lambda_{max}$ [nm] (lg ε): 204 (4.93); 233 (4.52); 276 (4.46)

$^1$H-NMR (250 MHz, CDCl$_3$, TMS, ppm): 9.10 (s, 1H, NH); 8.70–8.68 (m, 1H, H—C(8)); 8.28–8.21 (m, 1H, H—C (2)); 8.04–7.99 (m, 4H, o-H to NO$_2$ (NPEE), o-H(benzoyl); 7.62–7.16 (m, 14H, H(phenyl), m- and p-H(benzoyl), m-H to NO$_2$(NPEE), m-H to OCH$_3$)); 6.83–6.67 (m, 4H, o-H to OCH$_3$)); 6.23–6.11 (m, 1H, H—C(1')); 5.39–5.11 (m, 1H, H—C(2')); 4.98–4.72 (m, 1H, CH(NPE)); 4.3–4.53 (m, 1H, H—C(4')); 3.93–3.82 (m, 2H, α-CH$_2$(NPEE)); 3.77+3.76 (2s, 6H, OCH$_3$); 3.68–3.21 (m, 6H, P-O-CH$_2$, CH$_2$(5'),N—

CH); 2.70–2.62 (m, 4H, CH$_2$-CN, β-CH$_2$(NPEE)); 1.38–1.02 (m, 15H, CH$_3$(NPEE), C(CH$_3$)$_2$)

$^{31}$P-NMR (161.70 MHz, CDCl$_3$, H$_3$PO$_4$, ppm): 151.60; 151.05; 150.87; 150.54.

25.1 N$^2$-[2-(4-Nitrophenyl)ethoxycarbonyl]-O$^6$-[2-(4-nitrophenyl)ethyl]-2'-O-[1-(4-nitrophenylethoxy)ethyl]-3',5'-O-(1,1,3,3-tetraisopropyldisiloxane-1,3-diyl)guanosine 0.5 g (0.575 mmol) of N$^2$-[2-(4-nitrophenyl)ethoxycarbonyl]-O$^6$-[2-(4-nitrophenyl)ethyl]-3',5'-O-(1,1,3,3-tetraisopropyldisiloxane-1,3-diyl)guanosine is dissolved in 7 ml of absolute dichloromethane, 0.6 mg (7.1 µmol) of p-TsOH.H$_2$O is added, and the mixture is cooled in an ice bath to 0° C. Subsequently 0.22 g (1.15 mmol) of 4-nitrophenylethyl vinyl ether is added, and the reaction solution is initially stirred in the ice bath and, after 2 hours, allowed to warm slowly and is subsequently stirred at room temperature overnight. It is diluted with dichloromethane and extracted by shaking 3 x with 40 ml of saturated sodium bicarbonate solution each time, the aqueous phases are back-extracted with dichloromethane, and all the organic phases are combined, dried over sodium sulfate and evaporated in a rotary evaporator.

For purification, the oily residue is loaded onto a silica gel column (3.0×11.0 cm) and chromatographed with toluene (500 ml), toluene/ethyl acetate 20:1 (630 ml), 15:1 (320 ml), 10:1 (440 ml), 5:1 (360 ml), 4::1 (350 ml) and, after 1900 ml of mobile phase have been used, the first product fraction is obtained, and all product-containing fractions are combined and evaporated in a rotary evaporator. A colorless foam is obtained by coevaporating the oily residue several times with dichloromethane. Drying of the foam at 40° C. under high vacuum results in isolation of 0.55 g (0.518 mmol, 90%) of desired product.

TLC (silica gel): R$_f$=0.53 (toluene/ethyl acetate 1:1)

Analysis: C$_{49}$H$_{64}$N$_8$O$_{15}$Si$_2$ (1061.27)

| | | | |
|---|---|---|---|
| calculated | C 55.45 | H 6.07 | N 10.55 |
| found | 55.91 | 6.39 | 9.83 |

$^1$H-NMR (250 MHz, d$_6$-DMSO, ppm): 10.31+10.30 (2s, 1H, NH); 8.20–8.10 (m, 5H, H—C(8), o-H to NO$_2$ (NPE and NPEOC)); 7.93+7.74 (2d, 2H, o-H to NO$_2$ (NPEE)); 7.64–7.56 (m, 4H, m-H to NO$_2$ (NPE and NPEOC); 7.37+7.23 (2d, 2H, m-H to NO$_2$(NPEE)); 5.91+5.88 (2d, 1H, H—C(1')); 5.04+4.93 (2q, 1H, CH(NPEE)); 4.76–4.41 (m, 4H, α-CH$_2$(NPEOC), H—C(2'), H—C(3')); 4.34 (m, 2H, α-CH$_2$(NPE)); 4.18–3.53 (m, 5H, HC(4'), α-CH$_2$(NPEE), CH$_2$ (5')); 3.28 (t, 2H, β-CH$_2$ (NPEOC)); 3.07 (m, 2H, β-CH$_2$(NPE)); 2.82+2.72 (2t, 2H, β-CH$_2$(NPEE)); 1.29+1.25 (2d, 3H, CH$_3$(NPEE)); 0.99–0.83 (m, 28H, isopropyl)

25.2 N$^2$-[2-(4-Nitrophenyl)ethoxycarbonyl]-O$^6$-[2-(4-nitrophenyl)ethyl]-2'-O-[1-(4-nitrophenylethoxy)ethyl]guanosine 0.4 g (0.46 mmol) of N$^2$-[2-(4-nitrophenyl)ethoxycarbonyl]-O$^6$-[2-(4-nitrophenyl)ethyl]-2'-O-[1-(4-nitrophenylethoxy)ethyl]-3',5'-O-(1,1,3,3-tetraisopropyldisiloxane-1,3-diyl)guanosine is dissolved in 2.0 ml of absolute tetrahydrofuran, 0.35 g (1.10 mmol) of tetrabutylammonium fluoride.3H$_2$O and 0.12 ml (2.21 mmol) of glacial acetic acid are added, and the mixture is stirred at room temperature for 5 hours and subsequently evaporated in a rotary evaporator.

For purification, the crude product is loaded onto a silica gel column (2.5×14.0 cm) and eluted with dichloromethane (300 ml), dichloromethane/methanol 100:1 (400 ml), 90:1 (540 ml), 80:1 (400 ml), 70:1 (350 ml) and, after 800 ml of mobile phase have been used, the first fraction which contains product is obtained, and all product-containing fractions are combined and evaporated in a rotary evaporator. The resulting residue is coevaporated several times with dichloromethane until a foam forms, and the colorless foam is dried at 40° C. under high vacuum and then 0.288 g (0.351 mmol, 95%) of compound is isolated.

TLC (silica gel): R$_f$=0.25+0.3 (dichloromethane/methanol 95:5)

Analysis: C$_{37}$H$_{38}$N$_8$O$_{14}$ (818.76)

| | | | |
|---|---|---|---|
| calculated | C 54.27 | H 4.67 | N 13.68 |
| found | 54.25 | 5.16 | 13.26 |

UV (methanol): λ$_{max}$ [nm] (lg ε): 202 (4.60); 215 (4.60); 268 (4.60)

$^1$H-NMR (250 MHz, d$_6$-DMSO, ppm): 10.53+10.34 (2s, 1H, NH); 8.48+8.43 (2s, 1H, H—C(8)); 8.15–8.10 (m, 4H, o-H to NO$_2$(NPE and NPEOC)); 8.0–7.92 (2d, 2H, o-H to NO$_2$ (NPEE)); 7.62–7.57 (m, 4H, m-H to NO$_2$ (NPE and NPEOC)); 7.23+7.19 (2d, 2H, m-H to NO$_2$ (NPEE)); 6.0+5.97 (2d, 1H, H—C(1')); 5.23+5.18 (2d, 1H, HO—C(3')); 5.07–5.00 (m, 1H, HO—C(5')); 4.78–4.60 (m, 4H, α-CH$_2$ (NPEOC), H—C (2'), CH(NPEE)); 4.36 (t, 2H, α-CH$_2$ (NPE)); 4.28–4.18 (m, 1H, HC(4')); 3.72–3.49 (m, 4H, CH$_2$ (5'), α-CH$_2$ (NPEE)); 3.36–3.26 (m, 2H, β-CH$_2$ (NPEOC)); 3.09 (t, 2H, β-CH$_2$(NPE)); 2.66–2.52 (m, 2H, β-CH$_2$ (NPEE)); 1.17+1.11 (2d, 3H, CH$_3$ (NPEE))

25.3 N$^2$-[2-(4-Nitrophenyl)ethoxycarbonyl]-O$^6$-[2-(4-nitrophenyl)ethyl]-2'-O-[1-(4-nitrophenylethoxy)ethyl]guanosine 2.0 g (2.3 mmol) of N$^2$-[2-(4-nitrophenyl)ethoxycarbonyl]-O$^6$-[2-(4-nitrophenyl)ethyl]-3',5'-O-(1,1,3,3-tetraisopropyldisiloxane- 1,3-diyl)guanosine are dissolved in 25 ml of absolute dichloromethane, 2.8 mg (14.22 µmol) of p-TsOH.H$_2$O are added, and the mixture is cooled to 0° C. in an ice bath. To this solution is added 0.99 g (4.6 mmol) of 4-nitrophenylethyl vinyl ether, and the mixture is first stirred in the ice bath and, after 2 hours, allowed to warm slowly to room temperature and then stirred overnight. The reaction solution is diluted with dichloromethane and washed 3 x with 50 ml of saturated sodium bicarbonate solution each time. All the aqueous phases are back-extracted with dichloromethane, and the combined organic phases are dried over sodium sulfate, filtered and evaporated in a rotary evaporator. The resulting oil is dissolved in 6.0 ml of absolute tetrahydrofuran, 1.67 g (5.3 mmol) of tetrabutylammonium fluoride.3H$_2$O and 0.6 ml (0.01 mmol) of glacial acetic acid are added, and the mixture is stirred at room temperature for 5 hours and subsequently evaporated in a rotary evaporator.

For purification, the crude product is loaded onto a silica gel column (3.0×13.0 cm) and eluted with dichloromethane (400 ml), dichloromethane/methanol 100:1 (500 ml), 90:1 (360 ml), 80:1 (800 ml), 70:1 (350 ml) and, after 1100 ml of mobile phase have been used, the first product fraction is obtained. All following fractions which contain product are combined and evaporated in a rotary evaporator, and the residue is coevaporated several times with dichloromethane until a foam forms. Drying of the colorless foam at 40° C.

under high vacuum results in 1.75 g (1.64 mmol, 93%) of the desired product.

TLC (silica gel): $R_f$=0.25+0.3 (dichloromethane/methanol 95:5) $C_{37}H_{38}N_8O_{14}$ (818.76)

Spectroscopic data are identical to Example 25.2.

25.4 5'-O-(4,4'-Dimethoxytriphenylmethyl) -$N^2$-[2-(4-nitrophenyl)ethoxycarbonyl]-$O^6$-[2-(4-nitrophenyl)ethyl)-2'-O-[1-(4-nitrophenylethoxy)ethyl]guanosine 1.8 g (2.19 mmol) of $N^2$-[2-(4-nitrophenyl)ethoxycarbonyl]-$O^6$-[2-(4-nitrophenyl)ethyl]-2'-O-[1-(4-nitrophenylethoxy)ethyl]guanosine are coevaporated 3 x with 10 ml of absolute pyridine each time, the residue is taken up in 35 ml of absolute pyridine, 0.96 g (2.85 mmol) of 4,4'-dimethoxytriphenylmethyl chloride is added, and the mixture is stirred at room temperature overnight. The reaction mixture is subsequently diluted with ethyl acetate and washed 3 x with 50 ml of saturated sodium bicarbonate solution each time, the aqueous phases are back-extracted with ethyl acetate, all the organic phases are combined, dried over sodium sulfate, filtered and evaporated in a rotary evaporator, and the residue is coevaporated several times with toluene.

For purification, the crude product is loaded onto a silica gel column (3.0×14.0 cm) and chromatographed with toluene (200 ml), toluene/ethyl acetate 5:1 (300 ml), 4:1 (750 ml), 3:1 (800 ml), 2:1 (1200 ml) and, after 1300 ml of mobile phase have been used, the first product fraction is obtained, and all subsequent fractions are combined and evaporated in a rotary evaporator. The residue is dissolved in 5 ml of dichloromethane and added dropwise to 200 ml of n-hexane, the resulting precipitate is filtered off with suction and dried at 40° C. under high vacuum over paraffin shavings and subsequently 2.36 g (2.1 mmol, 96%) of compound are isolated as a colorless amorphous solid.

TLC (silica gel): $R_f$=0.6 (toluene/ethyl acetate/methanol 5:4:1)

Analysis: $C_{58}H_{56}N_8O_{16}$ (1121.13)

| | | | |
|---|---|---|---|
| calculated | C 62.13 | H 5.03 | N 9.99 |
| found | 61.61 | 5.03 | 10.18 |

UV (methanol): $\lambda_{max}$ [nm] (lg ε): 201 (5.01); [214 (4.77)]; 236 (4.49); 268 (4.65)

$^1$H-NMR (250 MHz, $d_6$-DMSO, ppm): 10.33 (2s, 1H, NH); 8.31 (s, 1H, H—C(8)); 8.15–8.11 (m, 4H, o-H to NO$_2$ (NPEOC and NPE)); 7.98+7.92 (2d, 2H to NO$_2$ (NPEE)); 7.64–7.55 (m, 4H, m-H to NO$_2$ (NPEOC and NPE)); 7.33–7.15 (m, 1H, m-H to NO$_2$(NPEE)), H(phenyl), m-H to OCH$_3$); 6.80–6.70 (m, 4H, o-H to OCH$_3$); 6.02 (m, 1H, H—C(1')); 5.20 (d, 1H, HO—C(3')); 4.84–4.70 (m, H—C (2'), CH(NPEE), α-CH$_2$(NPEOC)); 4.84–4.30 (m, 3H, H—C(3'), α-CH$_2$(NPE)); 4.01 (m, 1H, HC(4')); 3.688+3.685+3.680+3.673 (4s, 6H, OCH$_3$); 3.66–3.26 (m, 4H, CH$_2$ (5'), α-CH$_2$ (NPEE)); 3.34–3.19 (m, 2H, β-CH$_2$ (NPEOC)); 3.07 (t, 2H, β-CH$_2$(NPE)); 2.71–2.50 (m, 2H, β-CH$_2$(NPEE)); 1.19+1.14 (2d, 3H, CH$_3$ (NPEE))

26. 5'-O-(4,4'-Dimethoxytriphenylmethyl) -$N^2$-[2-(4-nitrophenyl) ethoxycarbonyl]-$O^6$-[2-(4-nitrophenyl)ethyl]-2'-O-[1-(4-nitrophenylethoxy)ethyl]guanosine-3'-O-(N,N-diisopropyl-2-cyanoethyl) phosphitamide 0.4 g (0.35 mmol) of 5'-O-(4,4'-dimethoxytriphenylmethyl)-$N^2$-[2-(4-nitrophenyl) ethoxycarbonyl]-$O^6$-[2-(4-nitrophenyl)ethyl]-2'-O-[1-(4-nitrophenylethoxy)ethyl]guanosine and 15.0 mg (0.21 mmol) of 1H-tetrazole are weighed into a flask flooded with nitrogen gas, the reactants are dissolved in 8 ml of absolute acetonitrile (residue analysis), 0.25 g (0.85 mmol) of bis (diisopropylamino)(2-cyanoethoxy)phosphine is added, and the reaction mixture is stirred under a protective gas atmosphere at room temperature overnight. It is subsequently diluted with ethyl acetate and washed 3 x with 40 ml of sodium chloride/sodium bicarbonate solution each time. The aqueous phases are back-extracted with ethyl acetate, and all the organic phases are dried over sodium sulfate, filtered and evaporated in a rotary evaporator.

For purification, the crude product is loaded onto a silica gel column (2.5×21.0 cm) and eluted with toluene (100 ml), toluene/ethyl acetate 4:1 (125 ml), 3:1 (400 ml), 2:1 (150 ml), 1:1 (100 ml), it being possible to collect the first product fraction after 350 ml of mobile phase have been used, and all the fractions subsequently being combined and evaporated in a rotary evaporator. Coevaporation of the residue with ethyl acetate and drying of the colorless foam under high vacuum result in 0.34 g (0.25 mmol, 75%) of guanosinephosphitamide.

TLC (silica gel): $R_f$=0.43+0.52 (toluene/ethyl acetate 1:1)
Analysis: $C_{67}H_{73}N_{10}O_{17}P$ (1321.35)

| | | | |
|---|---|---|---|
| calculated | C 60.90 | H 5.56 | N 10.60 |
| found | 60.85 | 5.74 | 10.18 |

UV (methanol): $\lambda_{max}$ [nm] (lg ε): 203 (50.5); [214 (4.85)]; 236 (4.51); 268 (4.63)

$^1$H-NMR (250 MHz, CDCl$_3$, TMS, ppm): 8.14–7.96 (m, 7H, H—C (8), o-H to NO$_2$ (NPE, NPEOC and NPEE)); 7.52–7.08 (m, 15H, m-H to NO$_2$ (NPE, NPEOC and NPEE), m-H to OCH$_3$ , H (phenyl)); 6.75+6.74 (2d, 4H, o-H to OCH$_3$)); 6.13–5.98 (m, 1H, H—C(1')); 5.28–5.08 (m, 1H, CH (NPEE)); 4.91–4.69 (m, 3H, H—C (2'), α-CH$_2$ (NPEOC)); 4.58–4.43 (m, 1H, H—C(3')); 4.41–4.19 (m, 3H, H—C(4'), α-CH$_2$(NPEE)); 4.08–3.53 (m, 2H, P-O-CH$_2$); 3.738+3.73 (2s, 6H, OCH$_3$); 3.68–3.46 (m, 4H, CH$_2$(5'), N—CH); 3.35–3.25 (m, 4H, α-CH$_2$ (NPE), β-CH$_2$ (NPEOC)); 3.08–2.98 (m, 3H, β-CH$_2$ (NPE)); 2.75–2.58 (m, 4H, CH$_2$-CN, β-CH$_2$ (NPEE)); 1.34–0.96 (m, 15H, CH$_3$(NPEE), C(CH$_3$)$_2$)

$^{31}$P-NMR (161.70 MHz, CDCl$_3$, H$_3$PO$_4$, ppm): 151.58; 151.02; 150.82; 150.48.

27. 5'-O-(4,4'-Dimethoxytriphenylmethyl) 2'-O-[1-(4-nitrophenylethoxy)ethyl]-3'-0-succinoyluridine 221.92 mg (0.3 mmol) of 5'-O-(4,4'-dimethoxytriphenylmethyl)-2'-O-[1-(4-nitrophenylethoxy)ethyl]uridine are coevaporated 2 x with 5 ml of absolute pyridine each time. The residue is dissolved in 7 ml of absolute dichloromethane, 48.86 mg (0.4 mmol) of 4-dimethylaminopyridine and 40.07 mg (0.4 mmol) of succinic anhydride are added and the mixture is stirred at room temperature overnight. The reaction solution is subsequently diluted with dichloromethane and extracted by shaking 2 x with 25 ml of saturated sodium bicarbonate solution each time, 3 x with 25 ml of 10% strength citric acid solution each time and 5 x with 30 ml of water each time. The aqueous phases are back-extracted with dichloromethane, and all the organic phases are dried over sodium sulfate, filtered and evaporated in a rotary evaporator.

For purification, the crude product is loaded onto a silica gel column (3.0×6.0 cm) and eluted with dichloromethane (200 ml), dichloromethane/methanol 100:1 (200 ml), 90:1

(450 ml), 80:1 (800 ml), 70:1 (560 ml), 60:1 (300 ml), 50:1 (300 ml) and, after 1000 ml of mobile phase have been used, the first product fraction is obtained. All the product-containing fractions are combined and evaporated in a rotary evaporator. The oily residue is coevaporated several times with ethyl acetate until a foam forms and is subsequently dried at 40° C. under high vacuum. It is possible to isolate 0.184 g (0.219 mmol, 73%) of desired product in the form of a pale yellow colored foam.

TLC (silica gel): $R_f$=0.54 (dichloromethane/methanol 9:1)

Analysis: $C_{44}H_{45}N_3O_{14}$ (839.86)

| | | | |
|---|---|---|---|
| calculated | C 62.92 | H 5.40 | N 5.00 |
| found | 62.21 | 5.22 | 5.62 |

UV (methanol): $\lambda_{max}$ [nm] (lg $\epsilon$): 202 (4.87); 233 (4.36); 266 (4.28)

$^1$H-NMR (250 MHz, d$_6$-DMSO, ppm): 11.49 (s, 1H, NH); 8.11–8.08 (m, 2H, o-H to NO$_2$(NPEE)); 7.72–7.66 (m, 1H, H—C(6)); 7.45–7.20 (m, 11H, m-H to NO$_2$ (NPEE), H (phenyl), m-H to OCH$_3$)); 6.87 (d, 4H, o-H to OCH$_3$)); 5.87–5.84 (m, 1H, H—C(1')); 5.48–5.42 (m, 1H, H—C(5)); 5.27–5.23 (m, 1H, H—C(3')); 4.82–4.73 (m, 1H, CH)NPEE)); 4.58–4.53 (m, 1H, H—C(2')); 4.14–4.12 (m, 1H, H—C(4')); 3.71 (s, 6H, OCH$_3$); 3.69–3.25 (m, 4H, α-CH$_2$(NPEE); CH$_2$(5')); 2.88–2.81 (m, 2H, β-CH$_2$(NPEE)); 2.50–2.48 (m, 4H, CH$_2$(succinate)); 1.19+1.13 (2d, 3H, CH$_3$(NPEE))

28. 5'-O-(4,4'-Dimethoxytriphenyl) -N$^4$-[2-(4-nitrophenyl)ethoxycarbonyl]-2'-O-[1-(4-nitrophenylethoxy)ethyl]-3'-O-succinoylcytidine 279.6 mg (0.3 mmol) of 5'-O-(4,4'-dimethoxytriphenylmethyl)-N$^4$-[2-(4-nitrophenyl) ethoxycarbonyl]-2'-O-[1-(4-nitrophenylethoxy)ethyl] cytidine are coevaporated 2 x with 5 ml of absolute pyridine each time, the residue is taken up in 7 ml of absolute dichloromethane, 48.86 mg (0.4 mmol) of 4-dimethylaminopyridine and 40.07 mg (0.4 mmol) of succinic anhydride are added, and the reaction solution is stirred at room temperature overnight. It is subsequently diluted with dichloromethane and washed successively 2 x with 30 ml of saturated sodium bicarbonate solution each time, 3 x with 30 ml of 10% strength citric acid solution each time, 1 x with 30 ml of saturated sodium bicarbonate solution and 1 x with 30 ml of water. The aqueous phases are backextracted with dichloromethane, and all the organic phases are dried over sodium sulfate, filtered and evaporated in a rotary evaporator.

For purification, the crude product is loaded onto a silica gel column (3.0×8.0 cm) and chromatographed with dichloromethane/methanol 100:1 (300 ml), 90:1 (570 ml), 85:1 (250 ml), B0:1 (240 ml), 70:1 (280 ml), 60:1 (540 ml), 50:1 (600 ml) and, after 2000 ml of mobile phase have been used, the first product fraction is obtained. All the fractions which contain product are combined and evaporated in a rotary evaporator. The residue is coevaporated several times with ethyl acetate until a foam forms and is subsequently dried at 40° C. under high vacuum. 0.288 g (0.28 mmol, 93%) of product are isolated as a pale yellow colored foam.

TLC (silica gel): $R_f$=0.63 (dichloromethane/methanol 9:1)

Analysis: $C_{53}H_{55}N_5O_{18}$×H$_2$O (1050.04)

| | | | |
|---|---|---|---|
| calculated | C 60.62 | H 5.27 | N 6.66 |
| found | 60.89 | 5.59 | 6.19 |

UV (methanol): $\lambda_{max}$ [nm] (lg $\epsilon$): 202 (4.99); 236 (4.56); 274 (4.42)

$^1$H-NMR (250 MHz, d$_6$-DMSO, ppm): 10.90 (s, 1H, NH); 8.20–8.02 (m, 5H, H—C(6), o-H to NO$_2$(NPEOC and NPEE)); 7.58–7.21 (m, 13H, m-H to NO$_2$(NPEE and NPEOC), H(phenyl), m-H to OCH$_3$); 6.83–6.78 (m, 5H, H—C(5), o-H to OCH$_3$); 5.90 (m, 1H, H—C(1')); 5.22 (m, 1H, H—C(3')); 4.97–4.73 (m, 1H, CH(NPEE)); 4.50–4.35 (m, 3H, α-CH$_2$(NPEOC), H—C(2')); 4.19 (m, 1H, H—C(4')); 3.72 (s, 6H, OCH$_3$); 3.61–3.34 (m, 4H, α-CH$_2$(NPEE), CH$_2$(5')); 3.07 (m, 2H, β-CH$_2$ (NPEOC)); 2.82 (m, 2H, β-CH$_2$ (NPEE)); 2.59–2.49 (m, 4H, CH$_2$ (succinate)); 1.20+ 1.09 (2d, 3H, CH$_3$ (NPEE)).

29. 5'-O-(4,4'-Dimethoxytriphenylmethyl) -N$^6$-[2-(4-nitrophenyl)ethoxycarbonyl]-2'-0-[1-(4-nitrophenylethoxy)ethyl]-3'-O-succinoyladenosine 239.0 mg (0.25 mmol) of 5'-O-(4,4'-dimethoxytriphenylmethyl)-N$^6$-[2-(4-nitrophenyl) ethoxycarbonyl]-2'-O-[1-(4-nitrophenylethoxy)ethyl] adenosine are coevaporated 2 x with 5 ml of absolute pyridine, the residue is dissolved in 5 ml of absolute dichloromethane, 40.72 mg (0.33 mmol) of 4-dimethylaminopyridine and 33.35 mg (0.33 mmol) of succinic anhydride are added, and the mixture is stirred at room temperature overnight. The reaction mixture is subsequently diluted with ethyl acetate and extracted by shaking successively 3 x with 30 ml of saturated sodium bicarbonate solution each time, 3 x with 30 ml of 10% strength citric acid solution each time, 1 x with 30 ml of saturated sodium bicarbonate solution and 1 x with 30 ml of water. The aqueous phases are back-extracted with ethyl acetate, and all the organic phases are dried over sodium sulfate, filtered and evaporated in a rotary evaporator. The resulting oil is dissolved in 3 ml of ethyl acetate and added dropwise to 70 ml of n-hexane, and the resulting precipitate is filtered off with suction and dried at 40° C. under high vacuum over paraffin shavings. 0.201 g (0.19 mmol, 76%) of desired product is obtained in the form of a colorless amorphous solid.

TLC (silica gel): $R_f$=0.62 (dichloromethane/methanol 9:1)

Analysis: $C_{54}H_{55}N_7O_{17}$×H$_2$O (1074.07)

| | | | |
|---|---|---|---|
| calculated | C 60.38 | H 5.16 | N 9.12 |
| found | 59.91 | 4.91 | 9.14 |

UV (methanol): $\lambda_{max}$ [nm] (lg $\epsilon$): 202 (5.02); 236 (4.44); 267 (4.58); [275 (4.51)]

$^1$H-NMR (250 MHz, d$_6$-DMSO, ppm): 12.28 (s, 1H, OH-(succinate)); 10.70 (s, 1H, NH); 8.62 (s, 1H, H—C(8)); 8.46+8.43 (2s, 1H, H—C(2)); 8.13 (d, 2H, o-H to NO$_2$ (NPEOC)); 8.03–7.97 (m, 2H, o-H to NO$_2$ (NPEE)); 7.60 (d, 2H, m-H to NO$_2$(NPEOC)); 7.39–7.09 (m, 11H, m-H to NO$_2$(NPEE), H(phenyl), m-H to OCH$_3$)); 6.84–6.79 (m, 4H, o-H to OCH$_3$)); 6.18–6.12 (m, 1H, H—C(1')); 5.42–5.38 (m, 2H, H—C(2'), H—C(3')); 4.78–4.66 (m, 1H, CH(NPEE));

4.38 (t, 2H, α-CH$_2$(NPEOC)); 4.27 (m, 1H, H—C(4')); 3.70 (s, 6H, OCH$_3$); 3.35–3.22 (m, 3H, H—C (5'), α-CH$_2$ (NPEE)); 3.12–3.02 (m, 3H, H-C(5"), β-CH$_2$(NPEOC)); 2.59–2.39 (m, 6H, β-CH$_2$ (NPEE)), CH$_2$ (succinate)); 1.10+1.01 (2d, 3H, CH$_3$ (NPEE))

30. 5'-O-(4,4'-Dimethoxytriphenylmethyl)-N$^2$-[2-(4-nitrophenyl)ethoxycarbonyl]-O$^6$-[2-(4-nitrophenyl)ethyl]-2'-O-[1-(4-nitrophenylethoxy)ethyl]-3'-O-succinoylguanosine 168.17 mg (0.15 mmol) of 5'-O-(4,4'-dimethoxytriphenylmethyl)-N$^2$-[2-(4-nitrophenyl)ethoxycarbonyl]-O$^6$-[2-(4-nitrophenyl)ethyl]-2'-O-[1-(4-nitrophenylethoxy)ethyl]guanosine are coevaporated 3 x with 5 ml of absolute pyridine each time, the residue is taken up in 25 ml of absolute dichloromethane, 24.43 mg (0.2 mmol) of 4-dimethylaminopyridine and 20.01 mg (0.2 mmol) of succinic anhydride are added, and the reaction solution is stirred at room temperature overnight. It is subsequently diluted with ethyl acetate and extracted by shaking successively 3 x with 20 ml of 10% strength citric acid solution each time, 2x with 20 ml of saturated sodium bicarbonate solution each time and 2 x with 20 ml of water each time. The aqueous phases are backextracted with ethyl acetate, and all organic phases are dried over sodium sulfate, filtered and evaporated in a rotary evaporator. The oily residue is dissolved in 2 ml of ethyl acetate and added dropwise to 40 ml of n-hexane, and the resulting precipitate is filtered off with suction and dried at 40° C. under high vacuum over paraffin shavings. 0.116 g (0.095 mmol, 64%) of the desired product is obtained in the form of a colorless amorphous solid.

TLC (silica gel): R$_f$=0.46 (toluene/ethyl acetate/methanol 5:4:1)

Analysis: C$_{62}$H$_{60}$N$_8$O$_{19}$ (1221.21)

|  | C | H | N |
|---|---|---|---|
| calculated | 60.97 | 4.95 | 9.17 |
| found | 60.28 | 4.96 | 9.15 |

UV (methanol): λ$_{max}$ [nm] (lg ε): 202 (5.07); [214 (4.88)]; 236 (4.48); 268 (4.64);

$^1$H-NMR (250 MHz, d$_6$-DMSO, ppm): 12.28 (s, 1H, HO-(succinate)); 10.32+10.28 (2s, 1H, NH); 8.39+8.37 (2s, 1H, H—C(8)); 8.16+8.10 (m, 4H, o-H to NO$_2$ (NPE and NPEOC)); 8.01–7.96 (m, 2H, o-H to NO$_2$ (NPEE)); 7.63–7.57 (m, 4H, m-H to NO$_2$ (NPE and NPEOC)); 7.31–7.10 (m, 11H, m-H to NO$_2$ (NPEE), H(phenyl), m-H to OCH$_3$)); 6.78–6.70 (m, 4H, o-H to OCH$_3$); 6.08–6.0 (m, 1H, H—C (1')); 5.48–5.30 (m, 2H, H—C(2'), H—C(3')); 4.78–4.60 (m, 3H, α-CH$_2$ (NPEOC), CH (NPEE)); 4.37 (m, 2H, α-CH$_2$ (NPE)); 4.13 (m, 1H, H—C(4')); 3.68 (s, 6H, OCH$_3$); 3.60–3.05 (m, 8H, CH$_2$(5'), α-CH$_2$(NPEE), β-CH$_2$(NPEOC and NPE)); 2.55–2.49 (m, 6H, β-CH$_2$ (NPEE), CH$_2$ (succinate)); 1.09+1.01 (2d, 3H, CH$_3$(NPEE)).

31. General method for the preparation of 4-alkoxycarbonyloxybenzyl vinyl ether and 4-acyloxybenzyl vinyl ether derivatives

31.1 3-Fluoro-4-hydroxybenzyl alcohol 22.8 g (0.2 mol) of 2-fluorophenol are dissolved in 60 ml of 20% KOH (0.214 mol), and the yellowish solution is heated to 60° C. on an oil bath. Subsequently 30 ml of a 37% strength formaldehyde solution (0.370 mmol) are made up to 100 ml with H$_2$O and then added dropwise over the course of 3 hours. A TLC check shows the formation of two main products, with the one migrating further corresponding to the desired monoalkylated product. The solution, which is now reddish, is maintained at 60° C. for a further 3 hours before the cooled solution is poured onto 0.5 l of ice-water/300 ml of ethyl acetate (EA). The pH is adjusted to 5–6 with about 20 ml of conc. HCl. The organic phase is separated off in a separating funnel and then washed twice with 300 ml of phosphate buffer pH 6 each time and 300 ml of saturated NaCl solution, and the collected aqueous phases are back-extracted twice with 150 ml of EA and again washed with phosphate buffer/NaCl solution. The combined organic phases are dried over Na$_2$SO$_4$, filtered and concentrated to an oil (about 23 g) in a rotary evaporator. Further working up is by chromatography. For this purpose, a column (diameter 6 cm) is charged with 200 g of flash silica gel, equilibrated with toluene and, after loading on of the crude product, subjected to the following gradient (tol/EA in ml): 200/0, 450/50, 400/100, 350/150, 300/200. The eluate is collected in fractions each of 100 ml, and the product fractions (about 500 ml) are combined and concentrated to about 100 ml in a rotary evaporator. After scratching with a glass rod, the solution is stored in a refrigerator overnight for crystallization. The colorless mass of crystals is filtered off with suction, washed with 2×20 ml of cold petroleum ether and dried under high vacuum at 50° C.

In this way, 10.3 g (7.25 mmol, 36%) of 3-fluoro-4-hydroxybenzyl alcohol are obtained.

TLC (silica gel): R$_f$=0.52 (tol/EA=1/2);

Melting point: 101° C.

UV (methanol): λ$_{max}$ [nm] (lg ε): 222 (3.98), 272 (3.22)

$^1$H-NMR (250 MHz, d$_6$-DMSO,TMS, ppm): 9.80 (s, 1H, phenyl-OH); 7.05 (s, 1H, H-(C2)); 6.95–6.80 (m, 2H, H-(C6), H-(C5)); 5.12 (s, 1H, benzyl-OH); 4.35 (d, 2H, CH$_2$).

31.2 4-Methoxytrityl 2,5-dichloro-4-hydroxybenzyl ether 6 g (31.1 mmol) of 2,5-dichloro-4-hydroxybenzyl alcohol are dissolved in 70 ml of abs. pyridine and then 11.0 g (35.62 mmol) of monomethoxytrityl chloride are added. The yellowish solution is stirred at room temperature for several hours. A TLC check indicates complete conversion before the reaction is stopped with 20 ml of MeOH and stirring for about 30 minutes. The colorless reaction solution is concentrated to about 30 ml in a rotary evaporator, diluted with 300 ml of EA and then washed three times with 300 ml of saturated NaCl solution each time. The combined aqueous phases are back-extracted twice with 200 ml of EA, and the latter is then washed once with 200 ml of saturated NaCl solution. The EA phases are dried over Na$_2$SO$_4$, filtered and concentrated to an oil (about 17 g) in a rotary evaporator. After coevaporation with 50 ml of toluene twice, the crude product is purified by chromatography. The eluate is collected in fractions each of 75 ml, and the product fractions are combined (about 300 ml) and concentrated to an oil in a rotary evaporator. The product is coevaporated twice with 30 ml of distilled MeOH and converted into a foam with distilled CH$_2$Cl$_2$, and the foam is dried, gradually resinifying, under high vacuum at 25° C. The yield is 13.51 g (27.27 mmol) which is 88% of theory.

TLC (silica gel): R$_f$=0.32 (tol/EA=10/1)

$^1$H-NMR (250 MHz, d$_6$-DMSO, TMS, ppm): 10.65 (bs, 1H, phenyl-OH); 7.48–7.10 (m, 13H, phenyl-H, H-(C6)); 7.00–6.81 (m, 3H, H-(C3), o-H to —OCH$_3$); 4.05 (s, 2H, CH$_2$); 3.68 (s, 3H, —OCH$_3$).

31.3 3-Chloro-4-[2-(4-nitrophenyl)ethoxycarbonyloxy]benzyl alcohol 4-methoxytrityl 3-chloro-4-hydroxybenzyl ether (12.1 g=28.08 mmol) which has been coevaporated with abs. toluene is taken up in 50 ml of abs. $CH_3CN$, and 9.35 g (30.0 mmol) of 2-(p-nitrophenyl)ethoxycarbonyl-1-methylimidazolium chloride are added. Subsequently 700 mg of DMAP are added to the suspension, and the mixture is stirred at room temperature for 30 minutes, the precipitate dissolving within a few minutes. The reaction solution is concentrated to about half the volume in a rotary evaporator, diluted with 300 ml of EA and washed with 200 ml each of saturated $NaHCO_3$/NaCl solution, and the collected aqueous phases are back-extracted with 100 ml of EA twice and again washed with $NaHCO_3$/NaCl solution. The combined organic phases are dried over $Na_2SO_4$, filtered and concentrated to a yellowish oil (about 24 g) in a rotary evaporator. The crude product is sufficiently pure for the subsequent acidic ether cleavage. The oil is taken up in 50 ml of $CHCl_3$/MeOH (4/1), 1.0 g (3.17 mmol) of p-toluenesulfonic acid is added, and the mixture is stirred at room temperature for 2 to 3 hours. The reaction solution is diluted with 200 ml of $CHCl_3$ and poured into cold saturated $NaHCO_3$ solution. The organic phase is separated off in a separating funnel and then again washed with 200 ml of $NaHCO_3$ solution and 200 ml of saturated NaCl solution, the aqueous phases are back-extracted with 50 ml portions of $CHCl_3$, and the combined org. phases are dried over $Na_2SO_4$, filtered and concentrated to an oil (about 25 g) in a rotary evaporator. Further purification is by chromatography. For this purpose, a column (diameter 6 cm) is charged with 250 g of flash silica gel, equilibrated with toluene and, after loading on of the crude product, subjected to the following gradient (tol/EA in ml): 300/0, 450/50, 400/100, 350/150, 300/200. The eluate is collected in fractions each of 50 ml, and the product fractions are combined (about 300 ml) and concentrated to an oil in a rotary evaporator. After coevaporation with MeOH, the resin is converted into a foam with $CH_2Cl_2$ and dried under high vacuum at room temperature. This results in 7.41 g (21.07 mmol, 74%) of a colorless resin.

TLC (silica gel): $R_f$=0.24 (tol/EA=3/1)

31.4 2,5-Dichloro-4-pivaloyloxybenzyl alcohol

4-Methoxytrityl 2,5-dichloro-4-hydroxybenzyl ether (12.0 g=24.22 mmol) which has been coevaporated with abs. toluene is taken up in 150 ml of abs. $CH_3CN$, and 15 ml=13.77 g (73.93 mmol) of pivalic anhydride (analytical grade) are added. Subsequently 780 mg of DMAP are added, and the mixture is stirred at room temperature for 30 minutes. The reaction is complete after about 30 minutes. The reaction solution is concentrated to about 50 ml in a rotary evaporator, diluted with 200 ml of EA and washed with 200 ml each of saturated $NaHCO_3$/NaCl solution, and the collected aqueous phases are back-extracted with 100 ml of EA twice and again washed with $NaHCO_3$/NaCl solution. The combined organic phases are dried over $Na_2SO_4$, filtered and concentrated to a yellowish oil on a rotary evaporator. In analogy to the method of 31.3 (elimination of the methoxytrityl protective group), 6.01 g (21.68 mmol) of a colorless resin are obtained.

TLC (silica gel): $R_f$=0.29 (tol/EA=3/1)

$^1$H-NMR (250 MHz, $CDCl_3$, TMS, ppm): 7.58 (s, 1H, H-(C3)); 7.12 (s, 1H, H-(C5)); 4.70 (s, 2H, —$CH_2$); 1.38 (s, 9H, —$CH_3$).

31.5 2-Chloro-4-[2-(4-nitrophenyl)ethoxycarbonyloxy]benzyl vinyl ether 7.48 g (20.12 mmol) of 2-chloro-4-[2-(4-nitrophenyl)ethoxycarbonyloxy]benzyl alcohol are dissolved in 120 ml of ethyl vinyl ether, 680 mg of mercury(II) bistrifluoroacetate are added, and the mixture is stirred at room temperature for 6 hours. The reaction is stopped by dilution with 300 ml of EA and pouring into 200 ml of saturated $NaHCO_3$ solution. The washing of the org. phase is repeated with 100 ml of saturated $NaHCO_3$ solution and 100 ml of saturated NaCl solution. The collected aqueous phases are back-extracted with 100 ml of EA twice. The combined organic phases are dried over $Na_2SO_4$, filtered and concentrated to about 15 ml in a rotary evaporator. Further purification is by chromatography. For this purpose, a column (ø 4 cm) is charged with 150 g of flash silica gel, equilibrated with toluene and, after loading on of the crude product, eluted with 500 ml of toluene. The eluate is collected in fractions each of 50 ml, and the product fractions are combined (about 250 ml) and concentrated to an oil in a rotary evaporator. After coevaporation with 20 ml portions of distilled MeOH, the viscous oil is dried under high vacuum at 25° C.

The yield is 6.78 g (17.95 mmol) which is 82% of theory.

TLC (silica gel): $R_f$=0.78 (tol/EA=10/1)

$^1$H-NMR (250 MHz, $d^6$-DMSO, TMS, ppm): 8.18 (m, 2H, o-H to —$NO_2$); 7.50(d, 1H, H-(C6)); 7.42 (d, 2H, o-H to —$NO_2$), 7.20 (d, 1H, H-(C3)); 7.05 (dd, 1H, H-(C5)); 6.53 (dd, 1H, vinyl-H); 4.78 (s, 2H, —$CH_2$); 4.48 (t, 2H, α-$CH_2$ (NPEE)); 4.30 (dd, 1H, trans-vinyl-H); 4.12 (dd, 1H, cis-vinyl-H); 3.18 (t, 2H, β-$CH_2$ (NPEE)).

The following compounds are prepared analogously:

31.1.a 3-Chloro-4-hydroxybenzyl alcohol

Yield: 23%

TLC (silica gel): $R_f$=0.52 (tol/EA=1/2)

Melting point: 125° C.

$^1$H-NMR (250 MHz, $d^6$-DMSO, TMS, ppm): 10.05 (bs, 1H, phenyl-OH); 7.28 (s, 1H, H-(C2)); 7.08 (d, 1H, H-(C6)); 6.9 (d, 1H, H-(C5)); 5.12 (bs, 1H, benzyl-OH); 4.35 (s, 2H, $CH_2$).

31.1.b 2-Chloro-4-hydroxybenzyl alcohol

Yield: 28%

TLC (silica gel): $R_f$=0.52 (tol/EA=1/2)

Melting point: 127° C.

$^1$H-NMR (250 MHz, $d^6$-DMSO, TMS, ppm): 9.72 (s, 1H, phenyl-OH); 7.29 (s, 1H, H-(C3)); 6.83–6.65 (m, 2H, H-(C3), H-(C5)); 5.13 (t, 1H, benzyl-OH); 4.45 (d, 2H, $CH_2$).

31.1.c 2,5-Dichloro-4-hydroxybenzyl alcohol

Yield: 33%

TLC (silica gel): $R_f$=0.52 (tol/EA=1/2)

Melting point: 144° C.

$^1$H-NMR (250 MHz, $d^6$-DMSO, TMS, ppm): 10.52 (s, 1H, phenyl-OH); 7.40 (s, 1H, H-(C6)); 6.95 (s, 1H, H-(C3)); 5.31 (t, 1H, benzyl-OH); 4.44 (d, 2H, $CH_2$).

31.2.a 4-Methoxytrityl 2-fluoro-4-hydroxybenzyl ether

Yield: 95%

TLC (silica gel): $R_f$=0.38 (tol/EA=10/1)

31.2.b 4-Methoxytrityl 3-chloro-4-hydroxybenzyl ether

Yield: 89% (foam/resin)

TLC (silica gel): $R_f$=0.35 (tol/EA=10/1)

31.2.c 4-Methoxytrityl 2-chloro-4-hydroxybenzyl ether

Yield: 93% (foam/resin)
TLC (silica gel): $R_f$=0.52 (tol/EA=1/2)

31.2.d 4-Methoxytrityl 4-hydroxybenzyl ether

Yield: 93% (foam/resin)
TLC (silica gel): $R_f$=0.52 (tol/EA=1/2)
$^1$H-NMR (250 MHz, CDCl$_3$, TMS, ppm): 7.50–7.05 (m, 14H, phenyl-H, m-H to phenyl-OH); 6.83–6.65 (m, 4H, o-H to phenyl-OH, o-H to —OCH$_3$); 4.8–4.7 (bs, 1H, benzyl-OH); 4.03 (s, 2H, CH$_2$); 3.73 (s, 3H, —OCH$_3$).

31.3.a 3-Fluoro-4-[2-(4-nitrophenyl)ethoxycarbonyloxy]benzyl alcohol

Yield: 78%
TLC (silica gel): $R_f$=0.22 (tol/EA=3/1)
Melting point: 105° C.

31.3.b 2-Chloro-4-[2-(4-nitrophenyl)ethoxycarbonyloxy]benzyl alcohol

Yield: 76%
TLC (silica gel): $R_f$=0.23 (tol/EA=3/1)
$^1$H-NMR (250 MHz, CDCl$_3$, TMS, ppm): 8.18 (m, 2H, o-H to —NO$_2$); 7.48 (d, 1H, H-(C6)); 7.40 (m, 2H, m to NO$_2$); 7.14 (d, 1H, H-(C3)); 7.05 (d, 1H, H-(C5)); 4.72 (s, 2H, —CH$_2$); 4.46 (t, 2H, α-CH$_2$ (NPEE)); 3.13 (t, 2H, β-CH$_2$ (NPEE)); 1.88 (bs, 1H, benzyl-OH ?).

31.3.c 2,5-Dichloro-4-[2-(4-nitrophenyl)ethoxycarbonyloxy]benoyl alcohol

Yield: 62%
TLC (silica gel): $R_f$=0.26 (tol/EA=3/1)
Analysis: C$_{16}$H$_{13}$NO$_6$Cl$_2$ (351.74)

|  | C 49.76 | H 3.39 | N 3.63 |
|---|---|---|---|
| calculated | | | |
| found | 50.00 | 3.58 | 3.60 |

$^1$H-NMR (250 MHz, d$^6$-DMSO, TMS, ppm): 8.18 (m, 2H, o-H to —NO$_2$); 7.65–7.52 (m, 4H, m-H to —NO$_2$, H-(C3), H-(C6)); 5.63 (t, 1H, benzyl-OH); 4.58–4.46 (m, 4H, benzyl-CH$_2$, α-CH$_2$ (NPEE)); 3.15 (t, 2H, β-CH$_2$ (NPEE)).

31.3.d 4-[2-(4-Nitrophenyl)ethoxycarbonyloxy] benzyl alcohol

Yield: 67% (resin)
TLC (silica gel): $R_f$=0.52 (tol/EA=1/2)
Analysis: C$_{16}$H$_{15}$NO$_6$ (351.74)

|  | C 60.57 | H 4.76 | N 4.41 |
|---|---|---|---|
| calculated | | | |
| found | 60.93 | 4.81 | 4.59 |

UV (methanol): $\lambda_{max}$ [nm] (lg ε): 4.02 (268)
$^1$H-NMR (250 MHz, d$^6$-DMSO, TMS, ppm): 8.20 (d, 2H, o-H to —NO$_2$); 7.68 (d, 1H, m-H to OCO); 7.30 (d, 2H, m to NO$_2$); 7.05 (d, 2H, m-H to OCO); 5.2 (t, 1H, benzyl-OH); 4.50–4.25 (m, 4H, —CH$_2$, α-CH$_2$ (NPEE)); 3.13 (t, 2H, p-CH$_2$ (NPEE)).

31.5a 3-Chloro-4-[2-(4-nitrophenyl)ethoxycarbonyloxy]benzyl vinyl ether

Yield: 75% (oil)
TLC (silica gel): $R_f$=0.70 (tol/EA=10/1)
Analysis: C$_{18}$H$_{16}$NO$_6$Cl (377.38)

|  | C 12.33 | H 3.12 | N 2.34 |
|---|---|---|---|
| calculated | | | |
| found | 12.43 | 3.23 | 4.34 |

$^1$H-NMR (250 MHz, d$^6$-DMSO, TMS, ppm): 8.15 (m, 2H, o-H to —NO$_2$); 7.45–7.73 (m, 3H, m to —NO$_2$, H-(C2)); 7.29–7.20 (dd, 1H, H-(C6)); 7.13 (d, 1H, H-(C5)); 4.70 (s, 2H, —CH$_2$); 4.50 (t, 2H, α-CH$_2$ (NPEE)); 4.27 (dd, 1H, trans-vinyl-H); 4.10 (dd, 1H, cis-vinyl-H); 3.13 (t, 2H, β-CH$_2$ (NPEE)).

31.5.b 3-Fluoro-4-[2-(4-nitrophenyl)ethoxycarbonyloxy]benzyl vinyl ether

Yield: 87% (oil)
TLC (silica gel): $R_f$=0.72 (tol/EA=10/1)
Analysis: C$_{18}$H$_{16}$NO$_6$F (361.33)

|  | C 12.33 | H 3.12 | N 2.34 |
|---|---|---|---|
| calculated | | | |
| found | 12.43 | 3.23 | 4.34 |

$^1$H-NMR (250 MHz, d$^6$-DMSO, TMS, ppm): 8.18 (d, 2H, o-H to —NO$_2$); 7.40 (m, 2H, m to —NO$_2$); 7.21–7.06 (m, 3H, H-(C2), H-(C5), H-(C6)); 6.52 (dd, 1H, vinyl-H); 4.72 (s, 2H, —CH$_2$); 4.50 (t, 2H, α-CH$_2$ (NPEE)); 4.28 (dd, 1H, trans-vinyl-H); 4.09 (dd, 1H, cis-vinyl-H); 3.13 (t, 2H, β-CH$_2$ (NPEE)).

31.5.c 2,5-Dichloro-4-[2-(4-nitrophenyl)ethoxycarbonyloxy]benzyl vinyl ether Yield: 84%
TLC (silica gel): $R_f$=0.78 (tol/EA=10/1)
Melting point: 48° C.
Analysis: C$_{18}$H$_{15}$NO$_6$Cl$_2$ (412.23)

|  | C 52.45 | H 3.67 | N 3.40 |
|---|---|---|---|
| calculated | | | |
| found | 52.07 | 3.73 | 3.83 |

$^1$H-NMR (250 MHz, CDCl$_3$, TMS, ppm): 8.18 (d, 2H, o-H to NO$_2$); 7.57 (s, 1H, H-(C6)); 7.41 (d, 2H, m-H to —NO$_2$); 7.21 (s, 1H, H-(C6)); 6.53 (s, 1H, (CH (Cl$_2$BnNPEOC); 4.78 (s, 2H, benzyl-CH$_2$); 4.53 (t, 2H, α-CH$_2$ (NPEE)); 4.37/4.29 (d, 1H, trans-vinyl-H); 4.13 (dd, 1H, cis-vinyl-H); 3.17 (t, 2H, β-CH$_2$ (NPEE)).

31.5.d 4-[2-(4-Nitrophenyl)ethoxycarbonyloxy] benzyl vinyl ether

Yield: 89%
TLC (silica gel): $R_f$=0.88 (tol/EA=3/1)
Melting point: 64° C.
Analysis: C$_{18}$H$_{17}$NO$_6$ (343.33)

|  | C 62.97 | H 4.99 | N 4.08 |
|---|---|---|---|
| calculated | | | |
| found | 62.92 | 5.00 | 4.04 |

UV (methanol): $\lambda_{max}$ [nm] (lg ε): 268 (4.01)
$^1$H-NMR (250 MHz, d$^6$-DMSO, TMS, ppm): 8.18 (d, 2H, o-H to NO$_2$); 7.47–7.31 (m, 4H, m-H to —NO$_2$, m-H to —OCO); 7.12 (m, 2H, o-H to —OCO); 6.52 (q, 1H, CH (BnNPEOC)); 4.73 (s, 2H, benzyl-CH$_2$); 4.48 (t, 2H, α-CH$_2$ (NPEE)); 4.31/4.28 (d, 1H, trans-vinyl-H); 4.08 (dd, 1H, cis-vinyl-H); 3.15 (t, 2H, β-CH$_2$ (NPEE)).

31.5.e 2,5-Dichloro-4-pivaloyloxybenzyl vinyl ether

Yield: 58% (oil)

TLC (silica gel): R$_f$=0.81 (tol/EA=20/1)

Analysis: C$_{14}$H$_{16}$O$_3$Cl$_2$ (303.19)

| | | | |
|---|---|---|---|
| calculated | C 12.33 | H 3.12 | N 2.34 |
| found | 12.43 | 3.23 | 4.34 |

$^1$H-NMR (250 MHz, CDCl$_3$, TMS, ppm): 7.53 (s, 1H, H-(C6)); 7.15 (s, 1H, H-(C3)); 6.53 (q, CH(Cl$_2$BnOEE); 4.78 (s, 2H, benzyl-CH$_2$); 4.36/4.28 (d, 1H, trans-vinyl-H-); 4.13 (dd, 1H, cis-vinyl-H); 1.38 (s, 9H, —CH$_3$).

32.1 2'-O-1-{3-Fluoro-4-[2-(4-nitrophenyl)ethoxycarbonyloxy]benzoyloxy}-ethyl-3',5'-tetraisopropyldisiloxane-1,3-diyluridine 3.50 g (7.19 mmol) of 3',5'-protected uridine are twice dissolved, and coevaporated in a rotary evaporator, in 30 ml of absolute toluene each time. The foam is then taken up in 80 ml of abs. toluene, 3.20 g (8.86 mmol) of the vinyl ether which is dissolved in 64 ml of abs. toluene are added, and 10 ml (100 mg=0.52 mmol) of a stock solution of p-TsOH*H$_2$O in abs. dioxane (1.0 g/100 ml) are added to the colorless solution.

After the mixture has been stirred at room temperature overnight (TLC check), the clear reaction solution is diluted with EA to 300 ml and extracted by shaking twice with 100 ml of saturated NaHCO$_3$ solution and 100 ml of saturated NaCl solution. The aqueous phases are backextracted with 100 ml of EA, and the combined organic phases are dried over Na$_2$SO$_4$, filtered and evaporated in a rotary evaporator. Further purification is by chromatography on a column of diameter 4 cm which is charged with 120 g of flash silica gel and equilibrated with toluene (mobile phase gradient (tol/EA/MeOH in ml): 200/0, 200/20, 250/50, 10/100 (P1+P2); fractions each of 50 ml). The product fractions are evaporated in a rotary evaporator and coevaporated several times with MeOH/CH$_2$Cl$_2$.

In this way, 4.67 g (5.51 mmol, 77%) of colorless foam composed of the two diastereomers (P1+P2) are obtained.

TLC (silica gel): R$_f$=0.60/0.65 (tol/EA=1/1)

Analysis: C$_{39}$H$_{54}$N$_3$O$_{13}$Si$_2$F (848.04)

| | | | |
|---|---|---|---|
| calculated | C 55.24 | H 6.42 | N 4.96 |
| found | 55.06 | 6.48 | 5.07 |

UV (methanol): λ$_{max}$ [nm] (lg ε): 265 (4.33)

$^1$H-NMR (250 MHz, CDCl$_3$, TMS, ppm): 8.93/8.73 (bs, 1H, —NH); 8.19 (m, 2H, o-H to NO$_2$); 7.93/7.84 (d, 1H, H-(C6)); 7.18–6.87 (m, 3H, H-(C2), H-(C5), H-(C6)); 5.78/5.68 (s, 1H, H-(C1')); 5.68–5.59 (m, 1H, H-(C5)), 5.14 (m, 1H, CH(2FPNPE); 4.78–4.46 (m, 4H, benzyl-CH$_2$, α-CH$_2$ (NPEE)); 4.29–3.41 (m, 5H, H-(C2'), H-(C3'), H-(C4'), H-(C5'), H-(C5")); 3.14 (t, 2H, β-CH$_2$(NPEE)); 1.49 (t, 2H, CH$_3$ (2FPNPE);

32.1.a 2'-O-1-{3-Chloro-4-[2-(4-nitrophenyl)ethoxycarbonyloxy]-benzyloxy}-ethyl-3',5'-tetraisopropyldisiloxane-1,3-diyluridine Yield: 86%

TLC (silica gel): R$_f$=0.64/0.68 (tol/EA=1.1)

Analysis: C$_{39}$H$_{54}$N$_3$O$_{13}$Si$_2$Cl (864.50)

| | | | |
|---|---|---|---|
| calculated | C 54.19 | H 6.30 | N 4.86 |
| found | 54.14 | 6.39 | 4.88 |

UV (methanol): λ$_{max}$ [nm] (lg ε): 264 (4.28)

32.1.b 2'-O-1-{2-Chloro-4-[2-(4-nitrophenyl)ethoxycarbonyloxy]benzyloxy}-ethyl-3',5'-tetraisopropyldisiloxane-1,3-diyluridine Yield: 79%

TLC (silica gel): R$_f$=0.65/0.69 (tol/EA=1/1)

Analysis: C$_{39}$H$_{54}$N$_3$O$_{13}$Si$_2$Cl (864.50)

| | | | |
|---|---|---|---|
| calculated | C 54.19 | H 6.30 | N 4.86 |
| found | 54.13 | 6.44 | 4.82 |

UV (methanol): λ$_{max}$ [nm] (lg ε): 265 (4.29)

32.1.c 2'-O-1-{2,5-Dichloro-4-[2-(4-nitrophenyl)ethoxycarbonyloxy]benzyloxy}-ethyl-3',5'-tetraisopropyldisiloxane-1,3-diyluridine Yield: 76% (foam)

TLC (silica gel): R$_f$=0.66/0.69 (tol/EA=1/1)

Analysis: C$_{39}$H$_{53}$N$_3$O$_{13}$Si$_2$Cl (898.94)

| | | | |
|---|---|---|---|
| calculated | C 52.11 | H 5.94 | N 4.67 |
| found | 52.06 | 5.05 | 4.57 |

32.1.d 2'-O-1-{4-[2-(4-Nitrophenyl)ethoxycarbonyloxy]benzyloxy}-ethyl-3',5'-tetraisopropyldisiloxane-1,3-diyluridine Yield: 44% (foam)

TLC (silica gel): R$_f$=0.82/0.84 (tol/EA=1/3)

Analysis: C$_{39}$H$_{55}$N$_3$O$_{13}$Si$_2$ (830.05)

| | | | |
|---|---|---|---|
| calculated | C 56.43 | H 6.68 | N 5.06 |
| found | 56.32 | 6.71 | 5.04 |

UV (methanol): λ$_{max}$ [nm] (lg ε): 264 (4.30)

32.1.e 2'-O-1-(2,5-Dichloro-4-pivaloyloxybenzyloxy)ethyl-3',5'-tetraisopropyldisiloxane-1,3-diyluridine (foam)

TLC (silica gel): R$_f$=0.72/0.79 (tol/EA=1/1)

Analysis: C$_{35}$H$_{54}$N$_2$O$_{10}$Si$_2$Cl$_2$ (789.90)

| | | | |
|---|---|---|---|
| calculated: | C 53.22 | H 6.89 | N 3.55 |
| found: | 53.87 | 7.09 | 3.61 |

32.2 2'-O-1-{3-Fluoro-4-[2-(4-nitrophenyl)ethoxycarbonyl-oxy]benzyloxy}-ethyluridine 4.33 g (5.11 mmol) of 2'-O-1-{3-fluoro-4-(2-(4-nitrophenyl)ethoxycarbonyloxy]benzyloxy}ethyl-3',5'-tetraisopropyldisiloxane-1,3-diyluridine are taken up in 80 ml of a stock solution of TBAF×3H$_2$O (50 mg/ml)/AcOH (50 mg/ml) in dioxane (abs.) and stirred at room temperature overnight. The solution is concentrated to a remaining volume of about 20 ml in a rotary evaporator (45° C.) and the crude product is loaded onto a column (d=5 cm). The column is charged with 150 g of flash silica gel and equilibrated with toluene (mobile phase gradient (tol/EA/MeOH in ml): 200/0, 200/20, 250/50, 200/100, 150/150, 150/150/15, 15/150/30, 150/150/30m (P1+P2); fractions each of 50 ml). The product fractions are evaporated in a rotary evaporator and coevaporated several times with MeOH/CH$_2$Cl$_2$.

In this way, 2.75 g (4.54 mmol, 89%) of colorless foam composed of the two diastereomers (P1+P2) are obtained.

TLC (silica gel): R$_f$=0.45/0.47 (tol/EA/MeOH=5/4/1)

Analysis: C$_{27}$H$_{28}$N$_3$O$_{12}$Si$_2$F (605.53)

| calculated: | C 53.56 | H 4.66 | N 6.94 |
| --- | --- | --- | --- |
| found: | 52.86 | 4.83 | 6.91 | x 0.5 H$_2$O calculated: 52.77, 4.76, 6.84

UV (methanol): λ$_{max}$ [nm] (lg ε): 264 (4.30)

$^1$H-NMR (250 MHz, d$^6$-DMSO, TMS, ppm): 11.28 (bs, 1H, —NH); 8.18 (m, 2H, o-H to NO$_2$); 7.95/7.80 (m, 1H, H-(C6)); 7.63–7.09 (m, 5H, m-H to NO$_2$, H-(C2'''), H-(C5'''), H-(C6''')); 5.91 (m, 1H, H-(C1')); 5.53 (m, 1H, H-(C5)); 5.29–5.09 (m, 2H, HO-(C3'), HO(C5')); 4.95 (m, 1H, CH(2FPNPE)); 4.70–4.36 (m, 4H, benzyl-CH$_2$, α-CH$_2$ (NPEE)); 4.26 (t, 1H, H-(C2')); 4.06 (m, 1H, H-(C3')); 3.87 (m, 1H, H(C4')); 3.78–3.48 (m, 2H, H-(C5'), H-(C5'')); 3.12 (t, 2H, β-CH$_2$ (NPEE)); 1.46/1.38 (d, 3H, CH$_3$ (2FPNPE)).

32.2.a 2'-O-1-{3-Chloro-4-[2-(4-nitrophenyl)ethoxycarbonyloxy]benzyloxy}-ethyluridine Yield: 97% (foam)

TLC (silica gel): R$_f$=0.64/0.68 (tol/EA/MeOH=5/4/1)

Analysis: C$_{27}$H$_{28}$N$_3$O$_{12}$Cl (621.88)

| calculated: | C 52.14 | H 4.54 | N 6.76 |
| --- | --- | --- | --- |
| found: | 51.77 | 4.56 | 6.53 |

UV (methanol): λ$_{max}$ [nm] (lg ε): 265 (4.27)

32.2.b 2'-O-1-{2-Chloro-4-[2-(4-nitrophenyl)ethoxycarbonyloxy]benzyloxy}-ethyluridine Yield: 82%

TLC (silica gel): R$_f$=0.61/0.63 (tol/EA/MeOH=5/4/1)

Analysis: C$_{27}$H$_{28}$N$_3$O$_{12}$Cl (621.88)

| calculated: | C 52.14 | H 4.54 | N 6.76 |
| --- | --- | --- | --- |
| found: | 51.91 | 4.70 | 6.76 |

UV (methanol): λ$_{max}$ [nm] (lg ε): 264 (4.25)

32.2.c 2'-O-1-{2,5-Dichloro-4-[2-(4-nitrophenyl)ethoxycarbonyloxy]benzyloxy}-ethyluridine Yield: 69% (foam)

TLC (silica gel): R$_f$=0.66/0.69 (tol/EA=1/1)

Analysis: C$_{27}$H$_{27}$N$_3$O$_{12}$Cl$_2$ (656.43)

| calculated: | C 49.40 | H 4.15 | N 6.40 |
| --- | --- | --- | --- |
| found: | 48.99 | 4.31 | 6.29 |

32.2.d 2'-O-1-{4-[2-(4-Nitrophenyl)ethoxycarbonyloxy]benzyloxy}-ethyluridine

Yield: 80% yellowish crystals

TLC (silica gel): R$_f$=0.65/0.66 (tol/EA/MeOH=5/4/1)

Analysis: C$_{27}$H$_{29}$N$_3$O$_{12}$ (587.54)

| calculated: | C 55.20 | H 4.97 | N 7.15 |
| --- | --- | --- | --- |
| found: | 54.91 | 5.03 | 7.13 |

UV (methanol): λ$_{max}$ [nm] (lg ε): 264 (4.30)

32.2.e 2'-O-1-(2,5-Dichloro-4-pivaloyloxybenzyloxy)ethyluridine (foam)

TLC (silica gel): R$_f$=0.72/0.79 (tol/EA=1/1)

Analysis: C$_{23}$H$_{28}$N$_2$O$_9$Cl$_2$ (547.39)

| calculated: | C 50.47 | H 5.16 | N 5.12 |
| --- | --- | --- | --- |
| found: | 50.31 | 5.42 | 5.11 |

UV (methanol): λ$_{max}$ [nm] (lg ε): 261 (3.99)

32.3. 2'-O-1-{3-Fluoro-4-[2-(4-nitrophenyl)ethoxycarbonyloxy]benzyloxy}ethyl-5'-DMTR-uridine 2.44 g (4.03 mmol) of predried 2'-O-1-{3-fluoro-4-[2-(4-nitrophenyl)ethoxycarbonyloxy[benzyloxy}ethyluridine are coevaporated twice with 10 ml of abs. toluene each time in a rotary evaporator and then taken up in 20 ml of abs. pyridine, and subsequently 2.05 g (6.06 mmol) of DMTR-Cl are added. The reaction solution is left to stand at room temperature overnight, and the reaction is stopped by adding 10 ml of MeOH and stirring for a further 20 minutes. The solution is then evaporated in a rotary evaporator in vacuo to an oil, which is taken up in 250 ml of EA and extracted by shaking with 150 ml of saturated NaHCO$_3$ solution and 150 ml of saturated NaCl solution twice. The aqueous phase is back-extracted with 150 ml of EA, and the combined org. phases are dried with Na$_2$SO$_4$, filtered and concentrated to an oil. Further purification is by chromatography on a column of diameter 4 cm which is charged with 130 g of flash silica gel and equilibrated with toluene (mobile phase gradient (tol/EA in ml): 300/0, 300/30, 300/50, 250/50, 270/70, 150/50, 150/100, 150/150, 100/200, fractions each of 100 ml). The product fractions are evaporated in a rotary evaporator and coevaporated several times with MeOH/CH$_2$Cl$_2$. This results in 3.76 g (3.98 mmol, 98%) of chromatographically pure colorless foam which is composed of the two diastereomers (P1+P2).

TLC (silica gel): R$_f$=0.57/0.59 (tol/EA/MeOH=5/4/1)

$^1$H-NMR (250 MHz, CDCl$_3$, TMS, ppm): 8.5 (bs, 1H, —NH); 8.18 (m, 2H, o-H to —NO$_1$); 7.96/7.87 (d, 1H, H-(C6)); 7.42–7.00 (m, 14H, phenyl-H, m-H to —OCH$_3$, m-H to —NO$_2$, H-(C2'''), H-(C5'''), H-(C6''')); 6.88–6.79 (m, 4H, o-H to —OCH$_3$); 6.04/5.95 (d, 1H, H-(C')); 5.27 (m, 1H, H-(C5)); 5.14 (m, 1H, CH (2FPNPE)); 4.78–4.29 (m, benzyl-CH$_2$, β-CH$_2$ (NPEE), H-(C2'), H-(C3')); 4.07 (m, 1H, H'-(C4')); 3.78 (s, 6H, —OCH$_3$); 3.51 (m, 2H, H-(C5'), H-(C5")); 2.74/2.58 (d, 1H, HO-(C3')); 1.46/1.40 (d, 3H, CH$_3$ (2FPNPE))

32.4 2'-O-1-{3-Fluoro-4-[2-(4-nitrophenyl) ethoxycarbonyloxy]benzyloxy}ethyl-5'-O-DMTR-uridine-3'-O-phosphorous acid β-cyanoethyl ester N,N-diisopropylamide 600 mg (0.66 mmol) of dry 2'-O-1-{3-fluoro-4-[2-(4-nitrophenyl)ethoxycarbonyloxy]benzyloxy}ethyl-5'-DMTR-uridine are introduced into a 50 ml flask, dried under high vacuum overnight and then taken up in 20 ml of abs. CH$_3$CN. To this are added 6 ml (2.7 mmol) of a stock solution of phosphitylation reagent (0.45 mmol/ml abs. CH$_3$CN) and 6 ml of a stock solution of tetrazole (10 mg/ml), and the mixture is stirred at room temperature for a further 12 h. The reaction is stopped by pouring into 300 ml of NaHCO$_3$/EA (1/1) solution. The phases are separated in a separating funnel, extraction is repeated by shaking with 150 ml of EA, and the combined organic phases are washed twice with 100 ml of saturated NaCl solution each time. Drying over Na$_2$SO$_4$ and filtration are followed by evaporation in a rotary evaporator to an oil. Further purification is by chromatography. For this purpose, a column of diameter 2 cm is charged with 20 g of flash silica gel and conditioned with toluene (mobile phase gradient (tol/EA in ml): 100/20, 210/70; fractions each of 10 ml). The product fractions are evaporated in a rotary evaporator and converted into a foam with 10 ml portions of CH$_2$Cl$_2$/MeOH. The product is dried at room temperature under high vacuum.

This results in 650 mg (0.587 mmol, 89%) of colorless foam.

TLC (silica gel): R$_f$=0.65/0.57 (tol/EA/MeOH=5/4/1)

Analysis: C$_{57}$H$_{64}$PN$_3$O$_{15}$F (1109.13)

|  | | | |
|---|---|---|---|
| calculated: | C 61.73 | H 5.82 | N 6.31 |
| found: | 61.56 | 5.82 | 5.67 |

UV (methanol): λ$_{max}$ [nm] (lg ε): 264 (4.30)

$^1$H-NMR (250 MHz, CDCl$_3$, TMS, ppm): 8.18 (m, 2H, o-H to —NO$_2$); 8.09–7.84 (bs/m, 2H, —NH, H-(C6)); 7.46–7.00 (m, 14H, phenyl-H, m-H to —OCH$_3$, m-H to —NO$_2$, H-(C2'''), H-(C5'''), H-(C'''6)); 6.87–6.76 (m, 4H, o-H to —OCH$_3$); 6.08/5.96 (m, 1H, H-(C1')); 5.27 (m, 1H, H-(C%)); 5.14 (m, 1H, CH (2FPNPE); 4.77–4.42 (m, benzyl-CH$_2$, α-CH$_2$ (NPEE), H-(C2'), H-(C3')); 4.29–4.13 (m, 1H, H'-(C4')); 3.97–3.33 (m, 12H, —OCH$_3$, POCH$_2$, N—CH, H-(C5'), H-(C5")); 3.15 (t, β-CH$_2$ (NPEE)); 2.64–2.33 (m, 2H, CH$_2$-CN); 1.50/0.98 (m, 15H, CH$_3$ (2FPNPE), CH(CH$_3$)$_2$);

$^{31}$P-NMR (400 MHz, CDCl$_3$, H$_3$PO$_4$, ppm): 151.18; 150.87; 150.61; 150.36.

33. Oligoribonucleotide syntheses with homogeneous sequences and intact 2'-O-NPE protective group

33.1 Use of nucleoside phosphitamides with the cyanoethyl radical as phosphate protective group A uridine (Example 27) bound to a support forms the 3' end of the oliogonucleotide to be synthesized, i.e. after elimination of the DMTR group it is possible to condense on the first uridine phosphitamide (Example 14). The stepwise condensation yields are determined by measuring the absorption of the dimethoxytrityl cation at 498 nm. The nucleoside phospitamides are prepared as 0.1M solutions in absolute acetonitrile.

5'-HO-(UUU UUU UUU UUU)*-OH (SEQ ID NO:1)

*=2'-O-[1-(4-nitrophenylethoxy)ethyl] (2'-O-NPEE) protected

The condensation time for the synthesis of the 12-meric uridine is 1200 seconds.

After the last 5'-O-DMTR group had been eliminated it was possible to calculate the average condensation yield as 100%. After elimination of the oligomer from the support, approximately 46 OD$_{265}$ of 12-meric uridine were obtained. The calculated overall yield of product is 100%.

33.2 5'-HO-(AAA AAA AAA A)*-OH (*=2'-O-NPEE-protected) (SEQ ID NO:3)

The synthesis of the 10-meric adenosine with intact 2'-O-NPEE group (use of Example 21) starts with an adenosine (Example 29) bonded via the 3'-O-succinate to the support material. The condensation time is 1200 seconds.

The average condensation yield after 8 condensations is 100%. The 10-meric adenosine ribonucleotide is eliminated with intact 5'-O-DMTR group manually from the support. The result is (determined by photometry) 24 OD$_{260}$ (trityl on). The resulting trityl on crude product is purified using OPC (oligonucleotide purification cartridges). The required oligomer from which any incorrect sequences have been removed is obtained in its trityl off form (after elimination of the DMTR group with 2% strength trifluoroacetic acid).

For the OPC purification, 18.7 OD$_{260}$ are used and 10 OD$_{260}$ of purified ribonucleotide are obtained, which corresponds to a yield of 54%.

33.3 5'-HO-(CCC CCC CCC C)*-OH (*=2'-O-NPEE-protected) (SEQ ID NO:3)

From Example 17 and 28.

The condensation time for the 10-meric cytidine ribonucleotide is 1200 seconds. Since the ribonucleotide is obtained in its trityl on form after elimination from the support, only 8 condensations can be used to determine the average condensation yield. It is 91%. The calculated yield of product is 74% based on the first condensation. After elimination from the support with ammonia, 17.5 OD$_{270}$ of crude product are obtained. The crude product is subjected to OPC purification. It is subsequently obtained in its trityl off form.

33.4 5'-HO-(GGG GGG GGG G)*-OH (* -2-O-NPEE protected) (SEQ ID NO:4)

From Example 30 and 26.

In this synthesis, the condensation time from the fifth condensation is reduced to 700 seconds. The average condensation yield is 93%.

Starting from the first condensation, a 52% yield of product is obtained. 20-23 OD$_{271}$ of trityl on ribonucleotide are obtained after elimination from the support. The crude product is purified using OPC. The trityl off oligomer is obtained in 60% yield (12.8 OD$_{271}$).

34. Use of nucleoside phosphitamides with the NPE radical as phosphate protective group Nucleoside phosphitamides with the NPE phosphate protective group are used in all the syntheses described hereinafter.

34.1 5'-HO-(UUU UUU UUU U)*-OH (SEQ ID NO:5)

5'-HO-(UUU UUU UUU UUU)*-OH (*=2'-O-NPEE-protected) (SEQ ID NO:1)

Use of Example 27 and 18.

For the two sequences shown above, condensation times of 1200 seconds are used.

The average condensation yields are 98% for the 10-meric uridine and 99% for the 12-meric uridine.

The calculated yields of product are 83% and 88% respectively.

Both oligomers are obtained after elimination from the support in the trityl off .form. The crude yield of 10-meric uridine is 31.6 $OD_{265}$ and of the 12-mer is 33.8 $OD_{265}$.

34.2 5'-HO-(AAA AAA AAA A) *-OH (SEQ ID NO:2)

5'-HO-(AAA AAA AAA A)*-OH (SEQ ID NO:2)

5'-HO-(AAA AAA AAA A)*-HO (*=2'-O-NPEE protected) (SEQ ID NO:2)

Three 10-meric adenosine ribonucleotides were synthesized with three different batches of adenosine phosphitamide. Use of Example 29 and 22. The average condensation yields are 95% (Compound 2) and 98% (Compounds 1+3).

The condensation time is 1200 seconds in each case. The last sequence was purified using OPC.

34.3 5'-HO-(CCC CCC CCC C)*-OH (*=2'-O-NPEE protected) (SEQ ID NO:3)

Use of Example 28 and 18.

The average condensation yield after 8 condensations is 89%. The crude product is obtained in its trityl on form after elimination from the support with ammonia. 18.1$OD_{273}$ are obtained and are subjected to an OPC purification. The purified trityl off cytidine ribonucleotide is obtained in 77% yield (14.0 $OD_{273}$).

35. Polyacrylamide gel electrophoresis (PAGE) of the 2'-O-NPEE-protected RNA sequences The analytical polyacrylamide gel (PAGE) is carried out under denaturing conditions.

The gel electrophoresis plates are initially silylated with 20% strength trimethylsilyl chloride in dichloromethane.

To prepare the 20% PAGE, 0.21 mmol of urea, 1 ml of water, 3 ml of gel electrophoresis buffer and 15 ml of 40% strength acrylamide solution are dissolved in a hot water bath and subsequently cooled in an ice bath. After addition of 1 ml of 1.6% strength ammoniumpersulfate solution and 20 ml of tetramethylethylenediamine (TEMED), the solution is poured between the glass plates for the polymerization. Gel electrophoresis buffer in 10-fold dilution is used as electrolyte.

The gel electrophoresis buffer is prepared by dissolving 0.89 mol of tris(hydroxymethyl)aminomethane, 0.89 mol of boric acid and 23 mmol of $Na_2EDTA.2H_2O$ in one liter of water and adjusting to pH 8.

After the samples have been loaded into the chambers provided for this purpose, the gel is developed at 300 volts for three hours. The oligonucleotide bands are stained and visualized by the Stains all method.

Because of the fact that the HPLC chromatograms of the '-O-NPEE-protected oligoribonucleotides (RP-18 column) do not provide unambiguous information about their purity, the PAGE of the individual ribonucleotides will be discussed at this point,

| Number | Sequence | average condensation yield |
|---|---|---|
| 1 | 5'HO—(UUU UUU UUU U)*—OH (SEQ ID NO:5) | 98% |
| 2 | 5'-HO—(UUU UUU UUU UUU)*—OH (SEQ ID NO:1) | 99% |
| 3 | 5'-HO—(UUU UUU UUU UUU)*—OH (SEQ ID NO:1) | 101% |
| 4 | 5'-HO—(AAA AAA AAA A)*—OH (SEQ ID NO:2) | 98% |
| 5 | 5'-HO—(AAA AAA AAA A)*—OH (SEQ ID NO:2) | 95% |

(* = 2'-O—NPEE protected)

Sequences 1, 2 and 5 were synthesized using nucleoside phosphitamides carrying the NPE radical as phosphate protective group, 3 and 4 with those having the cyanoethyl group as phosphate protection. As is to be expected already from the average condensation yields of sequence 1 to 4, very few or no incorrect sequences ought to occur. This is confirmed by the PAGE. In each case one band is obtained for sequences 1 to 4, Likewise for sequence 5 despite the somewhat less good condensation yield of 95%, Sequences 1 to 5 comprise crude products (trityl off) after the elimination from the support, No further purification steps were carried out on 1 to 5.

| Number | Sequence | average condensation yield |
|---|---|---|
| 6 | 5'-HO—(AAA AAA AAA A)*—OH (SEQ ID NO:2) | 98% |
| 7 | 5'-HO—(AAA AAA AAA A)*—H (SEQ ID NO:2) | 100% |
| 8 | 5'-HO—(CCC CCC CCC C)*—OH (SEQ ID NO:3) | 91% |
| 9 | 5'-HO—(GGG GGG GGG G)*—OH (SEQ ID NO:4) | 93% |

(* = 2'-O—NPEE protected)

Sequence 6 was synthesized using a phosphitamide which carries the NPE radical as phosphate protective group. Sequences 7 to 9 were prepared using phosphitamides which have the cyanoethyl group as phosphate protection. 6 to 9 were purified using OPC after the elimination from the support with ammonia. They are obtained in their trityl off form.

Also in this case once again the PAGE shows an extremely high purity of the synthesized oligoribonucleotides 6 to 9. In all cases only one band is obtained, i.e. 6 to 9 are free of incorrect sequences.

36. Oligoribonucleotide syntheses with mixed sequences

5'-HO-(CUC CGG UUC GAU UCC GGA CUC GUC CAC CAU)*-OH (SEQ ID NO:6)

5'-HO-(UUG GCG UGG AGA GGU CUC CGG UUC GAU UCC GGA CUC GUC CAC CAG)*-OH (*=2'-O-NPEE protected) (SEQ ID NO:7)

Use of Example 27, 30, 14, 21, 17, 26.

The condensation time is 700 seconds for both sequences. In each case average condensation yields of 99% are obtained. Product yields of 45% are obtained with both syntheses.

The 30-meric oligomer is obtained after elimination from the support in its trityl off form in 95 $OD_{264}$, and the 45-mer is obtained as trityl on compound in 85–93 $OD_{263}$.

The 45-meric oligonucleotide (17.0 $OD_{263}$) is subjected to an OPC purification. The purified product is obtained in the trityl off form in 8.6 $OD_{263}$ (51% yield).

37. Elimination of the 2'-O-NPEE protective group from the synthesized RNA sequences 1. 100 μl of 4% strength pTsOH (methylene chloride/methanol 4:1) are added per 1.0 OD of oligonucleotide.

After a reaction time of two hours, the particular sample is neutralized with 0.84M ammonia/methanol solution and evaporated in a Speed vac rotary evaporator.

2. In a first purification step, the free RNA fragments are precipitated as $Na^+$ salts from ethanol with sodium acetate.

10 to 20 μl of 0.1M sodium acetate solution pH 7 are added per 1.0 OD of oligoribo-nucleotide. The RNA is precipitated with a 4- to 5-fold volume of ethanol at –40° C. overnight.

3. The resulting $Na^+$ salts of the RNA are purified by RP-18 chromatography.

The product peaks are collected and evaporated in a Speed vac rotary evaporator.

The free oligoribonucleotides resulting after this elimination process are then checked for their purity by HPLC (RP-18) and PAGE.

Investigations on the free oligoribonucleotides.

The analytical investigations on the completely deprotected oligoribonucleotides are carried out on reversed phase material (RP-18).

The mobile phase is composed of an acetonitrile/buffer system (1:1) and 0.1M triethyl-ammonium acetate buffer pH 7.

The RP-18 column is eluted with a linear gradient from 2.5% to 50% acetonitrile over the course of 52 minutes. The buffer system is prepared with sterile water. Experimental constants: Merck-Hitatchi-I-6200 Intelligent Pump 100 RP-18, 5 μm, l=125 mm, d=4 mm.

Mobile Phase:

| Time (min) | % A | % B |
|---|---|---|
| 0 | 5 | 95 |
| 2 | 5 | 95 |
| 32 | 40 | 60 |
| 52 | 100 | 0 |
| 55 | 100 | 0 |
| 60 | 5 | 95 |

The following sequences were deprotected:

| Number of the 2'-O-NPEE protected RNA | Sequence | Sequence Identification |
|---|---|---|
| 1 | 5'-HO—UUU UUU UUU U—OH | SED ID NO:5 |
| 3 | 5'-HO—UUU UUU UUU UUU—OH | SEQ ID NO:1 |
| 7 | 5'-HO—AAA AAA AAA A—OH | SEQ ID NO:2 |
| 10 | 5'-HO—CCC CCC CCC C—OH | SEQ ID NO:3 |
| 9 | 5'-HO—GGG GGG GGG G—OH | SEQ ID NO:4 |
| 11 | 5'-HO—CUC CGG UUC GAU UCC GGA CUC GUC CAC CAU—OH | SEQ ID NO:6 |
| 12 | 5'-HO—UUG GCG UGG AGA GGU CUC CGG UUC GAU UCC GGA CUC GUC CAC CAG—OH | SEQ ID NO:7 |

The HPLC chromatograms show in all cases a single peak, which suggests the conclusion that the purified, completely deprotected RNA fragments have a high purity.

38. Stability Tests

To test the stability, the following uridine derivatives were incubated in 0.05N HCl/MeOH (1:2), 30 mmolar solution, 20° C., pH 2.0 (Table 1) or in 80% acetic acid, molar solution, 20° C. (Table 2) and the half-life for deprotection was determined:

TABLE 1

(values +/– 10%)

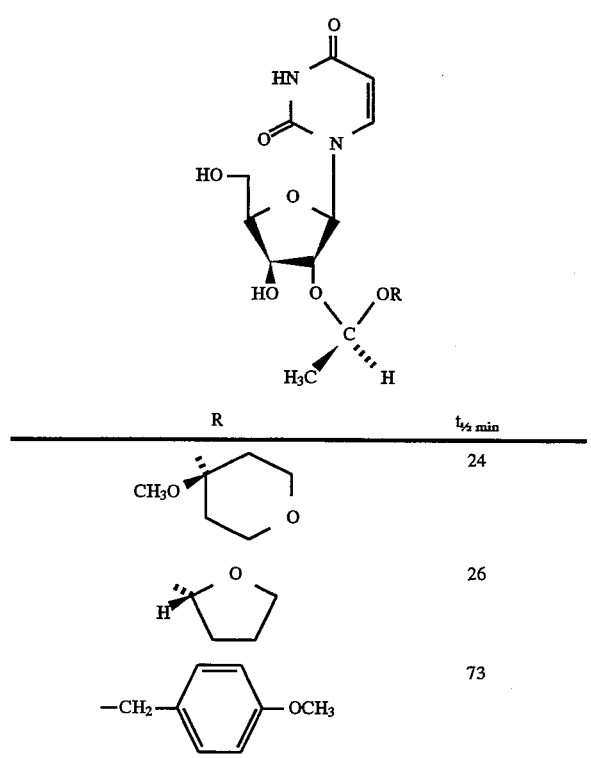

TABLE 1-continued
(values +/− 10%)
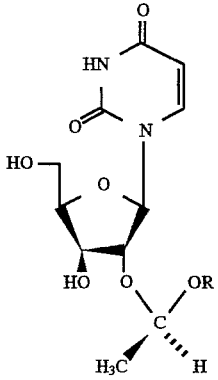
| R | $t_{½}$ min |
|---|---|
| 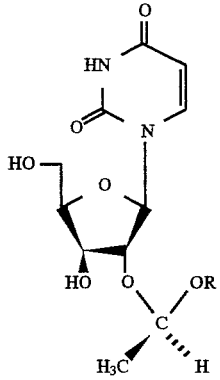 | 82 |
| 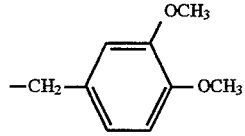 | 154 |
| 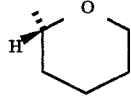 | 175 |
| 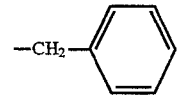 | 222 |
| 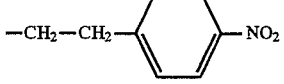 | 230 |
| $-CH_2-CH_2-Cl$ | 620 |
| 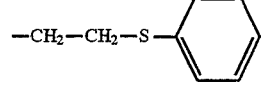 | 840 |
| 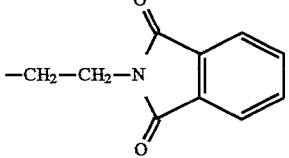 | approx. 1200 |
TABLE 1-continued
(values +/− 10%)
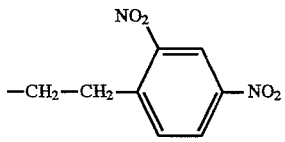
| R | $t_{½}$ min |
|---|---|
| 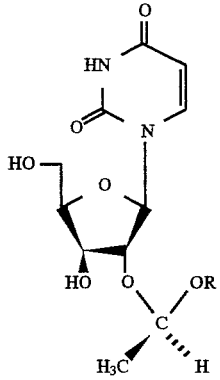 | 1960 |
| 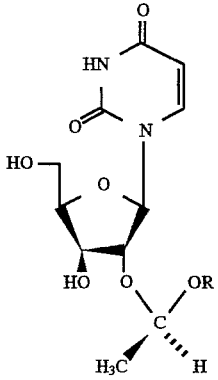 | 2240 |
| 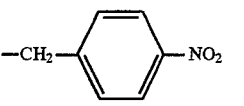 | 3120 |
| 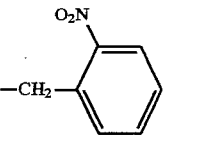 | 3120 |
| $-CH_2-CH_2-CN$ | 3370 |
| $-CH_2-CH_2-NO_2$ | 4030 |
| 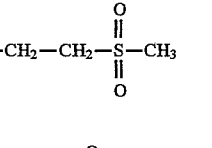 | approx. 14000 |

TABLE 2
Values +/− 5%
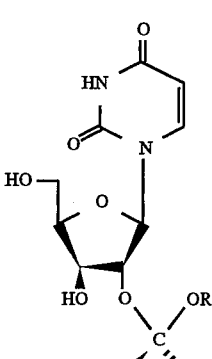
| R | $t_{½\,min}$ |
|---|---|
| 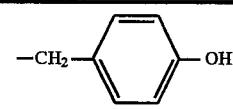 | 21 |
| 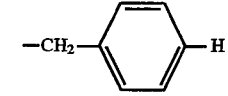 | 66 |
| 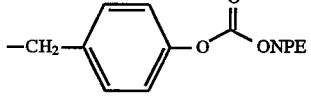 | 104 |
| 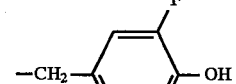 | 48 |
| 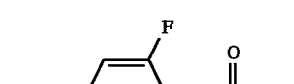 | 305 |
| 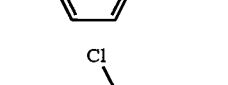 | 55 |
| 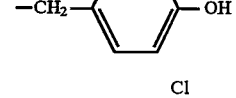 | 250 |
TABLE 2-continued
Values +/− 5%
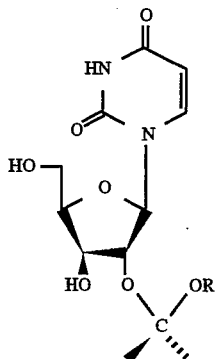
| R | $t_{½\,min}$ |
|---|---|
| 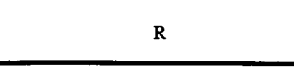 | 1300 |
| 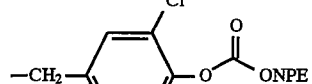 | 1355 |
| 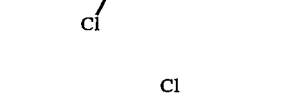 | 1128 |
Abbreviations:
| | |
|---|---|
| 4-DMAP | 4-Dimethylaminopyridine |
| DMTR | Dimethoxytrityl |
| NPE | Para-nitrophenylethoxy |
| NPEE | 1-(para-Nitrophenylethoxy)ethyl |
| NPEOC | Para-nitrophenylethoxycarbonyl |
| TBDMS | Tert.-butyldimethylsilyl |

We claim:

1. A process for preparing a compound of formula I:

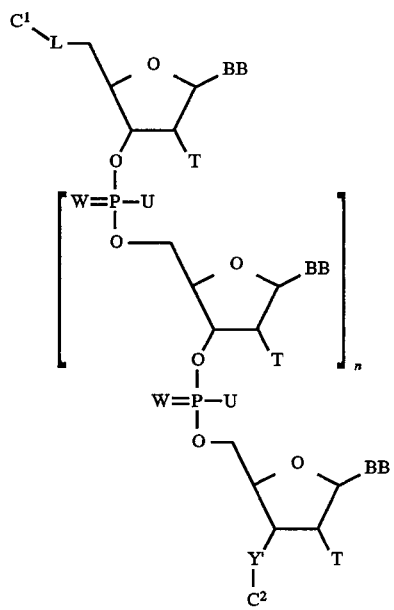
(I)

in which n is a number ranging from 1–150,

L is oxy, sulfanediyl, or imino,

BB is, independently of one another,

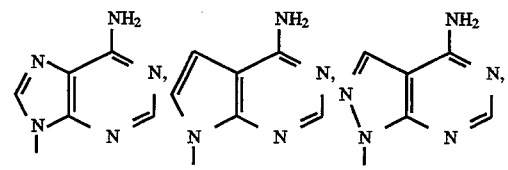

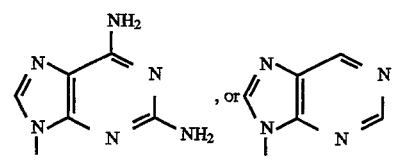

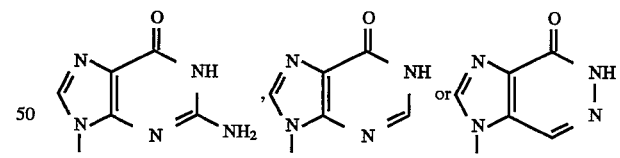

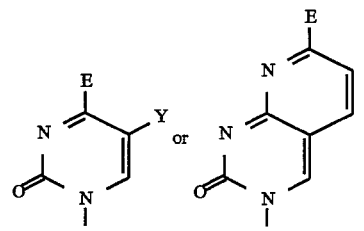

wherein E is OH or $NH_2$, and Y is hydrogen, $C_1$-$C_4$-alkyl, fluorine, chlorine, bromine, $C_2$-$C_6$-alkenyl, or $C_2$-$C_6$-alkynyl, BB can, besides the natural nucleosides, also be other modified nucleosides, W is, independently of one another, oxygen or sulfur, T is, independently of one another, hydrogen, $OC_1$-$C_{18}$-alkyl, $OC_1$-$C_{18}$-alkenyl, $OC_1$-$C_{18}$-alkynyl, or OH, but OH in at least one case, Y' is oxy, sulfanediyl, imino, $(CH_2)_k$, or $N(CH_2)_k$ where k is an integer ranging from 1 to 18, U is hydroxyl, mercapto, SeH, $C_1$-$C_{18}$-alkoxy, $C_1$-$C_{18}$-alkyl, $C_6$-$C_{20}$-aryl, $C_6$-$C_{14}$-aryl-$C_1$-$C_8$-alkyl, $NHR^{17}$, $NR^{17}R^{18}$, or a radical of the formula $(OCH_2CH_2)_cO(CH_2)_\gamma CH_2 R^{20}$, wherein $R^{17}$ is $C_1$-$C_{18}$-alkyl, $C_6$-$C_{20}$-aryl, $C_6$-$C_{14}$-aryl-$C_1$-$C_8$-alkyl, $-(CH_2)_d-[NH(CH_2-)_d]_8-NR^{19}R^{19}$, in which d is an integer ranging from 2 to 6 and 6 is an integer ranging from 0 to 6, $R^{18}$ is $C_1$-$C_{18}$-alkyl, $C_6$-$C_{20}$-aryl, $C_6$-$C_{14}$-aryl-$C_1$-$C_8$-alkyl or, in the case of $NR^{17}R^{18}$, together with $R^{17}$ and the nitrogen atom carrying them, a 5–6-membered heterocyclic ring, $R^{19}$ is, independently of one another, hydrogen, $C^1$-$C_6$-alkyl, or $C_1$-$C_4$alkoxy-$C_1$-$C_6$-alkyl, c is an integer ranging from 1 to 100, γ is an integer ranging from 0 to 18, and $R^{20}$ is hydrogen or a functional group;

$C^1$ and $C^2$ are identical or different and are hydrogen, $C_1$-$C_{18}$-alkyl, $C_2$-$C_{18}$-alkenyl, $C_2$-$C_{18}$-alkynyl, $C_1$-$C_{18}$-alkylcarbonyl, $C_2$-$C_{18}$-alkenylcarbonyl, $C_1$-$C_{18}$-alkynylcarbonyl, $C_6$-$C_{20}$-aryl, $C_6$-$C_{14}$-aryl-$C_1$-$C_8$-alkyl, or a radical of the formula II:

(II)

wherein

W is as defined above,

Q and Q' are, independently of one another, hydroxyl, mercapto, SeH, $C_1$-$C_{22}$-alkoxy, -O-$(CH_2)_b$-$NR^{15}R^{16}$ wherein b is 1 to 6 and $R^{15}$ and $R^{16}$ are, independently of one another, hydrogen, $C_1$-$C_{18}$-alkyl, $C_6$-$C_{20}$-aryl, $C_6$-$C_{14}$-aryl-$C_1$-$C_8$-alkyl, $C_6$-$C_{14}$-aryl-$C_1$-$C_6$-alkoxy, wherein aryl may be a heteroaryl, and aryl is unsubstituted or substituted by 1, 2, or 3 identical or different radicals selected from the group consisting of carboxyl, amino, nitro, $C_1$-$C_4$-alkylamino, $C_1$-$C_6$-alkoxy, hydroxyl, fluorine, chlorine, bromine, and cyano, or $R^{15}$ and $R^{16}$ are independently $C_1$-$C_{18}$-alkylmercapto, $NHR^{17}$, or $NR^{17}R^{18}$ where $R^{17}$ and $R^{18}$ are as defined above, or together with the nitrogen atom carrying them, a 3–6-membered ring, Q and Q' are a radical of the formula III:

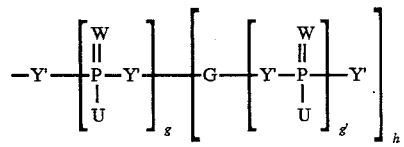

(III)

wherein g and g' are independently 0 or 1, h ranges from 0 to 10,

G is independently $C_2$-$C_{12}$-alkylene, $C_6$-$C_{14}$-aryl-di-$C_1$-$C_8$-alkylene, or $C_6$-$C_{18}$-arylene, and is unsubstituted or substituted one to three times by fluorine, chlorine, bromine, amino, hydroxyl, $C_1$-$C_{18}$-alkyl, $C_1$-$C_{18}$-alkoxy, $C_1$-$C_{18}$-alkoxycarbonyl, $C_6$-$C_{14}$-aryl, $C_6$-$C_{14}$-aryl-$C_1$-$C_{18}$-alkyl, $C_6$-$C_{14}$-aryl-$C_1$-$C_8$-alkoxy, $(CH_2CH_2N')_l CH_2 C_{12}$, or $(CH_2 N')_l CH_2$, wherein l is an integer ranging from 1 to 11 and N' is oxy, sulfanediyl, imino, or methylene, and W, U and Y' are as defined above; or Q and Q' are a group which favors intracellular uptake or acts as a label of a DNA probe or attacks a target nucleic acid on hybridization of an oligonucleotide analog, with crosslinking or cleavage, wherein the nucleic acid sequence in formula I may be interrupted one or more times by linkers of the formula III, and conjugates can be formed also via the nucleosides or via the phosphodiester or phosphothio-diester backbone; the process comprising the steps of a) coupling a compound of the formula X:

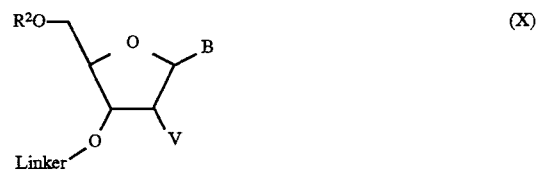

(X)

wherein

Linker contains a hydroxy group replaceable by a solid support, $R^2$ is a dimethoxytrityl, monomethoxytrityl, pixyl, or trityl radical, B is

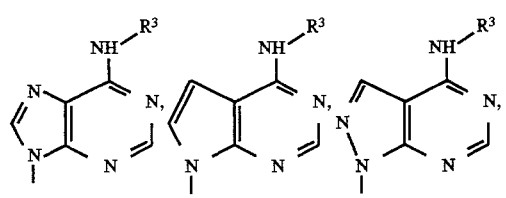

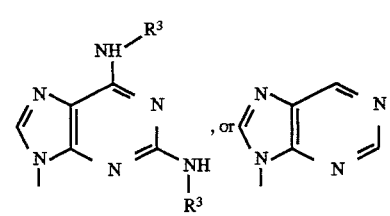

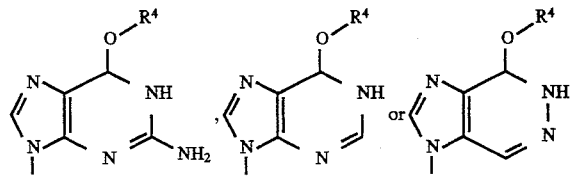

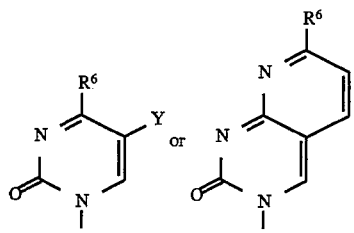

wherein $R^3$ is, in each case, independently of one another, a group of the formula

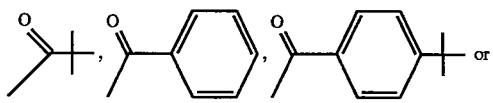

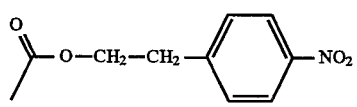

$R^4$ is hydrogen or 2-(p-nitrophenyl)ethyl, $R^5$ is

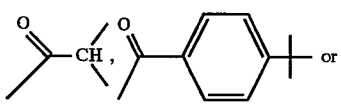

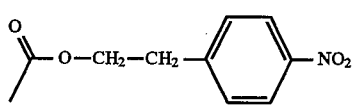

$R^6$ is OH, $NH_2$,

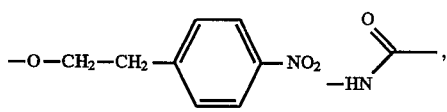

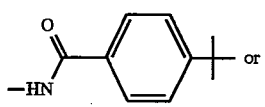

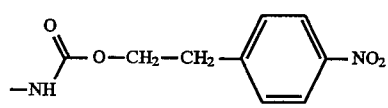

wherein Y is hydrogen, $C_1$–$C_4$-alkyl, fluorine, chlorine, bromine, $C_2$–$C_6$-alkenyl, or $C_2$–$C_6$-alkynyl, B can, besides the natural nucleosides, also be other modified nucleosides whose amino or hydroxyl groups are protected by suitable known protecting groups, V is hydrogen, O—$C_1$–$C_{18}$-alkyl, O—$C_1$–$C_{18}$-alkenyl, or O—$C_1$–$C_{18}$-alkynyl, or O—CH($CH_3$)—$OR^1$, to a solid support, to obtain a compound of formula Xa:

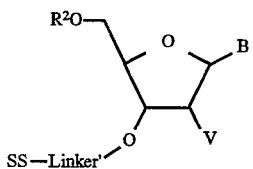

wherein SS, $R^2$, B, and V are defined above, and Linker' is the residue of said Linker, b) eliminating the 5' protecting group to obtain a compound of formula Xb:

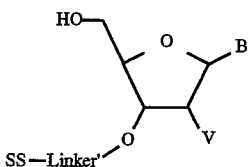

wherein SS, B, Linker', and V are defined above, c) reacting the resulting compound of formula Xb with a compound of the formula XI:

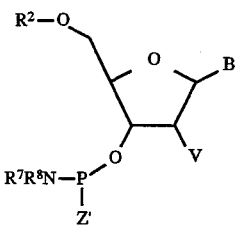

in which $R^2$, V and B are defined above, $R^7$ and $R^8$ are identical or different and are $C_1$–$C_8$-alkyl, $C_5$–$C_{12}$-cycloalkyl, benzyl, or phenyl, or are together with the nitrogen atom to which they are bonded, a saturated or unsaturated unsubstituted or substituted heterocyclic ring, said heterocyclic ring optionally possessing at least one additional heteroatom, Z' is $OR^9$, $C_1$–$C_{18}$-alkyl, $C_1$–$C_{18}$-alkoxy, $C_6$–$C_{20}$-aryl, or $C_6$–$C_{14}$-aryl-$C_1$–$C_8$-alkyl, where $R^9$ is a group of the formula

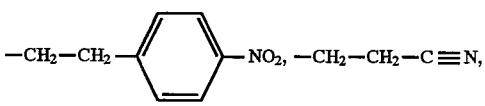

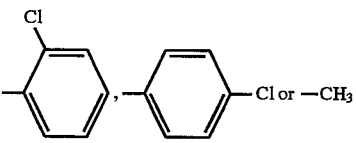

or a benzyl group, which is not substituted or is ring-substituted one to four times, where the substituent is or substituents are, independently of one another, fluorine, chlorine, bromine, a $C_1$–$C_4$-alkyl, nitro, methoxy, or carboxyl group, to obtain a compound of formula XIa:

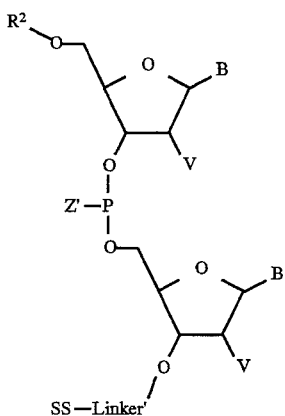

(XIa)

wherein $R^2$, B, Z', V, Linker', and SS are defined above, d) oxidizing or sulfurizing the resulting compound of formula XIa to obtain a compound of formula XIb:

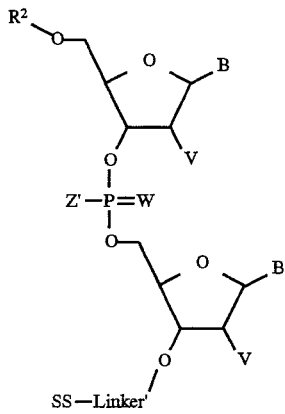

(XIb)

wherein $R^2$ B, Z', SS, W, Linker', and V are defined above e) repeating reaction steps b–d to obtain the required chain length, wherein V is O—CH(CH$_3$)—OR$^1$ at least once in the chain, f) eliminating the oligonucleotide from the solid support SS, and eliminating the protecting groups on the phosphate and nucleic bases, resulting in the compound of the formula XII:

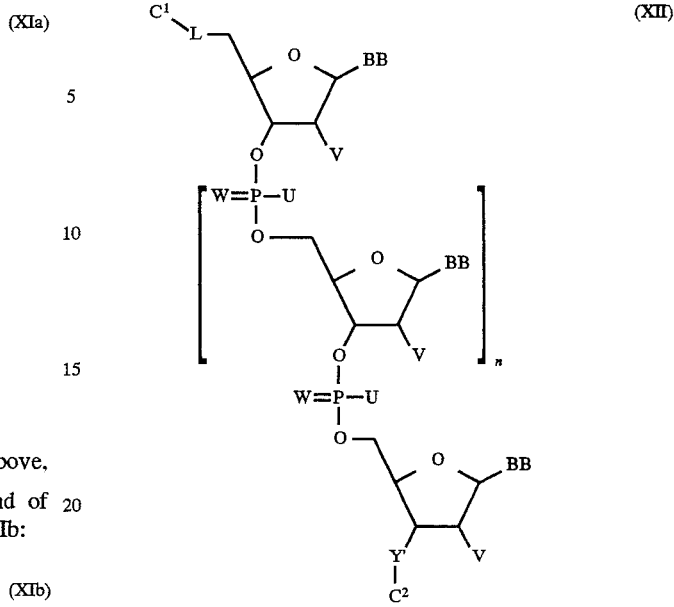

(XII)

wherein n, L, BB, W, V, Y', U, $C^1$, and $C^2$ are as defined above; and g) incubating the compound of the formula XII at an acidic pH in the presence of p-toluenesulfonic acid to obtain a compound of formula I.

2. The process according to claim 1 wherein the other modified nucleosides representing BB are 5-(hydroxymethyl)uridine, 5-aminouridine, pseudouridine, dihydrouridine, inosine, 8-aza-7-deazaadenosine, tubercidin, nebularine, xanthosine, 2-aminoadenosine, ethenoadenosine, 7-deazaguanosine, O4-methylthymidine, N6-methyladenosine, O6-methylguanosine, or pyridopyrimidine nucleosides.

3. The process according to claim 1 wherein the functional group representing $R^{20}$ is hydroxyl, amino, NHR$^{17}$, COOH, CONH$_2$, COOR$^{21}$, fluorine, chlorine or bromine wherein is a $C_1$–$C_4$-alkyl radical.

4. The process according to claim 1 wherein the heterocyclic ring represented by NR$^{17}$R$^{18}$ contains another heteroatom, the heteroatom being O, S, or N.

5. The process according to claim 1 wherein said Linker is succinic ester.

6. The process according to claim 1, wherein in step g), the compound of formula XII is incubated at an acidic pH in a 1–30% solution of p-toluenesulfonic acid in a suitable organic solvent for 0.5–10 hours, the resulting mixture is neutralized, the solvent is evaporated, and purification is effected to obtain a compound of formula I.

7. A compound of the formula XII (XII)

wherein
n is a number ranging from 1–150,
L is oxy, sulfanediyl, or imino,
BB is, independently of one another,

[structures of modified nucleobases]

wherein E is OH or $NH_2$, and Y is hydrogen, $C_1$–$C_4$-alkyl, fluorine, chlorine, bromine, $C_2$–$C_6$-alkenyl, or $C_2$–$C_6$-alkynyl, BB can, besides the natural nucleosides, also be other modified nucleosides, W is, independently of one another, oxygen or sulfur, V is, independently of one another, hydrogen, $OC_1$–$C_{18}$-alkyl, $OC_2$–$C_{18}$-alkenyl, $OC_2$–$C_{18}$-alkynyl, or $OCH(CH_3)OR^1$, but is $OCH(CH_3)OR^1$ in at least one case, wherein $R^1$ is —$(CH_2)_r$—X wherein r is 1 or 2 and X is $C_6$–$C_{12}$-aryl that is unsubstituted or substituted one or more times by hydroxyl, mercapto, nitro, fluorine, chlorine, bromine, $C_1$–$C_6$-alkyl, $C_1$–$C_6$-alkoxy, $C_1$–$C_6$-alkylmercapto, $C_2$–$C_6$-alkenyl, $C_3$–$C_6$-alkynyl, C(O)OH, C(O)$NH_2$, C(O)O—$C_1$–$C_{18}$-alkyl, C(O)O—$C_6$–$C_{12}$-aryl, C(O)-$C_1$–$C_{18}$-alkyl, C(O)-$C_6$–$C_{12}$-aryl, O—C(O)$NH_2$, O-C(O)O—$C_1$–$C_{18}$-alkyl, O—C(O)O—$C_6$–$C_{12}$-aryl, O—C(O)-$C_1$–$C_{18}$-alkyl, O-C(O)-$C_6$–$C_{12}$-aryl, O—C(O)—{$CH_2$}$_r$—$X^1$, or O—C(O)O—{$CH_2$}$_r$—$X^1$, wherein $X^1$ is $C_6$–$C_{12}$-aryl that is unsubstituted or substituted one to three times by amino, hydroxyl, nitro, $C_1$–$C_6$-alkyl, $C_1$–$C_6$-alkoxy, $C_1$–$C_6$-alkoxycarbonyl, fluorine, chlorine, or bromine, wherein when r is 2, X is also CN, S-phenyl, $SO_2$-phenyl, N-phthalimide, or $NO_2$, Y' is oxy, sulfanediyl, imino, $(CH_2)_k$, or $N(CH_2)_k$ wherein k is an integer ranging from 1 to 18, U is hydroxyl, mercapto, SeH, $C_1$–$C_{18}$-alkoxy, $C_1$–$C_{18}$-alkyl, $C_6$–$C_{20}$-aryl, $C_6$–$C_{14}$-aryl-$C_1$–$C_8$-alkyl, $NHR^{17}$, $NR^{17}NR^{18}$, or a radical of the formula $(OCH_2CH_2)_cO(CH_2)_YCH_2R^{20}$, wherein $R^{17}$ is $C_1$–$C_{18}$-alkyl, $C_6$–$C_{20}$-aryl, $C_6$–$C_{14}$-aryl-$C_1$–$C_8$-alkyl, —$(CH_2)_d$—{$NH(CH_2)_d$}$_\delta$—$NR^{19}R^{19}$, in which d is an integer ranging from 2 to 6 and $\delta$ is an integer ranging from 0 to 6, $R^{18}$ is $C_1$–$C_{18}$-alkyl, $C_6$–$C_{20}$-aryl, $C_6$–$C_{14}$-aryl-$C_1$–$C_8$-alkyl or, in the case of $NR^{17}R^{18}$, together with $R^{17}$ and the nitrogen atom carrying them, a 5–6-membered heterocyclic ring optionally containing another heteroatom selected from O, S, and N, $R^{19}$ is, independently of one another, hydrogen, $C_1$–$C_6$-alkyl, or $C_1$–$C_4$-alkoxy-$C_1$–$C_6$-alkyl, c is an integer ranging from 1 to 100, Y is an integer ranging from 0 to 18, and $R^{20}$ is hydrogen or a functional group;

$C^1$ and $C^2$ are identical or different and are hydrogen, $C_1$–$C_{18}$-alkyl, $C_2$–$C_{18}$-alkenyl, $C_2$–$C_{18}$-alkynyl, $C_1$–$C_{18}$-alkylcarbonyl, $C_2$–$C_{18}$-alkenylcarbonyl, $C_2$–$C_{18}$-alkynylcarbonyl, $C_6$–$C_{20}$-aryl, $C_6$–$C_{14}$-aryl-$C_1$–$C_8$-alkyl, or a radical of the formula II:

$$Q-\underset{\underset{W}{\parallel}}{\overset{}{P}}-Q' \qquad (II)$$

wherein

W is oxygen or sulfur,

Q and Q' are, independently of one another, hydroxyl, mercapto, SeH, $C_1$–$C_{22}$-alkoxy, —O—$(CH_2)_b$—$NR^{15}R^{16}$ wherein b ranges from 1 to 6, and $R^{15}$ and $R^{16}$ are, independently of one another, hydrogen, $C_1$–$C_{18}$-alkyl, $C_6$–$C_{20}$-aryl, $C_6$–$C_{14}$-aryl-$C_1$–$C_8$-alkyl, $C_6$–$C_{14}$-aryl-$C_1$–$C_8$-alkoxy, wherein aryl may also be a heteroaryl, and aryl is unsubstituted or substituted by 1, 2, or 3 identical or different radicals selected from carboxyl, amino, nitro, $C_1$–$C_4$-alkylamino, $C_1$–$C_6$-alkoxy, hydroxyl, fluorine, chlorine, bromine, and cyano, or $R^{15}$ and $R^{16}$ are independently $C_1$–$C_{18}$-alkylmercapto, $NHR^{17}$, or $NR^{17}R^{18}$, wherein $R^{17}$ and $R^{18}$ are as defined above, or, together with the nitrogen atom carrying them, form a 3–6-membered ring, or Q and Q' are, independently of one another, a radical of the formula III:

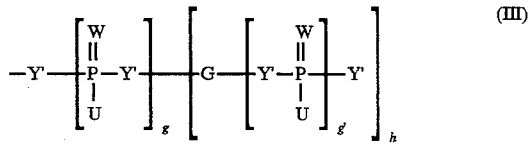

(III)

wherein g and g' are independently 0 or 1, h is 0 to 10,

G is independently $C_2$–$C_{12}$-alkylene, $C_6$–$C_{14}$-aryl-di-$C_1$–$C_8$-alkylene, or $C_6$–$C_{18}$-arylene, and is unsubstituted or substituted one to three times by fluorine, chlorine, bromine, amino, hydroxyl, $C_1$–$C_{18}$-alkyl, $C_1$–$C_{18}$-alkoxy, $C_1$–$C_{18}$-alkoxycarbonyl, $C_6$–$C_{14}$-aryl, $C_6$–$C_{14}$-aryl-$C_1$–$C_{18}$-alkyl, $C_6$–$C_{14}$-aryl-$C_1$–$C_8$-alkoxy, $(CH_2CH_2N')_iCH_2CH_2$, or $(CH_2N')_iCH_2$, wherein l is an integer ranging from 1 to 11 and N' is oxy, sulfanediyl, imino, or methylene, and W, U, and Y' are as defined above; or Q and Q' are a group which favors intracellular uptake or acts as a label of a DNA probe or attacks a target nucleic acid on hybridization of an oligonucleotide analog, with crosslinking or cleavage, wherein the nucleic acid sequence in formula XII may be interrupted one or more times by compounds of the formula III defined above, and conjugates can be formed also via the nucleosides or via the phosphodiester or phosphothiodiester backbone.

8. The compound of formula XII of claim 7 wherein said modified nucleosides defined in BB are 5-(hydroxymethyl)-uridine, 5-aminouridine, pseudouridine, dihydrouridine, inosine, 8-aza-7-deazaadenosine, tubercidin, nebularine, xanthosine, 2-aminoadenosine, ethenoadenosine, 7-deazaguanosine, O4-methylthymidine, N6-methyladenosine, O6-methylguanosine, or pyrido-pyrimidine nucleosides.

9. The compound of formula XII of claim 7 wherein said functional group defined in $R^{20}$ is hydroxyl, amino, $NHR^{17}$, COOH, $CONH_2$, $COOR^{21}$, fluorine, chlorine, or bromine, wherein $R^{21}$ is a $C_1$–$C_4$-alkyl radical.

10. The compound of formula XII of claim 7 wherein said 3–6 membered ring defined by $NR^{17}R^{18}$ contains an additional heteroatom, said heteroatom being O, S, or N.

11. A compound of formula VI:

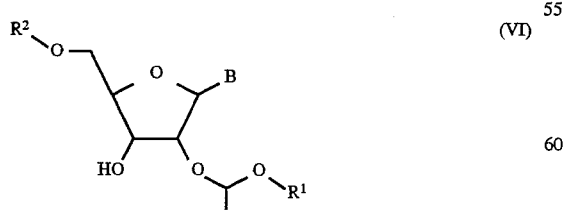

(VI)

wherein $R^1$ is —$(CH_2)_r$—X, wherein r is 1 or 2;

X is a $C_6$–$C_{12}$-aryl that is unsubstituted or substituted one or more times by hydroxyl, mercapto, nitro, fluorine, chlorine, bromine, $C_1$–$C_6$-alkyl, $C_1$–$C_6$-alkoxy, $C_1$–$C_6$-alkylmercapto, $C_2$–$C_6$-alkenyl, $C_3$–$C_6$-alkynyl, C(O)OH, $C(O)NH_2$, $C(O)O$—$C_1$–$C_{18}$-alkyl, $C(O)O$—$C_6$–$C_{12}$-aryl, $C(O)$-$C_1$–$C_{18}$-alkyl, $C(O)$-$C_6$–$C_{12}$-aryl, O—$C(O)NH_2$, O—$C(O)O$—$C_1$–$C_{18}$-alkyl, O—$C(O)$O—$C_6$–$C_{12}$-aryl, O—$C(O)$-$C_1$–$C_{18}$-alkyl, O—$C(O)$-$C_6$–$C_{12}$-aryl, O—$C(O)$—$(CH_2)_r$—$X^1$ or O—$C(O)O$—$(CH_2)_r$—$X^1$, wherein $X^1$ is a $C_6$–$C_{12}$-aryl which is unsubstituted or substituted from one to three times by amino, hydroxyl, nitro, $C_1$–$C_6$-alkyl, $C_1$–$C_6$-alkoxy, $C_1$–$C_6$-alkoxycarbonyl, fluorine, chlorine or bromine; and when r is 2, X is also CN, S-phenyl, $SO_2$-phenyl, N-phthalimide, or $NO_2$;

$R^2$ is dimethoxytrityl, monomethoxytrityl, pixyl or trityl;

B is

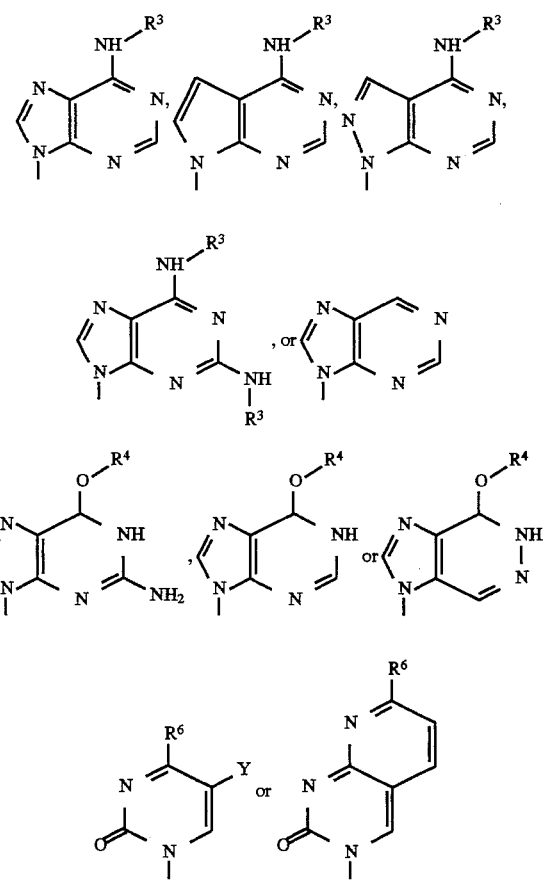

wherein $R^3$ is, in each case, independently of one another, a group of the formula

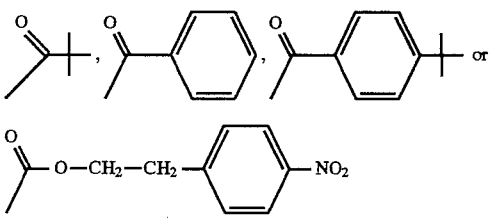

$R^4$ is hydrogen or 2-(p-nitrophenyl)ethyl;

$R^5$ is

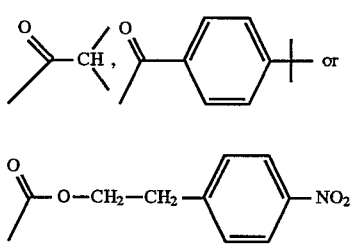

$R^6$ is OH, $NH_2$,

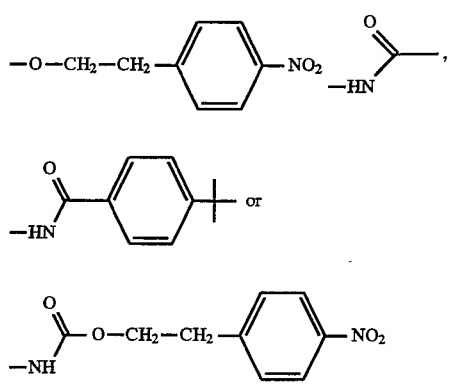

wherein Y is hydrogen, $C_1$–$C_4$-alkyl, fluorine, chlorine, bromine, $C_2$–$C_6$-alkenyl, or $C_2$–$C_6$-alkynyl; and B can, besides the natural nucleosides, also be other modified nucleosides having amino or hydroxyl groups protected by suitable protecting groups.

12. The compound of formula VI of claim 11, wherein B is a modified protected nucleoside having at least one hydroxyl group modified by a para-nitrophenylethyloxycarbonyl group, a benzoyl group or a para-(t-butyl)benzoyl group.

13. The compound of formula VI of claim 11, wherein B is a modified protected nucleoside having at least one amino group modified by a benzoyl, a para-(t-butyl)benzoyl, a para-nitrophenylethyloxycarbonyl, an isobutyryl, or para-(tert-butyl)phenylacetyl group.

14. The compound of formula VI of claim 11, Wherein $R^1$ is —$(CH_2)_r$—X, wherein when r is 1, X is a $C_6$–$C_{12}$-aryl that is unsubstituted or substituted one to three; times by fluorine, chlorine, bromine, $C_1$–$C_4$-alkyl, $C_1$–$C_4$-alkoxy, O—C(O)—$(CH_2)_r$—$X^1$ or O—C(O)O—$(CH_2)_r$—$X^1$, wherein $X^1$ is a $C_{6-12}$-aryl that is unsubstituted or substituted one to three times by $C_1$–$C_4$-alkyl, $C_1$–$C_4$-alkoxy, fluorine, chlorine or bromine; and when r is 2, X is 4-nitrophenyl; and $R^2$ is dimethoxytrityl.

15. The compound of formula VI of claim 11, wherein r is 1 and X is phenyl or $C_1$–$C_4$-alkoxyphenyl.

16. The compound of formula VI of claim 11, wherein

B is

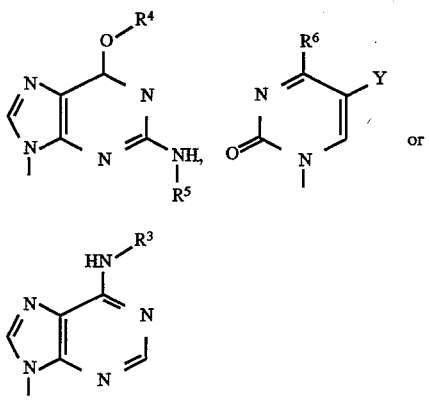

wherein Y, $R^e$, $R^4$, $R^5$, and $R^6$ are defined as in claim 11.

17. A compound of formula VIII:

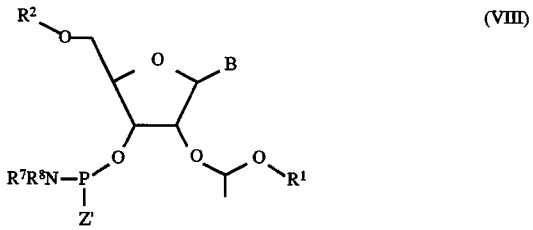

(VIII)

wherein $R^1$ is —$(CH_2)_r$—X, wherein r is 1 or 2;

X is a $C_6$–$C_{12}$-aryl that is unsubstituted or substituted one or more times by hydroxyl, mercapto, nitro, fluorine, chlorine, bromine, $C_1$–$C_6$-alkyl, $C_1$–$C_6$-alkoxy, $C_1$–$C_6$-alkylmercapto, $C_2$–$C_6$-alkenyl, $C_3$–$C_6$-alkynyl, C(O)OH, C(O)$NH_2$, C(O)O—$C_1$–$C_{18}$-alkyl, C(O)O—$C_6$–$C_{12}$-aryl, C(O)-$C_1$–$C_{18}$-alkyl, C(O)-$C_6$–$C_{12}$-aryl, O—C(O)$NH_2$, O—C(O)O—$C_1$–$C_{18}$-alkyl, O—C(O)O—$C_6$–$C_{12}$-aryl, O—C(O)-$C_1$–$C_{18}$-alkyl, O—C(O)-$C_6$–$C_{12}$-aryl, O—C(O)—$(CH_2)_r$—$X^1$ or O—C(O)O—$(CH_2)_r$—$X^1$, wherein $X^1$ is a $C_6$–$C_{12}$-aryl that is unsubstituted or substituted one to three times by amino, hydroxyl, nitro, $C_1$–$C_6$-alkyl, $C_1$–$C_6$-alkoxy, $C_1$–$C_6$-alkoxycarbonyl, fluorine, chlorine, or bromine, and when r is 2, X is also CN, S-phenyl, $SO_2$-phenyl, N-phthalimide or $NO_2$;

$R^2$ is dimethoxytrityl, monomethoxytrityl, pixyl, or trityl;

$R^7$ and $R^8$ are identical or different and are selected from $C_1$–$C_8$-alkyl, $C_5$–$C_{12}$-cycloalkyl, benzyl and phenyl, or are, together with the nitrogen atom to which they are bonded, a saturated or unsaturated heterocyclic ring, said heterocyclic ring optionally possessing at least one additional heteroatom;

Z' is $OR^9$, $C_1$–$C_{18}$-alkyl, $C_1$–$C_{18}$-alkoxy, $C_6$–$C_{20}$-aryl, $C_6$–$C_{14}$-aryl-$C_1$–$C_8$-alkyl, wherein $R^9$ is a group of the formula

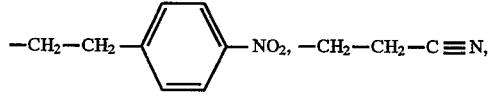

93
-continued

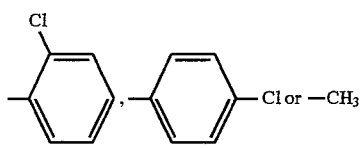

or a benzyl group, which is unsubstituted or ring-substituted one to four times, independently of one another, by a fluorine, chlorine, bromine, a $C_1$–$C_4$-alkyl, nitro, methoxy, or carboxyl group;

B is

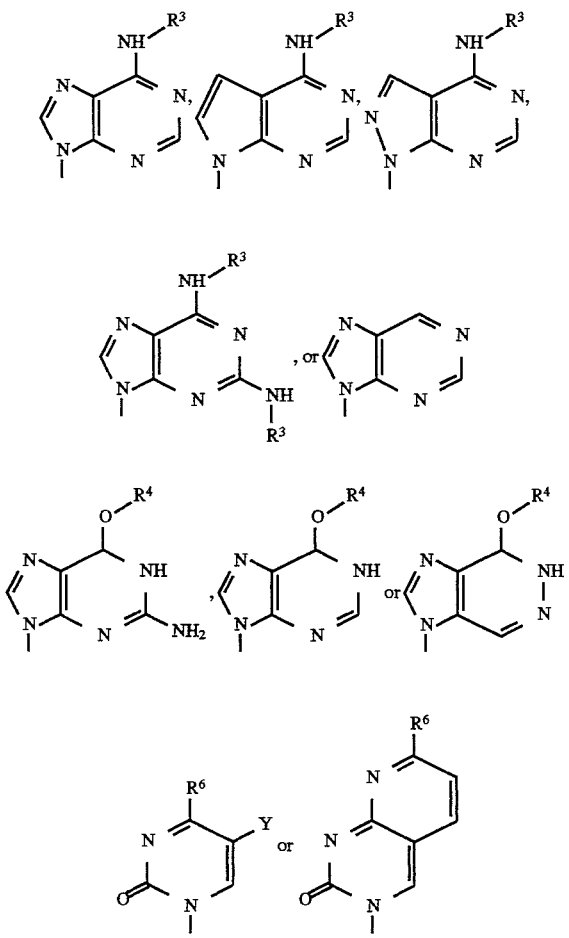

wherein $R^3$ is, in each case, independently of one another, a group of the formula

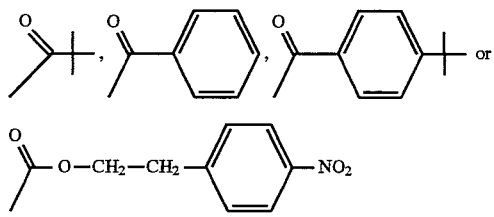

$R^4$ is hydrogen or 2-(p-nitrophenyl)ethyl;

94

$R^5$ is

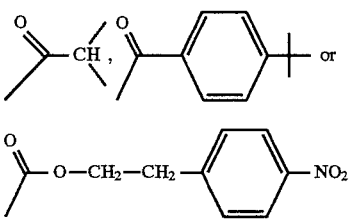

$R^6$ is OH, $NH_2$,

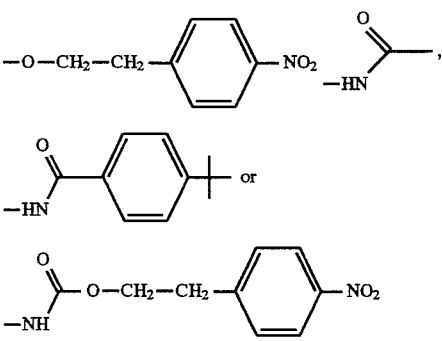

wherein Y is hydrogen, $C_1$–$C_4$-alkyl, fluorine, chlorine, bromine, $C_2$–$C_6$-alkenyl, or $C_2$–$C_6$-alkynyl; and B can, besides the natural nucleosides, also be other modified nucleosides having amino or hydroxyl groups protected by suitable protecting groups.

18. The compound of formula VIII of claim 17, wherein B is a modified protected nucleoside having at least one hydroxyl group modified by a para-nitrophenylethyloxycarbonyl group, a benzoyl group, or a para-(t-butyl)benzoyl group.

19. The compound of formula VIII of claim 17 wherein B is a modified protected nucleoside having at least one amino group modified by a benzoyl, para-(t-butyl)benzoyl, para-nitrophenylethyloxycarbonyl, isobutyryl, or para-(tert-butyl)phenylacetyl group.

20. A compound of formula VIII of claim 17, wherein $R^1$ is $(CH_2)_r$—X, wherein when r is 1, X is a $C_6$–$C_{12}$-aryl that is unsubstituted or substituted one to three times by fluorine, chlorine, bromine, $C_1$–$C_4$-alkyl, $C_1$–$C_4$-alkoxy, O—C(O)—$(CH_2)_r$—$X^1$ or O—C(O)—$(CH_2)_r$$X^1$, wherein $X^1$ is a $C_6$–$C_{12}$-aryl that is unsubstituted or substituted one to three times by $C_1$–$C_4$-alkyl, $C_1$–$C_4$-alkoxy, fluorine, chlorine or bromine, and when r is 2, X is 4-nitrophenyl;

$R^2$ is dimethoxytrityl;

Z' is $OR^9$;

$R^7$ and $R^8$ are identical or different and are selected from isopropyl, $C_5$–$C_8$-cycloalkyl, benzyl and phenyl, or are, together with the nitrogen atom to which they are bonded, a saturated or unsaturated heterocyclic ring, said heterocyclic ring optionally possessing at least one additional heteroatom; and Y is hydrogen, $CH_3$, or 1-propynyl.

21. The compound of formula VIII of claim 20, wherein $R^7$ and $R^8$, together with the nitrogen atom to which they are bonded, are a morpholine group.

22. The compound of formula VIII of claim 20, wherein said heterocyclic ring formed from said $R^7R^8N$— is substituted by at least one OC(O)O—$C_1$–$C_4$-alkyl ester.

23. The compound of formula VIII of claim 17, wherein r is 1 and X is phenyl or $C_1$–$C_4$-alkoxyphenyl.

24. The compound of formula VIII of claim 17, wherein B is

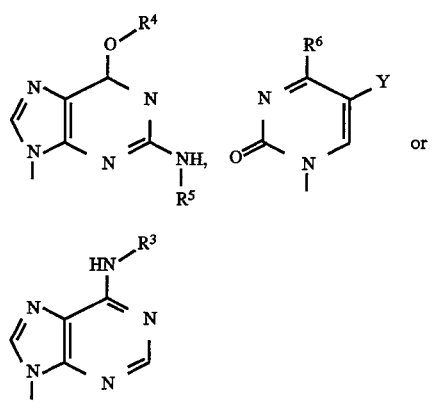

or

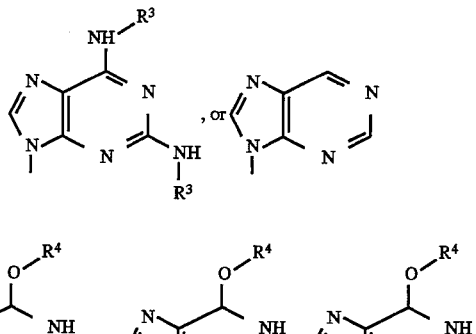

wherein Y, $R^3$, $R^4$, $R^5$, and $R^6$ are defined as in claim 17.

25. A compound of formula IX:

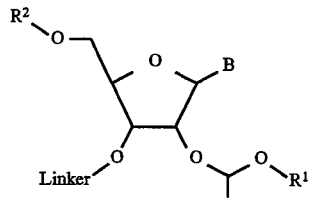
(IX)

wherein

Linker contains a hydroxy group replaceable by a solid support, $R^1$ is —$(CH_2)_r$—X wherein r is 1 or 2; and X is a $C_6$–$C_{12}$-aryl that is unsubstituted or substituted one or more times by hydroxyl, mercapto, nitro, fluorine, chlorine, bromine, $C_1$–$C_6$-alkyl, $C_1$–$C_6$-alkoxy, $C_1$–$C_6$-alkylmercapto, $C_2$–$C_6$-alkenyl, $C_3$–$C_6$-alkynyl, C(O)OH, C(O)$NH_2$, C(O)O—$C_1$–$C_{18}$-alkyl, C(O)O—$C_6$-$C_{12}$-aryl, C(O)-$C_1$–$C_{18}$-alkyl, C(O)-$C_6$–$C_{12}$-aryl, O—C(O)$NH_2$, O—C(O)O—$C_1$–$C_{18}$-alkyl, O—C(O)O—$C_6$–$C_{12}$-aryl, O—C(O)-$C_1$–$C_{18}$-alkyl, O—C(O)-$C_6$–$C_{12}$-aryl, O—C(O)—$(CH_2)_r$—$X^1$ or O—C(O)O—$(CH_2)_r$—$X^1$, wherein $X^1$ is a $C_6$–$C_{12}$-aryl that is unsubstituted or substituted one to three times by amino, hydroxyl, nitro, $C_1$–$C_6$-alkyl, $C_1$–$C_6$-alkoxy, $C_1$–$C_6$-alkoxy-carbonyl, fluorine, chlorine or bromine, and when r is 2, X is also CN, S-phenyl, $SO_2$-phenyl, N-phthalimide or $NO_2$;

$R^2$ is dimethoxytrityl, monomethoxytrityl, pixyl, or trityl;

B is

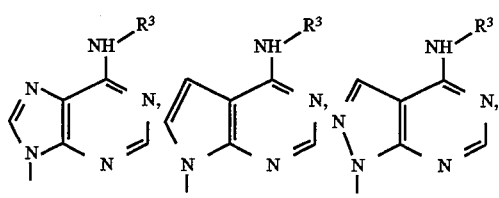

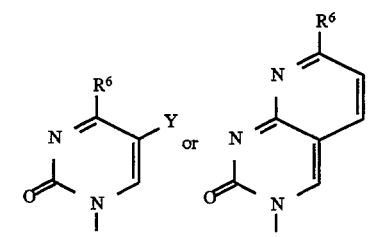

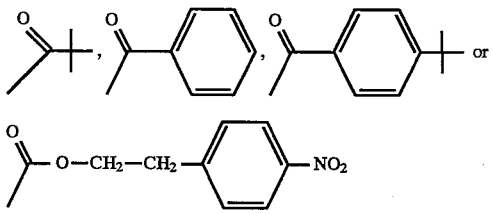

wherein $R^3$ is, in each case, independently of one another, a group of the formula

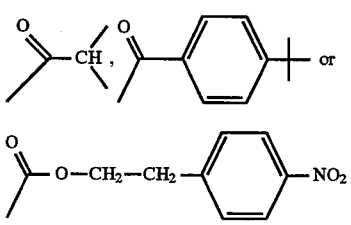

$R^4$ is hydrogen or 2-(p-nitrophenyl)ethyl;

$R^5$ is

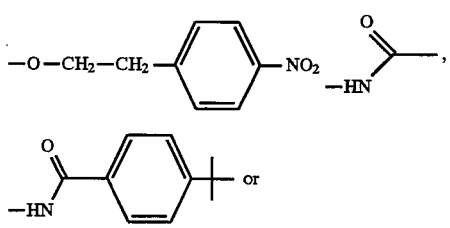

$R^6$ is OH, $NH_2$,

—O—$CH_2$—$CH_2$—⌬—$NO_2$, ⌬—C(O)—HN—,

⌬—C(O)—HN— or

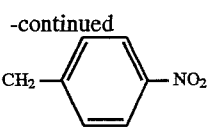

wherein Y is hydrogen, $C_1$–$C_4$-alkyl, fluorine, chlorine, bromine, $C_2$–$C_6$-alkenyl, or $C_2$–$C_6$-alkynyl; and B can, besides the natural nucleosides, also be other modified nucleosides having amino or hydroxyl groups protected by suitable protecting groups.

26. The compound of formula IX of claim 25, wherein B is a modified protected nucleoside having at least one hydroxyl group modified by a para-nitrophenylethyloxycarbonyl group, a benzoyl group, or a para-(t-butyl)benzoyl group.

27. The compound of formula IX of claim 25, wherein B is a modified protected nucleoside having at least one amino group modified by a benzoyl, a para-(t-butyl)benzoyl, a para-nitrophenylethyloxycarbonyl, an isobutyryl, or a para-(tert-butyl)phenylacetyl group.

28. The compound of formula IX of claim 25 wherein $R^1$ is —$(CH_2)_r$—X, wherein when r is 1, X is a $C_6$–$C_{12}$-aryl that is unsubstituted or substituted one to three times by fluorine, chlorine, bromine, $C_1$–$C_4$-alkyl, $C_1$–$C_4$-alkoxy, O—C(O)—$(CH_2)_r$—$X^1$, O—C(O)O—$(CH_2)_r$$X^1$, wherein $X^1$ is a $C_1$–$C_{12}$-aryl that is unsubstituted or substituted one to three times by $C_1$–$C_4$-alkyl, $C_1$–$C_4$-alkoxy, fluorine, chlorine or bromine, when r is 2, X is 4-nitrophenyl; and $R^2$ is dimethoxytrityl.

29. The compound of formula IX of claim 25, wherein B is

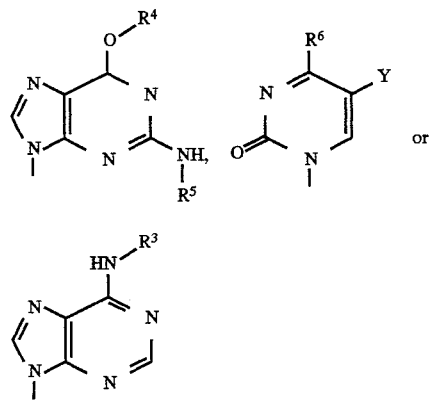

wherein Y, $R^3$, $R^4$, $R^5$, and $R^6$ are defined as in claim 25.

30. The compound of formula IX of claim 25, wherein r is 1 and X is phenyl or $C_1$–$C_4$-alkoxyphenyl.

31. The compound IX of claim 25 wherein said Linker is succinic ester.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: RNA (genomic)

( x i ) SEQUENCE DESCRIPTION: SEQ ID NO:1:

UUUUUUUUUU UU                                                                                                  12

( 2 ) INFORMATION FOR SEQ ID NO:2:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: RNA (genomic)

( x i ) SEQUENCE DESCRIPTION: SEQ ID NO:2:

AAAAAAAAAA                                                                                                     10

( 2 ) INFORMATION FOR SEQ ID NO:3:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: RNA (genomic)

( x i ) SEQUENCE DESCRIPTION: SEQ ID NO:3:

CCCCCCCCCC                                                                                                     10

( 2 ) INFORMATION FOR SEQ ID NO:4:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: RNA (genomic)

( x i ) SEQUENCE DESCRIPTION: SEQ ID NO:4:

GGGGGGGGGG                                                                                                     10

( 2 ) INFORMATION FOR SEQ ID NO:5:

( i ) SEQUENCE CHARACTERISTICS:
      ( A ) LENGTH: 10 base pairs
      ( B ) TYPE: nucleic acid
      ( C ) STRANDEDNESS: single
      ( D ) TOPOLOGY: linear ( i i ) MOLECULE TYPE: RNA (genomic)

( x i ) SEQUENCE DESCRIPTION: SEQ ID NO:5:

UUUUUUUUU    10

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:6:

CUCCGGUUCG AUUCCGGACU CGUCCACCAU    30

( 2 ) INFORMATION FOR SEQ ID NO:7:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:7:

UUGGCGUGGA GAGGUCUCCG GUUCGAUUCC GGACUCGUCC ACCAG    45